(12) United States Patent
Doudna et al.

(10) Patent No.: US 10,253,311 B2
(45) Date of Patent: Apr. 9, 2019

(54) METHODS AND COMPOSITIONS FOR USING ARGONAUTE TO MODIFY A SINGLE STRANDED TARGET NUCLEIC ACID

(71) Applicant: The Regents of the University of California, Oakland, CA (US)

(72) Inventors: Jennifer A. Doudna, Berkeley, CA (US); Emine Kaya, Berkeley, CA (US); Kilian R. Knoll, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/129,382

(22) PCT Filed: Apr. 9, 2015

(86) PCT No.: PCT/US2015/025147
§ 371 (c)(1),
(2) Date: Sep. 26, 2016

(87) PCT Pub. No.: WO2015/157534
PCT Pub. Date: Oct. 15, 2015

(65) Prior Publication Data
US 2017/0175104 A1 Jun. 22, 2017

Related U.S. Application Data

(60) Provisional application No. 61/977,931, filed on Apr. 10, 2014.

(51) Int. Cl.
| | | |
|---|---|---|
| *C12N 15/10* | (2006.01) |
| *C12N 9/22* | (2006.01) |
| *C12N 15/63* | (2006.01) |
| *C07K 14/195* | (2006.01) |
| *C12P 19/34* | (2006.01) |

(52) U.S. Cl.
CPC .......... *C12N 15/102* (2013.01); *C07K 14/195* (2013.01); *C12N 9/22* (2013.01); *C12P 19/34* (2013.01)

(58) Field of Classification Search
CPC ........ C12N 15/102; C12N 9/22; C12N 15/63; C12N /; C07K 14/195; C12P 19/34
USPC ...................................... 435/69.1, 325, 375
See application file for complete search history.

(56) References Cited

U.S. PATENT DOCUMENTS

2006/0141600 A1    6/2006   Joshua-Tor et al.
2013/0217592 A1    8/2013   Samuel et al.

FOREIGN PATENT DOCUMENTS

WO    WO 2007/048629    5/2007
WO    WO 2007/092181    8/2007

OTHER PUBLICATIONS

Carmell, et al.; "The Argonauts family: tentacles that reach into RNAi, deveopmental control, stem cell maintenance, and tumorigenesis"; Genes & Development; vol. 16, pp. 2733-2742 (2002).
Lucas, et al.; "Complete Genome Sequence of the Thermophilic, Piezophilic, Heterotrophic Bacterium Marinitoga piezophila KA3"; J. Bacterial.; vol. 194, No. 21, pp. 5974-5975 (Nov. 2012).
Huang, et al.; "Demystifying the nuclear function of Argonaute proteins"; RNA Biology; vol. 11, No. 1, pp. 18-24 (2014).
Jinek, et al.; "A three-dimensional view of the molecular machinery of RNA interference"; Nature; vol. 457, pp. 405-412 (Jan. 22, 2009).
Meister; "Argonaute proteins: functional insights and emerging roles"; Nature Reviews Genetics; vol. 14, pp. 447-459 (Jul. 2013).
Makarova, et al.; "Prokaryotic homologs of Argonaute proteins are predicted to function as key components of a novel system of defense against mobile genetic elements"; Biology Direct; vol. 4, No. 29, 15 pages (2009).
Swarts, et al.; "DNA-guided DNA interference by a prokaryotic Argonaute"; Nature; vol. 507, 17 pages (Mar. 13, 2014).
Olovnikov, et al.; "Bacterial Argonaute Samples the Transcriptome to Identify Foreign DNA"; Molecular Cell; vol. 51, pp. 594-605 (Sep. 12, 2013).
Kaya, et al.; "A bacterial Argonaute with noncanonical guide RNA specificity"; PNAS; vol. 113, No. 15, pp. 4057-4062 (Apr. 12, 2016).

*Primary Examiner* — Janet L Epps-Smith
(74) *Attorney, Agent, or Firm* — Bozicevic Field & Francis, LLP; Paula A. Borden

(57) ABSTRACT

The present disclosure provides compositions, kits, genetically modified cells, non-human transgenic organisms, and methods for binding and/or cleaving a single stranded target nucleic acid. A method of cleaving includes contacting a single stranded target nucleic acid with (e.g., introducing into a cell) a subject argonaute (Ago) polypeptide and a guide RNA (e.g., having a 5'-OH). In some embodiments, a subject Ago polypeptide includes an amino acid sequence having 70% or more sequence identity with amino acids 282-430 and/or 431-639 of the Marinitoga piezophila argonaute (MpAgo) protein set forth in SEQ ID NO: 1. The present disclosure provides variant Ago polypeptides; and methods of use of same.

31 Claims, 13 Drawing Sheets

Specification includes a Sequence Listing.

| | | | |
|---|---|---|---|
| Homo/1-859 | 579 | LPQGRPPVFQ-----QPVIFLGADVTHPPAGDGKKPSIA---AVVGSM | 618 |
| Drosophila/1-984 | 703 | VPSIRPKVFN-----EPVIFLGADVTHPPAGDNKKPSIA---AVVGSM | 742 |
| Marinitoga/1-639 | 423 | IPECKPFILKKMEDKEKNLYIGIDLSHDT---YARKTNLCIAAVDNT | 466 |
| Thermus/1-685 | 461 | ----QVVALS--GAYPAELAVGFDAGG--RE5FRFGGAAC--AVGGD | 497 |
| Pyrococcus/1-770 | 541 | ----KYYVLD--YRFNYDYIIGIDVAPMKRSEGYIGGSAV--MFDSQ | 579 |

| | | | |
|---|---|---|---|
| Homo/1-859 | 619 | DAHRNRYCATVRVQQHRQEIIQDLAAMVRELLIQF--YKST-RFKPT | 662 |
| Drosophila/1-984 | 743 | DAHPSRYAATVRVQQHRQEIIQELSSMVRELLIMF--YKSTGGYKPH | 787 |
| Marinitoga/1-639 | 467 | -GD-ILYIGKH KNLELNEKM-NLDILEKEYIKAFEKYIEKFNVSPE | 509 |
| Thermus/1-685 | 498 | GGH-LLWTLP--EAQAGERI-PQEVVWDLLEETLWAFRRKAGRLPS | 539 |
| Pyrococcus/1-770 | 580 | -GY-IRKIVPIKIGEQRGESV-DMNEFFKEMVDKFKEFNIK--LDNK | 621 |

| | | | |
|---|---|---|---|
| Homo/1-859 | 663 | RIIFYRDGVSEGQFQQVLHHELLAIREACIKLEKDYQPGITFIVVQK | 709 |
| Drosophila/1-984 | 788 | RIILYRDGVSEGQFPHVLQHELTAIREACIKLEPEYRPGITFIVVQK | 834 |
| Marinitoga/1-639 | 510 | NVFILRDGRFIEDIEIIKNFI----S-----YNDTKYTLVEV | 542 |
| Thermus/1-685 | 540 | RVLLLRDGRVPQDEFAL----A----LEA-----LAREGIAYDLVSV | 573 |
| Pyrococcus/1-770 | 622 | KILLLRDGRITNNEEEGLKYI----SEM-----FDIEVVTMDVI-- | 656 |

| | | | |
|---|---|---|---|
| Homo/1-859 | 710 | RHHTRLFCTDKNERVGKSGNIIPAGTTVDTKI-T---HPTEFDFYLCS | 752 |
| Drosophila/1-984 | 835 | RHHTRLFCAEKKEQSGKSGNIIPAGTTVDVGI-T---HPTEFDFYLCS | 877 |
| Marinitoga/1-639 | 543 | NK----INSYDDLKEWIIKLDENTYIYYPKT | 572 |
| Thermus/1-685 | 574 | RK----SGGGRVYPVQGRLADGL-YVPLEDKTFLL-LTV | 606 |
| Pyrococcus/1-770 | 657 | ----KNHPVRAFANMKM-YFNLGGAIYLI-PHK | 683 |

FIG. 1B

|  |  |  |  |
|---|---|---|---|
| Homo/1-859 | 753 | HAGIQGTSRPSHYHVLWDDNRFSSDELQILTYQLCHT------YV | 791 |
| Drosophila/1-984 | 878 | HQGIQGTSRPSHYHVLWDDNHFDSDELQCLTYQLCHT------YV | 916 |
| Marinitoga/1-639 | 573 | FLNQKGVEVK-----ILE---NNTDYTIEEIIEQIYLLTRVAHS | 608 |
| Thermus/1-685 | 607 | HRDFRGTPRPLKLVHEA-----GDTPL----EALAHQIFHLTRLYPA | 644 |
| Pyrococcus/1-770 | 684 | LKQAKGTPIPIKLAKKRII-KNGKVEKQSITRQDVLDIFILTRLNYG | 729 |

|  |  |  |  |
|---|---|---|---|
| Homo/1-859 | 792 | RCTRSVSIPAPAYYAHLVAFRARYHLVDKEHDSAEGSHTSGQSNGRD | 838 |
| Drosophila/1-984 | 917 | RCTRSVSIPAPAYYAHLVAFRARYHLVDKEHDSGEGSHQSGCSEDRT | 963 |
| Marinitoga/1-639 | 609 | TPYTNYKLPYPLHIANKVALT-DYEWKLYIPY------ | 639 |
| Thermus/1-685 | 645 | SGFAFPRLPAPLHLADRLVKEVGRLGIRHLKEVDREKL------ | 682 |
| Pyrococcus/1-770 | 730 | SISADMRLPAPVHYAHKFANAIRNEWKIKEEFLAEGFL------ | 767 |

|  |  |  |  |
|---|---|---|---|
| Homo/1-859 | 839 | HQALAKAVQVHQDTLRTMYFA | 859 |
| Drosophila/1-984 | 964 | PGAMARAITVHADTKKVMYFA | 984 |
| Marinitoga/1-639 |  |  |  |
| Thermus/1-685 | 683 | ---FFV | 685 |
| Pyrococcus/1-770 | 768 | ---YFV | 770 |

FIG. 1B (Cont.)

| | | | |
|---|---|---|---|
| Human/1-859 | 453 | I--ACFAPQRQ-----CTEVHLKSFTEQLRKISRDAGMPIQGQPCFCKY | 494 |
| Drosophila/1-984 | 577 | I--ACFAPQRT-----VREDALRNFTQQLQKISNDAGMPIIGQPCFCKY | 618 |
| Marinitoga/1-639 | 312 | LKELFHNKHSVFYRAAAELGFSKVEFLRDSKTKS------SAFL-Y | 350 |
| Thermus/1-685 | 371 | ASGASLRHT-LHAHPSQGLAFREALRKAKEEGV-----QAVLVLT | 410 |
| Pyrococcus/1-771 | 457 | IIEVVEQVSS--FXKGKELGLAFIAARNKLSS-------- | 486 |

| | | | |
|---|---|---|---|
| Human/1-859 | 495 | AQG--ADSVEPMFRHLKNTYAGLQLVVVILPGKTPVYAEVKRVGDTV | 539 |
| Drosophila/1-984 | 619 | ATG--PDQVEPMFRYLKDTFPGLQLVVVVLPGKTPVYAEVKRVGDTV | 663 |
| Marinitoga/1-639 | 351 | NPEEFTVKNTEFINQIEDNVMAI-----VLLD-K----YIGNIDPLV | 387 |
| Thermus/1-685 | 411 | PPMAWED----RNRLKALL----------LR | 427 |
| Pyrococcus/1-771 | 487 | -----EK-----FEEIKRRL----------FN | 498 |

| | | | |
|---|---|---|---|
| Human/1-859 | 540 | LGMATQCVQMKN-----VQRTTPQ-----TLSNLCLKINVKLGGVNNI | 577 |
| Drosophila/1-984 | 664 | LGMATQCVQAKN-----VNKTSPQ-----TLSNLCLKINVKLGGINSI | 701 |
| Marinitoga/1-639 | 388 | RNFPDNLILQPILKEKLEDIKPF-----IIKSYV--YKMGN----- | 421 |
| Thermus/1-685 | 428 | EGLPSQILNVPLREEERHRWENA------LLGLLAKAGL--- | 460 |
| Pyrococcus/1-771 | 499 | LNVISQVVNEDTLKNKRDKYDRNRLDLFVRHNLLFQVLSKLGV- | 541 |

| | | | |
|---|---|---|---|
| Human/1-859 | 578 | LLPQGRPPVFQ-----QPVIFLGADVTHPPAGDGKKPSIAAVVGSMD | 619 |
| Drosophila/1-984 | 702 | LVPSIRPKVFN-----EPVIFLGADVTHPPAGDNKKPSIAAVVGSMD | 743 |
| Marinitoga/1-639 | 422 | FIPECKPFILKKMEDKEKNLYIGIDLSHDTYAR-KTNLCIAAVDNTG | 467 |
| Thermus/1-685 | 461 | ----QVVALS-GAYPAELAVGFDAGG--RESFRFGGAACAVGGDG | 498 |
| Pyrococcus/1-771 | 542 | ----KYYVLD--YRFNYDYIIGIDVAPXKRSEGYIGGSAVXFDSQG | 581 |

METHODS AND COMPOSITIONS FOR USING ARGONAUTE TO MODIFY A SINGLE STRANDED TARGET NUCLEIC ACID

CROSS-REFERENCE

This application is a national stage filing under 35 U.S.C. § 371 of PCT/US2015/025147, filed Apr. 9, 2015, which claims the benefit of U.S. Provisional Patent Application No. 61/977,931, filed Apr. 10, 2014, each of which applications is incorporated herein by reference in its entirety.

INCORPORATION BY REFERENCE OF SEQUENCE LISTING PROVIDED AS A TEXT FILE

A Sequence Listing is provided herewith as a text file, "BERK-239WO_SeqList_ST25.txt" created on Apr. 9, 2015 and having a size of 67 KB. The contents of the text file are incorporated by reference herein in their entirety.

INTRODUCTION

Argonaute (Ago) proteins are small RNA or DNA guided, site-specific endonucleases, which are present in all three kingdoms of life. The various functions of Argonaute proteins in eukaryotes have been studied extensively and include translational control, transposon silencing, and defense against foreign DNA. However, their function in prokaryotes is still unknown. Recent studies have suggested that prokaryotic Argonautes are involved in identifying foreign genetic elements in a sequence specific manner and/or in the recruitment of nucleases.

Generally, Ago proteins use a guide nucleic acid (e.g., a guide RNA) to identify a target nucleic acid. The guide RNAs utilized by all currently known Ago proteins include a 5'-PO$_4$ (5'-phosphate) and a 3'-OH (3'-hydroxl). Thus, methods that employ the heterologous expression of Ago proteins are limited because the guide RNAs utilized by the heterologously expressed Ago proteins are generally indistinguishable from the thousands of RNAs present in the host cell.

There is a need in the art for a technology that facilitates the precise and controlled targeting of Ago nuclease activity (or other protein activities such as binding) to single stranded target nucleic acids (e.g., ssRNA, ssDNA, mRNA, rRNA, tRNA, microRNA, etc.).

SUMMARY

The present disclosure provides compositions, kits, genetically modified cells, non-human transgenic organisms, and methods for binding and/or cleaving a single stranded target nucleic acid. A method of cleaving includes contacting a single stranded target nucleic acid with (e.g., introducing into a cell) a subject argonaute (Ago) polypeptide and a guide RNA (e.g., having a 5'-OH). The target nucleic acid can be single stranded DNA (ssDNA) or single stranded RNA (ssRNA). In some cases, the target nucleic acid is an ssRNA (e.g., a target cell ssRNA, a viral ssRNA, and the like) selected from: mRNA, rRNA, tRNA, non-coding RNA (ncRNA), long non-coding RNA (lncRNA), and microRNA (miRNA). In some cases, a target nucleic acid is a single stranded DNA (ssDNA) (e.g., a viral DNA, a single stranded region of a double stranded DNA, and the like).

In some cases, the single stranded target nucleic acid is not inside of a cell (e.g., the target nucleic acid is contacted in vitro, e.g., in the absence of a cell). In some cases, the target nucleic acid is inside of a cell (e.g., the target nucleic acid is contacted inside of a cell in vitro or inside of a cell in vivo). For example, the subject methods can be performed outside of a cell in vitro, inside of a cell in vitro or ex vivo, and/or inside of a cell in vivo. In some embodiments, contacting a target nucleic acid with an Ago polypeptide includes introducing the Ago polypeptide into a cell. In some cases, contacting a target nucleic acid with an Ago polypeptide includes introducing into a cell a nucleic acid (e.g., RNA or DNA) encoding the Ago polypeptide.

In some embodiments, contacting a single stranded target nucleic acid with a guide RNA includes introducing the guide RNA into a cell. In some cases, contacting a target nucleic acid with a guide RNA includes introducing into a cell a precursor nucleic acid, where: (i) the precursor nucleic acid is a precursor RNA or a DNA polynucleotide encoding a precursor RNA, and (ii) the precursor RNA is modified, or is cleaved at a cleavage site, to generate the guide RNA. In some cases, a precursor RNA has a cleavage site for a 5'-OH generating ribozyme or nuclease, where the cleavage site is positioned 5' of the targeting nucleotide sequence of the guide RNA. In some cases, a precursor RNA includes a self-cleaving sequence (e.g., a sequence of a self-cleaving ribozyme) that cleaves the precursor RNA at the cleavage site to generate the guide RNA. In some embodiments, the subject methods include introducing into a cell a 5'-OH generating nuclease (e.g., a CRISPR-associated nuclease, e.g., csy4, cas6, cas5, and the like) or a nucleic acid encoding a 5'-OH generating nuclease that cleaves a precursor RNA to generate a guide RNA. In some embodiments, a subject precursor RNA and a subject Ago polypeptide are both encoded by the same DNA polynucleotide.

In some embodiments, a subject Ago polypeptide includes an amino acid sequence having 70% or more sequence identity with amino acids 282-430 and/or 431-639 of the wild type *Marinitoga piezophila* argonaute (MpAgo) protein set forth in SEQ ID NO: 1. In some cases, a subject Ago polypeptide is the wild type MpAgo protein set forth in SEQ ID NO: 1. In some cases, a subject Ago polypeptide is a variant MpAgo polypeptide (e.g., a chimeric MpAgo polypeptide, a mutant MpAgo polypeptide, etc.). In some cases, a variant MpAgo polypeptide, compared to the wild type MpAgo protein set forth in SEQ ID NO: 1, comprises an amino acid sequence having one or more mutations and exhibits reduced nuclease activity. In some cases, a variant MpAgo polypeptide includes an amino acid sequence having a substitution or deletion in one or more amino acid positions selected from: D446, E482, D516, and N624 (e.g., D446A, E482A, D516A, and/or N624A) compared to the wild type MpAgo protein set forth in SEQ ID NO: 1.

In some embodiments, a subject method is a method of modifying a single stranded target nucleic acid, the Ago polypeptide has nuclease activity, and the method results in cleavage of the target nucleic acid. In some embodiments, a subject method is a method of modifying a single stranded target nucleic acid, where the Ago polypeptide is a chimeric MpAgo polypeptide having a fusion partner with an amino acid sequence that provides for a modification of the target nucleic acid other than cleavage (e.g., methylation, demethylation, polyadenylation, deadenylation, deamination, polyuridinylation, subcellular targeting, and the like). In some such cases, the subject Ago polypeptide is a mutant MpAgo polypeptide that, compared to the wild type MpAgo protein set forth in SEQ ID NO: 1, comprises an amino acid sequence having one or more mutations (e.g., D516A) and exhibits reduced nuclease activity.

In some embodiments, a subject method is a method of binding a single stranded target nucleic acid (e.g., a method that produces a mutant-Ago/target complex), where the subject Ago polypeptide is a mutant MpAgo polypeptide that, compared to the wild type MpAgo protein set forth in SEQ ID NO: 1, comprises an amino acid sequence having one or more mutations (e.g., D516A) and exhibits reduced nuclease activity. In some cases, such a method includes additional steps (e.g., (i) isolating the mutant-Ago/target complex; (ii) releasing the single stranded target nucleic acid from the mutant-Ago/target complex; and/or (iii) collecting and/or analyzing the released single stranded target nucleic acid and/or a polypeptide associated with the single stranded target nucleic acid). In some cases, the mutant MpAgo polypeptide and/or a guide RNA includes a detectable label.

In some embodiments, a subject recombinant expression vector includes nucleotide sequences that encode at least one of: (i) a subject Ago polypeptide (e.g., a wild type MpAgo polypeptide, a variant MpAgo, a mutant MpAgo, a chimeric MpAgo, and the like); and (ii) a subject precursor RNA. In some cases, a subject recombinant expression vector includes nucleotide sequences that encode a 5'-OH generating nuclease and at least one of: (i) a subject Ago polypeptide; and (ii) a subject precursor RNA. In some cases, a target cell already expresses a subject Ago polypeptide, and the method includes contacting the target nucleic acid (e.g., inside of a cell, outside of a cell, in vitro, in vivo, etc.) with at least one of: (i) a subject a guide RNA; and (ii) a 5'-OH generating nuclease. In some cases, a target cell already expresses a subject precursor RNA or already contains a subject guide RNA, and the method includes contacting the target nucleic acid with at least one of: (i) a subject Ago polypeptide; and (ii) a 5'-OH generating nuclease. In some embodiments, a subject recombinant expression vector includes a nucleotide sequence that encodes at least one of: a mutant MpAgo polypeptide; and a chimeric MpAgo polypeptide.

The present disclosure provides kits, where a subject kit includes at least one of: (i) a subject Ago polypeptide (e.g., a wild type MpAgo polypeptide, a variant MpAgo polypeptide), or a nucleic acid encoding the same; and (ii) a subject guide RNA, a subject precursor RNA, or a DNA polynucleotide encoding a subject precursor RNA. In some cases, a subject kit includes a 5'-OH generating nuclease or a nucleic acid encoding the same. In some cases, a subject kit includes a variant MpAgo polypeptide (e.g., a chimeric and/or mutant MpAgo polypeptide). In some cases, a subject kit includes one or more subject guide RNAs. In some cases, a subject kit includes one or more subject precursor RNAs (or DNA polynucleotides encoding the same).

The present disclosure provides genetically modified cells comprising a heterologous subject Ago polypeptide, and provides non-human transgenic organisms comprising one or more genetically modified cells.

BRIEF DESCRIPTION OF THE DRAWINGS

FIGS. 1A-E depict the association of an argonaute (Ago) protein with a CRISPR locus in *Marinitoga piezophila*; an amino acid sequence alignment of a portion of the CRISPR-associated *Marinitoga piezophila* Ago (MpAgo; "Marinitoga/1-639") (amino acids 423-639 of SEQ ID NO: 1) with argonaute proteins from other species (Human ("Homo/1-859"): amino acids 579-859 of SEQ ID NO:26; *Drosophila*/1-984: amino acids 703-984 of SEQ ID NO:27; *Thermus*/1-685: amino acids 461-685 of SEQ ID NO:28; and *Pyrococcus*/1-770: amino acids 541-770 of SEQ ID NO:29); and data showing the expression and cleavage activity of MpAgo.

FIGS. 3A-D depict an amino acid sequence alignment of a portion of the CRISPR-associated *Marinitoga piezophila* Ago (MpAgo) (amino acids 312-467 of SEQ ID NO: 1) with argonaute proteins from other species (Human/1-859: amino acids 453-619 of SEQ ID NO:26; *Drosophila*/1-984: amino acids 577-743 of SEQ ID NO:27; *Thermus*/1-685: amino acids 371-498 of SEQ ID NO:28; and *Pyrococcus*/1-770: SEQ ID NO:30); the corresponding crystal structure of the *Pyrococcus furiosus* Argonaute (PfAgo), and results from cleavage assays performed using variant MpAgo polypeptides.

DETAILED DESCRIPTION

Figure 1A:
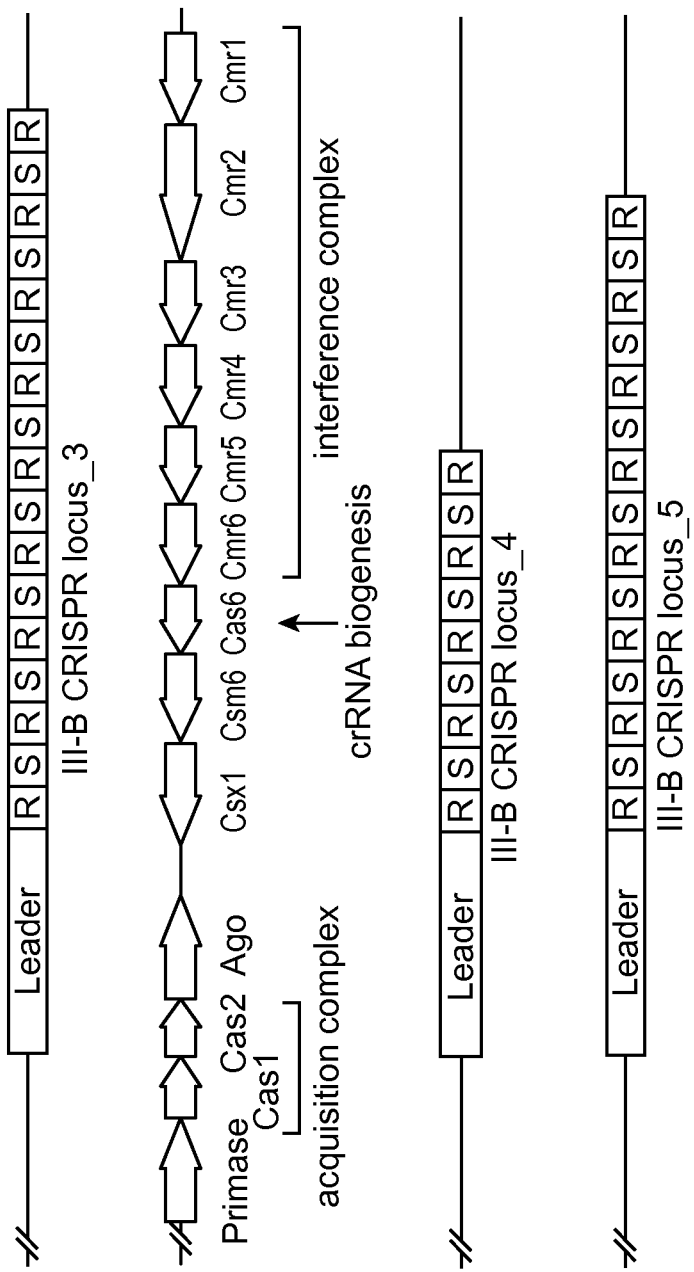

The present disclosure provides compositions, kits, genetically modified cells, non-human transgenic organisms, and methods for binding and/or cleaving a single stranded target nucleic acid. A method of cleaving includes contacting a single stranded target nucleic acid with (e.g., introducing into a cell) a subject argonaute (Ago) polypeptide and a guide RNA (e.g., having a 5'-OH). The target nucleic acid can be single stranded DNA (ssDNA) and/or single stranded RNA (ssRNA). The target nucleic acid can be inside of, or outside of a cell. For example, the subject methods can be performed outside of a cell in vitro, inside of a cell in vitro or ex vivo, and/or inside of a cell in vivo.

In some cases, contacting a target nucleic acid with a guide RNA includes introducing into a cell a precursor nucleic acid, where: (i) the precursor nucleic acid is a precursor RNA or a DNA polynucleotide encoding a precursor RNA, and (ii) the precursor RNA is modified, or is cleaved at a cleavage site, to generate the guide RNA. In some embodiments, a subject precursor RNA and a subject Ago polypeptide are both encoded by the same DNA polynucleotide.

In some embodiments, a subject Ago polypeptide includes an amino acid sequence having 70% or more sequence identity with amino acids 282-430 and/or 431-639 of the wild type *Marinitoga piezophila* argonaute (MpAgo) protein set forth in SEQ ID NO: 1. In some cases, a subject Ago polypeptide is the wild type MpAgo protein set forth in SEQ ID NO: 1. In some cases, a subject Ago polypeptide is a variant MpAgo polypeptide (e.g., a chimeric MpAgo polypeptide, a mutant MpAgo polypeptide, etc.). In some cases, a variant MpAgo polypeptide, compared to the wild type MpAgo protein set forth in SEQ ID NO: 1, comprises an amino acid sequence having one or more mutations and exhibits reduced nuclease activity. In some cases, a variant MpAgo polypeptide includes an amino acid sequence having a substitution or deletion in one or more amino acid positions selected from: D446, E482, D516, and N624 (e.g., D446A, E482A, D516A, and/or N624A) compared to the wild type MpAgo protein set forth in SEQ ID NO: 1.

In some embodiments, a subject method is a method of modifying a single stranded target nucleic acid, the Ago polypeptide has nuclease activity, and the method results in cleavage of the target nucleic acid. In some embodiments, a subject method is a method of modifying a single stranded target nucleic acid, where the Ago polypeptide is a chimeric MpAgo polypeptide having a fusion partner with an amino acid sequence that provides for a modification of the target nucleic acid other than cleavage. In some embodiments, a subject method is a method of binding a single stranded target nucleic acid, where the subject Ago polypeptide is a mutant MpAgo polypeptide that, compared to the wild type MpAgo protein set forth in SEQ ID NO: 1, comprises an amino acid sequence having one or more mutations (e.g., D516A) and exhibits reduced nuclease activity. In some cases, such a method includes additional steps (e.g., (i) isolating a mutant-Ago/target complex; (ii) releasing the single stranded target nucleic acid from the mutant-Ago/target complex; and/or (iii) collecting and/or analyzing the released single stranded target nucleic acid and/or a polypeptide associated with the single stranded target nucleic acid). In some cases, a mutant MpAgo polypeptide and/or a guide RNA includes a detectable label.

In some embodiments, a subject recombinant expression vector includes nucleotide sequences that encode at least one of: (i) a subject Ago polypeptide (e.g., a wild type MpAgo polypeptide, a variant MpAgo, a mutant MpAgo, a chimeric MpAgo, and the like); and (ii) a subject precursor RNA. In some embodiments, a subject recombinant expression vector includes a nucleotide sequence that encodes at least one of: a mutant MpAgo polypeptide; and a chimeric MpAgo polypeptide.

The present disclosure provides kits, where a subject kit includes at least one of: (i) a subject Ago polypeptide (e.g., a wild type MpAgo polypeptide, a variant MpAgo polypeptide), or a nucleic acid encoding the same; and (ii) a subject guide RNA, a subject precursor RNA, or a DNA polynucleotide encoding a subject precursor RNA. In some cases, a subject kit includes one or more subject guide RNAs. In some cases, a subject kit includes one or more subject precursor RNAs (or DNA polynucleotides encoding the same). The present disclosure also provides genetically modified cells having a heterologous subject Ago polypeptide, and provides non-human transgenic organisms having one or more genetically modified cells.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "oligonucleotide" refers to a polynucleotide of between 3 and 100 nucleotides of single- or double-stranded nucleic acid (e.g., DNA, RNA, or a modified nucleic acid). However, for the purposes of this disclosure, there is no upper limit to the length of an oligonucleotide. Oligonucleotides are also known as "oligomers" or "oligos" and may be isolated from genes, transcribed (in vitro and/or in vivo), or chemically synthesized. The terms "polynucleotide" and "nucleic acid" should be understood to include, as applicable to the embodiments being described, single-stranded (such as sense or antisense) and double-stranded polynucleotides.

By "hybridizable" or "complementary" or "substantially complementary" it is meant that a nucleic acid (e.g. RNA, DNA) comprises a sequence of nucleotides that enables it to non-covalently bind, i.e. form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. Standard Watson-Crick base-pairing includes: adenine (A) pairing with thymidine (T), adenine (A) pairing with uracil (U), and guanine (G) pairing with cytosine (C) [DNA, RNA]. In addition, for hybridization between two RNA molecules (e.g., dsRNA), and for hybridization of a DNA molecule with an RNA molecule (e.g., when a ssDNA target nucleic acid base pairs with a guide RNA) guanine (G) can also base pair with uracil (U). For example, G/U base-pairing is partially responsible for the degeneracy (i.e., redundancy) of the genetic code in the context of tRNA anti-codon base-pairing with codons in mRNA. Thus, in the context of this disclosure, a guanine (G) (e.g., of a target nucleic acid base pairing with a guide RNA) is considered complementary to both a uracil (U) and to an adenine (A). For example, when a G/U base-pair can be made at a given nucleotide position, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementarity, variables well known in the art. The greater the degree of complementarity between two nucleotide sequences, the greater the value of the melting temperature (Tm) for hybrids of nucleic acids having those sequences. For hybridizations between nucleic acids with short stretches of complementarity (e.g. complementarity over 35 or less, 30 or less, 25 or less, 22 or less, 20 or less, or 18 or less nucleotides) the position of mismatches can become important (see Sambrook et al., supra, 11.7-11.8). Typically, the length for a hybridizable nucleic acid is 8 nucleotides or more (e.g., 10 nucleotides or more, 12 nucleotides or more, 15 nucleotides or more, 20 nucleotides or more, 22 nucleotides or more, 25 nucleotides or more, or 30 nucleotides or more). The temperature and wash solution salt concentration may be adjusted as necessary according to factors such as length of the region of complementation and the degree of complementation (i.e., degree of complementarity).

It is understood that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). For example, a polynucleotide can comprise 60% or more, 65% or more, 70% or more, 75% or more, 80% or more, 85% or more, 90% or more, 95% or more, 98% or more, 99% or more, 99.5% or more, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Exemplary methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g. with reference to a guide RNA binding a subject Ago polypeptide, binding to a target nucleic acid, and the like) refers to a non-covalent interaction between macromolecules (e.g., between a protein and a nucleic acid; between a subject Ago polypeptide/guide RNA complex and a target nucleic acid; and the like). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence-specific. Binding interactions are generally characterized by a dissociation constant (Kd) of less than $10^{-6}$ M, less than $10^{-7}$ M, less than $10^{-8}$ M, less than $10^{-9}$ M, less than $10^{-10}$ M, less than $10^{-11}$ M, less than $10^{-12}$ M, less than $10^{-13}$ M, less than $10^{-14}$ M, or less than $10^{-15}$ M. "Affinity" refers to the strength of binding, increased binding affinity being correlated with a lower Kd.

By "binding domain" it is meant a protein domain that is able to bind non-covalently to another molecule. A binding domain can bind to, for example, a DNA molecule (a DNA-binding domain), an RNA molecule (an RNA-binding domain) and/or a protein molecule (a protein-binding domain). In the case of a protein having a protein-binding domain, it can in some cases bind to itself (to form homodimers, homotrimers, etc.) and/or it can bind to one or more regions of a different protein or proteins.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence identity can be determined in a number of different ways. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST, ebi.ac.uk/Tools/msa/tcoffee/, ebi.ac.uk/Tools/msa/muscle/, mafft.cbrc.jp/alignment/software/. See, e.g., Altschul et al. (1990), J. Mol. Bioi. 215:403-10.

A DNA sequence that "encodes" a particular RNA is a DNA nucleic acid sequence that is transcribed into RNA. A DNA polynucleotide may encode an RNA (mRNA) that is translated into protein, or a DNA polynucleotide may encode an RNA that is not translated into protein (e.g. tRNA, rRNA, microRNA (miRNA), a "non-coding" RNA (ncRNA), a guide nucleic acid, etc.).

A "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from prokaryotic or eukaryotic mRNA, genomic DNA sequences from prokaryotic or eukaryotic DNA, and synthetic nucleic acids. A transcription termination sequence will usually be located 3' to the coding sequence.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate transcription of a non-coding sequence (e.g., guide nucleic acid) or a coding sequence (e.g., a subject Ago polypeptide) and/or regulate translation of an encoded polypeptide.

As used herein, a "promoter sequence" is a DNA regulatory region capable of binding RNA polymerase and initiating transcription of a downstream (3' direction) coding or non-coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

The term "naturally-occurring" or "unmodified" or "wild type" as used herein as applied to a nucleic acid, a polypeptide, a cell, or an organism, refers to a nucleic acid, polypeptide, cell, or organism that is found in nature. For example, a polypeptide or polynucleotide sequence that is present in an organism (including viruses) that can be isolated from a source in nature and which has not been intentionally modified by a human in the laboratory is wild type (and naturally occurring).

The term "chimeric" as used herein as applied to a nucleic acid or polypeptide refers to two components that are defined by structures derived from different sources. For example, where "chimeric" is used in the context of a chimeric polypeptide (e.g., a chimeric MpAgo polypeptide), the chimeric polypeptide includes amino acid sequences that are derived from different polypeptides. A chimeric polypeptide may comprise either modified or naturally-occurring polypeptide sequences (e.g., a first amino acid sequence from a modified (e.g., mutant) or unmodified (e.g., wild type) MpAgo polypeptide; and a second amino acid sequence from a protein other than the MpAgo protein). Similarly, "chimeric" in the context of a polynucleotide encoding a chimeric polypeptide includes nucleotide sequences derived from different coding regions (e.g., a first nucleotide sequence encoding a modified (e.g., mutant) or unmodified (e.g., wild type) MpAgo polypeptide; and a second nucleotide sequence encoding a polypeptide from a protein other than the MpAgo protein).

The term "chimeric polypeptide" refers to a polypeptide which is made by the combination (i.e., "fusion") of two otherwise separated segments of amino sequence, usually through human intervention. A polypeptide that comprises a chimeric amino acid sequence is a chimeric polypeptide. Some chimeric polypeptides can be referred to as "fusion variants."

"Heterologous," as used herein, means a nucleotide or polypeptide sequence that is not found in the native nucleic acid or protein, respectively. For example, in a chimeric MpAgo protein, the guide RNA-binding domain (e.g., MID domain) of a subject MpAgo polypeptide (or a variant thereof) may be fused to a heterologous polypeptide sequence (i.e. a polypeptide sequence from a protein other than MpAgo). The heterologous polypeptide sequence may exhibit an activity (e.g., enzymatic activity) that will also be exhibited by the chimeric MpAgo protein (e.g., methyltransferase activity, acetyltransferase activity, kinase activity, ubiquitinating activity, etc.). A heterologous nucleic acid sequence may be linked to a naturally-occurring nucleic acid sequence (or a variant thereof) (e.g., by genetic engineering) to generate a chimeric nucleotide sequence encoding a chimeric polypeptide. As another example, in a fusion variant MpAgo polypeptide, a variant (e.g., mutant) MpAgo polypeptide may be fused to a heterologous polypeptide (i.e. a polypeptide other than MpAgo), which exhibits an activity that will also be exhibited by the fusion variant MpAgo polypeptide. A heterologous nucleic acid sequence may be linked to a variant MpAgo polypeptide (e.g., by genetic engineering) to generate a nucleotide sequence encoding a fusion variant polypeptide.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below). Alternatively, DNA sequences encoding RNA (e.g., guide nucleic acid) that is not translated may also be considered recombinant. Thus, e.g., the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e. an "insert", may be attached so as to bring about the replication of the attached segment in a cell.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

A cell has been "genetically modified" or "transformed" or "transfected" by exogenous DNA, e.g. a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

Suitable methods of genetic modification (also referred to as "transformation") include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al. Adv Drug Deliv. Rev. 2012 Sep. 13. pii: S0169-409X(12)00283-9. doi: 10.1016/j.addr.2012.09.023), and the like.

The choice of method of genetic modification is generally dependent on the type of cell being transformed and the circumstances under which the transformation is taking place (e.g., in vitro, ex vivo, or in vivo). A general discussion of these methods can be found in Ausubel, et al., Short Protocols in Molecular Biology, 3rd ed., Wiley & Sons, 1995.

A "target nucleic acid" as used herein is a polynucleotide (e.g., RNA, DNA) that includes a "target site" or "target sequence." The terms "target site" or "target sequence" are used interchangeably herein to refer to a nucleic acid sequence present in a target nucleic acid to which a targeting sequence of a subject guide RNA will hybridize, provided sufficient conditions for hybridization exist. For example, the target site (or target sequence) 5'-GAGCAUAUC-3' within a target nucleic acid is targeted by (or is bound by, or hybridizes with, or is complementary to) the sequence 5'-GAUAUGCUC-3'. Suitable hybridization conditions include physiological conditions normally present in a cell. In cases where the target nucleic acid is a single stranded target nucleic acid (e.g., single stranded DNA (ssDNA), single stranded RNA (ssRNA)), the guide RNA is complementary to and hybridizes with a target sequence of the single stranded target nucleic acid.

By "cleavage" it is meant the breakage of the covalent backbone of a target nucleic acid molecule (e.g., RNA, DNA). Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events (e.g., dsDNA can be melted prior to cleavage, and each strand can be cleaved). In certain embodiments, a complex including a guide RNA and a subject Ago polypeptide is used for targeted cleavage of a single stranded target nucleic acid (e.g., ssRNA, ssDNA).

"Nuclease" and "endonuclease" are used interchangeably herein to mean an enzyme which possesses catalytic activity for nucleic acid cleavage (e.g., ribonuclease activity (ribonucleic acid cleavage), deoxyribonuclease activity (deoxyribonucleic acid cleavage), etc.).

By "cleavage domain" or "active domain" or "nuclease domain" of a nuclease it is meant the polypeptide sequence or domain within the nuclease which possesses the catalytic activity for nucleic acid cleavage. A cleavage domain can be contained in a single polypeptide chain or cleavage activity can result from the association of two (or more) polypeptides. A single nuclease domain may consist of more than one isolated stretch of amino acids within a given polypeptide (e.g., amino acids that make up a nuclease domain may be separated in the primary amino acid sequence, but located near each other in a biological context (e.g., when the polypeptide is folded into a three-dimensional protein).

A nucleic acid molecule that binds to a subject Ago polypeptide and targets the polypeptide to a specific location within the target nucleic acid is referred to herein as a "guide nucleic acid" or "guide RNA." In some cases, a subject guide nucleic acid includes a 5'-OH (5'-hydroxyl) instead of a standard 5'-phosphate (5'-PO$_4$). A guide RNA can be derived from a precursor RNA (via modification or cleavage).

A "precursor RNA" as used herein is an RNA that can be modified or cleaved to produce a guide RNA. A precursor RNA can have a 5'-phosphate or a 5'-OH. For example, in some cases, a precursor RNA having a 5'-phosphate is cleaved to generate a guide RNA (e.g., having a 5'-OH) as a product of the cleavage reaction. In some cases, a precursor RNA having a 5'-phosphate is modified such that the 5'-phosphate is converted into a 5'-OH.

A "host cell" or "target cell" as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

PSCs of animals can be derived in a number of different ways. For example, embryonic stem cells (ESCs) are derived from the inner cell mass of an embryo (Thomson et. al, Science. 1998 Nov. 6; 282(5391):1145-7) whereas induced pluripotent stem cells (iPSCs) are derived from somatic cells (Takahashi et. al, Cell. 2007 Nov. 30; 131(5): 861-72; Takahashi et. al, Nat Protoc. 2007; 2(12):3081-9; Yu et. al, Science. 2007 Dec. 21; 318(5858):1917-20. Epub 2007 Nov. 20). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein.

By "embryonic stem cell" (ESC) is meant a PSC that was isolated from an embryo, typically from the inner cell mass of the blastocyst. ESC lines are listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Stem cells of interest also include embryonic stem cells from other primates, such as Rhesus stem cells and marmoset stem cells. The stem cells may be obtained from any mammalian species, e.g. human, equine, bovine, porcine, canine, feline, rodent, e.g. mice, rats, hamster, primate, etc. (Thomson et al. (1998) Science 282:1145; Thomson et al. (1995) Proc. Natl. Acad. Sci USA 92:7844; Thomson et al. (1996) Biol. Reprod. 55:254; Shamblott et al., Proc. Natl. Acad. Sci. USA 95:13726, 1998). In culture, ESCs typically grow as flat colonies with large nucleo-cytoplasmic ratios, defined borders and prominent nucleoli. In addition, ESCs express SSEA-3, SSEA-4, TRA-1-60, TRA-1-81, and Alkaline Phosphatase, but not SSEA-1. Examples of methods of generating and characterizing ESCs may be found in, for example, U.S. Pat. No. 7,029,913, U.S. Pat. No. 5,843,780, and U.S. Pat. No. 6,200,806, the disclosures of which are incorporated herein by reference. Methods for proliferating hESCs in the undifferentiated form are described in WO 99/20741, WO 01/51616, and WO 03/020920.

By "embryonic germ stem cell" (EGSC) or "embryonic germ cell" or "EG cell" is meant a PSC that is derived from germ cells and/or germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646, the disclosures of which are incorporated herein by reference. Generally, to generate iPSCs, somatic cells are provided with reprogramming factors (e.g. Oct4, SOX2, KLF4, MYC, Nanog, Lin28, etc.) known in the art to reprogram the somatic cells to become pluripotent stem cells.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e. ectoderm, mesoderm and endoderm. For example, somatic cells would include both neurons and neural progenitors, the latter of which may be able to naturally give rise to all or some cell types of the central nervous system but cannot give rise to cells of the mesoderm or endoderm lineages.

By "mitotic cell" it is meant a cell undergoing mitosis. Mitosis is the process by which a eukaryotic cell separates the chromosomes in its nucleus into two identical sets in two separate nuclei. It is generally followed immediately by cytokinesis, which divides the nuclei, cytoplasm, organelles and cell membrane into two cells containing roughly equal shares of these cellular components.

By "post-mitotic cell" it is meant a cell that has exited from mitosis, i.e., it is "quiescent", i.e. it is no longer undergoing divisions. This quiescent state may be temporary, i.e. reversible, or it may be permanent.

By "meiotic cell" it is meant a cell that is undergoing meiosis. Meiosis is the process by which a cell divides its nuclear material for the purpose of producing gametes or spores. Unlike mitosis, in meiosis, the chromosomes undergo a recombination step which shuffles genetic material between chromosomes. Additionally, the outcome of meiosis is four (genetically unique) haploid cells, as compared with the two (genetically identical) diploid cells produced from mitosis.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease or symptom in a mammal, and includes: (a) preventing the disease or symptom from occurring in a subject which may be predisposed to acquiring the disease or symptom but has not yet been diagnosed as having it; (b) inhibiting the disease or symptom, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired. Individuals include murines (e.g., rats; mice); lagomorphs (e.g., rabbits), ovines, bovines, caprines, canines, felines, non-human primates, and primates.

In some instances, a component (e.g., a nucleic acid component (e.g., a guide RNA); a protein component (e.g., a subject Ago polypeptide); and the like) includes a label moiety. The terms "label", "detectable label", or "label moiety" as used herein refer to any moiety that provides for signal detection and may vary widely depending on the particular nature of the assay. Label moieties of interest include both directly detectable labels (direct labels)(e.g., a fluorescent label) and indirectly detectable labels (indirect labels)(e.g., a binding pair member). A fluorescent label can be any fluorescent label (e.g., a fluorescent dye (e.g., fluorescein, Texas red, rhodamine, ALEXAFLUOR® labels, and the like), a fluorescent protein (e.g., GFP, EGFP, YFP, RFP, CFP, YFP, cherry, tomato, tangerine, and any fluorescent derivative thereof), etc.). Suitable detectable (directly or indirectly) label moieties for use in the methods include any moiety that is detectable by spectroscopic, photochemical, biochemical, immunochemical, electrical, optical, chemical, or other means. For example, suitable indirect labels include biotin (a binding pair member), which can be bound by streptavidin (which can itself be directly or indirectly labeled). Labels can also include: a radiolabel (a direct label)(e.g., $^3$H, $^{125}$I, $^{35}$S, $^{14}$C, or $^{32}$P); an enzyme (an indirect label)(e.g., peroxidase, alkaline phosphatase, galactosidase, luciferase, glucose oxidase, and the like); a fluorescent protein (a direct label)(e.g., green fluorescent protein, red fluorescent protein, yellow fluorescent protein, and any convenient derivatives thereof); a metal label (a direct label); a colorimetric label; a binding pair member; and the like. By "partner of a binding pair" or "binding pair member" is meant one of a first and a second moiety, wherein the first and the second moiety have a specific binding affinity for each other. Suitable binding pairs include, but are not limited to: antigen/antibodies (for example, digoxigenin/anti-digoxigenin, dinitrophenyl (DNP)/anti-DNP, dansyl-X-anti-dansyl, fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Any binding pair member can be suitable for use as an indirectly detectable label moiety.

Any given component, or combination of components can be unlabeled, or can be detectably labeled with a label moiety. In some cases, when two or more components are labeled, they can be labeled with label moieties that are distinguishable from one another.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Compositions and Components

The present disclosure provides compositions for binding and/or cleaving a single stranded target nucleic acid. A composition for cleaving includes a subject guide RNA and a subject Ago polypeptide.

Guide RNA

The present disclosure provides a guide RNA (i.e., "gRNA") that associates with (i.e., binds to) and directs the activities of a subject Ago polypeptide to a specific target sequence within a target nucleic acid by virtue of hybridization to a target site of the target nucleic acid. In some cases, a subject guide nucleic acid includes a 5'-OH (5'-hydroxyl) instead of a standard 5'-phosphate (5'-PO$_4$). In some cases, a subject guide nucleic acid includes a 5'-phosphate (5'-PO$_4$). A guide RNA can be derived from a precursor RNA (via modification or cleavage). In some cases, a guide RNA is a targeting sequence with a 5'-OH. In some cases, a guide RNA includes sequences in addition to the targeting sequence (see below). Thus, the length of a guide RNA is determined by the length of the targeting sequence plus the length of any additional sequences.

Targeting Sequence

A targeting sequence of a guide RNA is a nucleotide sequence that is complementary to a sequence (a target site, a target sequence) of a target nucleic acid. A targeting sequence of a guide RNA can have a length of 15 nt or more. For example, the targeting sequence of a guide RNA can have a length of 12 nt or more, 15 nt or more, 18 nt or more, 19 nt or more, 20 nt or more, 25 nt or more, 30 nt or more, 35 nt or more or 40 nt. In some cases, the targeting sequence of a guide RNA can have a length of from 12 nucleotides (nt) to 80 nt (e.g., from 12 nt to 50 nt, from 12 nt to 45 nt, from 12 nt to 40 nt, from 12 nt to 35 nt, from 12 nt to 30 nt, from 12 nt to 25 nt, from 12 nt to 21 nt, from 15 nt to 50 nt, from 15 nt to 45 nt, from 15 nt to 40 nt, from 15 nt to 35 nt, from 15 nt to 30 nt, from 15 nt to 25 nt, from 15 nt to 21 nt, from 18 nt to 50 nt, from 18 nt to 45 nt, from 18 nt to 40 nt, from 18 nt to 35 nt, from 18 nt to 30 nt, from 18 nt to 25 nt, from 18 nt to 21 nt, from 19 nt to 50 nt, from 19 nt to 45 nt, from 19 nt to 40 nt, from 19 nt to 35 nt, from 19 nt to 30 nt, from 19 nt to 25 nt, from 19 nt to 22 nt, or from 19 nt to 21 nt). In some cases, the targeting sequence of a guide RNA is 18 to 25 nucleotides in length. In some cases, the targeting sequence of a guide RNA is 21 nucleotides in length.

The percent complementarity between the targeting sequence of a guide RNA and the target site (i.e., target sequence) of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of a guide RNA and the target site (i.e., target sequence) of the target nucleic acid is 100%. The percent complementarity between the targeting sequence of a guide RNA and the target site (i.e., target sequence) of the target nucleic acid can be 60% or more (e.g., 65% or more, 70% or more, 75% or more, 80% or more, 85% or more, 90% or more, 95% or more, 97% or more, 98% or more, 99% or more, or 100%) over 15 or more contiguous nucleotides (e.g., 16 or more, 17 or more, 18 or more, 19 or more, 20 or more, or 21 or more) of the target site. In some cases, the percent complementarity between the targeting sequence of a guide RNA and the target site (i.e., target sequence) of the target nucleic acid is 100% over 15 or more contiguous nucleotides (e.g., 16 or more, 17 or more, 18 or more, 19 or more, 20 or more, or 21 or more) of the target site.

Precursor RNA

A "precursor RNA" as used herein is an RNA that can be modified and/or cleaved to produce a guide RNA. A precursor RNA therefore includes that targeting sequence of the eventual guide RNA that will be produced. A precursor RNA can have a 5'-phosphate or a 5'-OH. For example, in some cases, a precursor RNA having a 5'-phosphate is cleaved to generate a guide RNA (e.g., having a 5'-OH) as a product of the cleavage reaction (e.g., a sequence specific cleavage reaction). In some cases, a precursor RNA having a 5'-phosphate is modified such that the 5'-phosphate is converted into a 5'-OH.

In some cases, a cleavage site is positioned 5' of the targeting sequence (i.e., the targeting sequence is positioned 3' of the cleavage site) such that cleavage at the cleavage site results in the production of a 5'-OH, which will be the 5'-OH of the guide RNA. Such a cleavage site can be cleaved by a ribozyme and/or 5'-OH generating nuclease. In some cases, a cleavage site is positioned 5' of the targeting sequence (i.e., the targeting sequence is positioned 3' of the cleavage site) such that cleavage at the cleavage site results in the production of a 5'-phosphate, which will be the 5'-phosphate of the guide RNA. In some cases, a precursor RNA can have a cleavage site positioned 3' of the targeting sequence. For example, a precursor RNA can be cleaved to generate the 3' end of a guide RNA. In some cases, a precursor RNA can include a stability control sequence or other additional sequence (described below, e.g., one that provides for subcellular localization, one that provides for stability, etc.) that is cleaved from the precursor RNA during production of the guide RNA. When a cleavage site is positioned 3' of the targeting sequence, cleavage can, but does not necessarily have to result in a 5'-OH at the site of cleavage. In some cases, a precursor RNA has a cleave site positioned 5' of the targeting sequence and a cleavage site positioned 3' of the targeting sequence. In some such cases, cleavage at both cleavage sites defines the boundaries (the length) of the produced guide RNA. Thus, in some cases, a subject precursor RNA has at least one of: a cleavage site positioned 5' of the targeting sequence (e.g., a cleavage site that can be cleaved by a ribozyme or by a 5'-OH generating nuclease); and a cleavage site positioned 3' of the targeting sequence. When a precursor RNA has a first cleavage site positioned 5' of the targeting sequence and a second cleavage site positioned 3' of the targeting sequence, the two cleavage sites can be different (i.e., can be recognized and cleaved by different ribozymes and/or nucleases), or they can be the same (e.g., recognized by the same ribozyme or nuclease).

In some cases, a precursor RNA includes a self-cleaving sequence. If the self-cleaving sequence recognizes a cleavage site that is 5' of the targeting sequence, then the self-cleaving sequence can be one that generates a 5'-OH or one that generates a 5'-phosphate. A precursor RNA can have any convenient self-cleaving sequence (e.g., one that generates a 5'-OH or one that generates a 5'-phosphate). Suitable self-cleaving sequences include, but are not limited to: a hammerhead ribozyme; small Tobacco RingSpot Virus hammerhead ribozyme (sTRSV); Avacado SunBlotch Virus ribozyme (ASBV); beta-globin co-transcriptional ribozyme; bacterial group II introns; glucosamine-6-phosphate ribozyme; group I/II/III introns; hepatitis delta virus ribozyme; CPEB3 ribozyme; VS ribozyme; the group of hairpin ribozymes such as chicory yellow mottle virus ribozyme and arabis mosaic virus ribozyme; the group of hammerhead ribozymes such as eggplant viroid ribozyme, velvet tobacco mottle virus ribozyme, and cherry small circular viroid-like ribozyme.

In some cases, a precursor RNA (e.g., one that includes a self-cleaving sequence) is already present in a cell, and the step of contacting the target nucleic acid with a guide RNA is performed by stimulating the cleavage of the precursor RNA. For example, stimulating the cleavage of the precursor RNA can be performed by activating a self-cleaving sequence of the precursor RNA (e.g., by providing a compound that activates the self-cleaving sequence), or by activating (or otherwise providing an active form of) a 5'-OH generating nuclease (or a 5'-phosphate generating nuclease).

If a 5'-OH generating nuclease is to be used, any convenient 5'-OH can be suitable. Exemplary 5'-OH generating nucleases include but are not limited to CRISPR (clustered regularly interspaced short palindromic repeats)-associated nucleases (which are known in the art to generate 5'-OH RNA products). For example, suitable CRISPR-associated nucleases include, but are not limited to csy4, cas6, and cas5, which are described, along with their target cleavage sequences, in patent applications: WO2011143124, WO2013188638, and US20110223638; all of which are hereby incorporated by reference in their entirety.

In some embodiments, a cleavage site of a precursor RNA is immediately adjacent to the targeting sequence. In some embodiments, the number of nucleotides (nt) present in the precursor RNA between a cleavage site and the 5' or 3' end of the targeting sequence of the precursor RNA is in a range of from 0 nt to 10 nt (e.g., 0 nt to 9 nt, 0 nt to 8 nt, 0 nt to 7 nt, 0 nt to 6 nt, 0 nt to 5 nt, 0 nt to 4 nt, 0 nt to 3 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 9 nt, 2 nt to 8 nt, 2 nt to 7 nt, 2 nt to 6 nt, 2 nt to 5 nt, 2 nt to 4 nt, or 2 nt to 3 nt). In some embodiments, 10 or less nt (e.g., 9 or less nt, 8 or less nt, 7 or less nt, 6 or less nt, 5 or less nt, 4 or less nt, 3 or less nt, 2 or less nt, 1 or less nt, or no nt) are present in the precursor RNA between a cleavage site and the 5' or 3' end of the targeting sequence. In some embodiments, the number of nucleotides (nt) present in the precursor RNA between a cleavage site and the 5' or 3' end of the targeting sequence is in a range of from 0 nt to 10 nt (e.g., 0 nt to 9 nt, 0 nt to 8 nt, 0 nt to 7 nt, 0 nt to 6 nt, 0 nt to 5 nt, 0 nt to 4 nt, 0 nt to 3 nt, 1 nt to 9 nt, 1 nt to 8 nt, 1 nt to 7 nt, 1 nt to 6 nt, 1 nt to 5 nt, 1 nt to 4 nt, 1 nt to 3 nt, 2 nt to 9 nt, 2 nt to 8 nt, 2 nt to 7 nt, 2 nt to 6 nt, 2 nt to 5 nt, 2 nt to 4 nt, or 2 nt to 3 nt). In some embodiments, 10 or less nt (e.g., 9 or less nt, 8 or less nt, 7 or less nt, 6 or less nt, 5 or less nt, 4 or less nt, 3 or less nt, 2 or less nt, 1 or less nt, or no nt) are present in the precursor RNA between a cleavage site and the 5' or 3' end of the targeting sequence.

A precursor RNA can be any convenient length. In some embodiments, a precursor RNA has a length in a range of from 15 nt to 10,000 nt (e.g., 15 nt to 5,000 nt, 15 nt to 2,000 nt, 15 nt to 1,000 nt, 15 nt to 500 nt, 15 nt to 300 nt, 15 nt to 200 nt, 15 nt to 100 nt, 15 nt to 75 nt, 15 nt to 50 nt, 15 nt to 40 nt, 15 nt to 35 nt, 15 nt to 30 nt, 18 nt to 5,000 nt, 18 nt to 2,000 nt, 18 nt to 1,000 nt, 18 nt to 500 nt, 18 nt to 300 nt, 18 nt to 200 nt, 18 nt to 100 nt, 18 nt to 75 nt, 18 nt to 50 nt, 18 nt to 40 nt, 18 nt to 35 nt, 18 nt to 30 nt, 20 nt to 5,000 nt, 20 nt to 2,000 nt, 20 nt to 1,000 nt, 20 nt to 500 nt, 20 nt to 300 nt, 20 nt to 200 nt, 20 nt to 100 nt, 20 nt to 75 nt, 20 nt to 50 nt, 20 nt to 40 nt, 20 nt to 35 nt, or 20 nt to 30 nt). For example, in some cases, a precursor RNA can be a coding RNA (e.g., an mRNA). In some cases, the targeting sequence of the precursor RNA can include 5'-UTR, 3'-UTR, and or intron sequences. In some cases, a cleavage site (or cleavage sites) can be positioned within an mRNA such that cleavage at the cleavage site (or cleavage sites) produces a subject guide RNA.

Stability Control Sequence

In some embodiments, a guide RNA and/or a precursor RNA comprises a stability control sequence. A stability control sequence influences the stability of a nucleic acid (e.g., a guide RNA, a precursor RNA, etc.). One example of a suitable stability control sequence for use with an RNA is a transcriptional terminator segment (i.e., a transcription termination sequence). A transcriptional terminator segment of a subject guide RNA and/or a precursor RNA can have a total length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the transcriptional terminator segment can have a length of from about 15 nucleotides (nt) to about 80 nt, from about 15 nt to about 50 nt, from about 15 nt to about 40 nt, from about 15 nt to about 30 nt or from about 15 nt to about 25 nt.

In some cases, the transcription termination sequence is one that is functional in a eukaryotic cell. In some cases, the transcription termination sequence is one that is functional in a prokaryotic cell. One non-limiting examples of a nucleotide sequence that can be included in a stability control sequence (e.g., of a guide RNA and/or a precursor RNA to provide for increased stability), is: 5'-UAAUC-CCACAGCCGCCAGUUCCGCUGGCGGCAUUUU-5' (SEQ ID NO: 10) (a Rho-independent trp termination site). Additional stability control sequences are disclosed in patent application WO2013176772, which is hereby incorporated by reference in its entirety.

Additional Sequences

In some embodiments, a guide RNA and/or a precursor RNA comprises an additional segment or segments (in some cases at the 5' end, in some cases the 3' end, in some cases at either the 5' or 3' end, in some cases embedded within the sequence (i.e., not at the 5' and/or 3' end), in some cases at both the 5' end and the 3' end, in some cases embedded and at the 5' end and/or the 3' end, etc). For example, a suitable additional segment (e.g., of a precursor RNA) can comprise a 5' cap (e.g., a 7-methylguanylate cap ($m^7G$)); a 3' polyadenylated tail (i.e., a 3' poly(A) tail); a ribozyme sequence (e.g. to allow for self-cleavage of a precursor RNA); a riboswitch sequence (e.g., to allow for regulated stability and/or regulated accessibility by proteins and protein complexes); a sequence that forms a dsRNA duplex (i.e., a hairpin)); a sequence that targets an RNA to a subcellular location (e.g., nucleus, mitochondria, chloroplasts, and the like); a modification or sequence that provides for tracking (e.g., a direct label (e.g., direct conjugation to a fluorescent molecule (i.e., fluorescent dye)), conjugation to a moiety that facilitates fluorescent detection, a sequence that allows for fluorescent detection; a modification or sequence that provides a binding site for proteins (e.g., proteins that act on DNA, including transcriptional activators, transcriptional repressors, DNA methyltransferases, DNA demethylases, histone acetyltransferases, histone deacetylases, proteins that bind RNA (e.g., RNA aptemers), labeled proteins, fluorescently labeled proteins, proteins that aid in the loading, e.g., binding, of a subject Ago polypeptide with the guide RNA, and the like); a modification or sequence that provides for increased, decreased, and/or controllable stability; and combinations thereof.

Argonaute (Ago) Polypeptides

A subject Ago polypeptide forms a complex with a subject guide RNA. The guide RNA provides target specificity to the complex by comprising a nucleotide sequence (a targeting sequence) that is complementary to a sequence (the target site, the target sequence) of a target nucleic acid (as noted above). The Ago polypeptide of the complex provides site-specific activity. In other words, the Ago polypeptide is guided to a target site within a single stranded target nucleic acid sequence (e.g. a single stranded region of a double stranded nucleic acid, a chromosomal sequence or an extra-chromosomal sequence, e.g. an episomal sequence, a mini-circle sequence, a mitochondrial sequence, a chloroplast sequence, an ssRNA, an ssDNA, etc.) by virtue of its association with the guide RNA (described above).

A subject Ago polypeptide can bind and/or modify (e.g., cleave, methylate, demethylate, etc.) a target nucleic acid and/or a polypeptide associated with target nucleic acid. As described in further detail below, in some cases, a subject Ago polypeptide has enzymatic activity that modifies target nucleic acid (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity). In other cases, a subject Ago polypeptide has enzymatic activity that modifies a polypeptide (e.g., a histone, a single stranded binding protein, etc.) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

In some cases, a subject Ago polypeptide is a naturally-occurring polypeptide (e.g, naturally occurs in bacterial and/or archaeal cells). In other cases, a subject Ago polypeptide is not a naturally-occurring polypeptide (e.g., the subject Ago polypeptide is a variant MpAgo polypeptide, e.g, a chimeric MpAgo polypeptide, a mutant MpAgo polypeptide, as discussed below). In some cases, a subject Ago polypeptide has nuclease activity (e.g., nuclease activity comparable to that exhibited by the wild type MpAgo protein having the amino acid sequence set forth in SEQ ID NO: 1). In some cases, a subject Ago polypeptide has reduced nuclease activity compared to the wild type MpAgo protein having the amino acid sequence set forth in SEQ ID NO: 1.

Assays to determine nuclease activity include assays that cleave a single stranded target nucleic acid and can be any convenient nucleic acid cleavage assay that tests for nucleic acid cleavage of a target single stranded nucleic acid. Exemplary cleavage assays are shown in FIG. 1, FIG. 2, FIG. 3, and FIG. 4 and include cleavage assays that include contacting a target single stranded nucleic acid with a guide RNA and a subject Ago polypeptide, and detecting the presence or absence of a cleavage product.

The amino acid sequence of the wild type *Marinitoga piezophila* argonaute (MpAgo) protein referred to herein is:

```
                                          (SEQ ID NO: 1)
MYLNLYKIDIPKKIKRLYFYNPDMEPKLFARNLSRVNNFKFQDSNDLVWI

EIPDIDFQITPKNVFQYKVEKEEIIKEEEDKKLFVKTLYKYIKKLFLDND

FYFKKGNNFISNSEVFSLDSNENVNAHLTYKIKIHNISNEYYLSILPKFT

FLSKEPALESAIKSGYLYNIKSGKSFPYISGLDGILKIDIGNNQIVEVAY

PENYLFNFTTRDAEKYGFSKEVHEIYKNKVFEGFKKIPKTLGFLNKITNL

NENYQLKDGYKIFINVIYKFKNGESRYAKDVFKYSFYKNEQPLKAIFFFS

SKKQFFEVQKSLKELFHNKHSVFYRAAAELGFSKVEFLRDSKTKSSAFLY

NPEEFTVKNTEFINQIEDNVMAIVLLDKYIGNIDPLVRNFPDNLILQPIL

KEKLEDIKPFIIKSYVYKMGNFIPECKPFILKKMEDKEKNLYIGIDLSHD

TYARKTNLCIAAVDNTGDILYIGKHKNLELNEKMNLDILEKEYIKAFEKY

IEKFNVSPENVFILRDGRFIEDIEIIKNFISYNDTKYTLVEVNKNTNINS

YDDLKEWIIKLDENTYIYYPKTFLNQKGVEVKILENNTDYTIEEIIEQIY

LLTRVAHSTPYTNYKLPYPLHIANKVALTDYEWKLYIPY
```

Argonaute (Ago) proteins are composed of at least four recognized domains: (i) an amino-terminal (N-domain); (ii) a PAZ (PIWI/Argonaute/Zwille) domain; (iii) a MID (middle) domain; and (iv) a PIWI (P-element-induced whimpy testes) domain. All Ago proteins tested to date (with the exception of the MpAgo polypeptide described herein) are currently thought to bind and utilize guide RNAs with a strong preference for a 5'-phosphate group. Crystal structures of exemplary eukaryotic and prokaryotic Ago MID domains have been described. For example, the human Ago MID domain structure provides a structural basis for the 5'-nucleotide recognition of the guide RNA observed in eukaryotic Agos. Based on existing crystal structures, the phosphorylated 5'-end of the guide RNA is localized in the MID-PIWI domain interface with the 3'-end anchored to the PAZ domain. On binding to mRNA the catalytic RNase H-like active site located in the PIWI domain is in position to cleave the targeted mRNA.

Based on a secondary structure alignment (Phyre 2) and modeling into wild type *Pyrococcus furiosus* Argonaute (PfAgo, PDB #1Z25)(SEQ ID NO: 8) performed by the inventors of this application, the domain boundaries for wild type MpAgo (relative to amino acid #s of SEQ ID NO: 1), and PfAgo (relative to amino acid #s of SEQ ID NO: 8) are shown in Table 1.

TABLE 1

| Domain structure of the wild type MpAgo polypeptide | | | |
|---|---|---|---|
| MpAgo amino acid #s | SEQ ID NO: | Domain name | PfAgo amino acid #s |
| 1-109 | 2 | N domain (N terminal domain) | 1-114 |
| 110-152 | 3 | Linker 1 | 115-151 |
| 153-212 | 4 | PAZ (PIWI/Argonaute/Zwille) | 152-275 |
| 213-281 | 5 | Linker 2 | 276-361 |
| 282-430 | 6 | MID (Middle) | 362-544 |
| 431-639 | 7 | PIWI (P-element-induced whimpy testes) | 545-770 |

In some cases, a subject argonaute (Ago) polypeptide comprises an amino acid sequence having 70% or more sequence identity (e.g., 75% or more, 80% or more, 85% or more, 90% or more, 92% or more, 95% or more, 97% or more, 98% or more, 99.2% or more, 99.3% or more, 99.4% or more, 99.5% or more, 99.6% or more, 99.7% or more, 99.8% or more, 99.9% or more, or 100%) with amino acids 153-212 and/or 282-430 and/or 431-639 (e.g., 282-430 and/or 431-639; 153-212, 282-430, and 431-639; etc.) of the wild type *Marinitoga piezophila* argonaute (MpAgo) protein set forth in SEQ ID NO: 1. In some cases, a subject Ago polypeptide has at least a PAZ domain, a MID domain, and a PIWI domain. In some cases, a subject Ago polypeptide has at least a PAZ domain, a MID domain, and a PIWI domain, and comprises an amino acid sequence having 70% or more sequence identity (e.g., 75% or more, 80% or more, 85% or more, 90% or more, 92% or more, 95% or more, 97% or more, 98% or more, 99.2% or more, 99.3% or more, 99.4% or more, 99.5% or more, 99.6% or more, 99.7% or more, 99.8% or more, 99.9% or more, or 100%) with amino acids 153-212 and/or 282-430 and/or 431-639 (e.g., 282-430 and/or 431-639; 153-212, 282-430, and 431-639; etc.) of the wild type MpAgo protein set forth in SEQ ID NO: 1.

For example, in some cases, a subject Ago polypeptide comprises an amino acid sequence having 70% or more sequence identity (e.g., 75% or more, 80% or more, 85% or more, 90% or more, 92% or more, 95% or more, 97% or more, 98% or more, 99.2% or more, 99.3% or more, 99.4% or more, 99.5% or more, 99.6% or more, 99.7% or more, 99.8% or more, 99.9% or more, or 100%) with amino acids 282-430 and/or 431-639 of the wild type MpAgo protein set forth in SEQ ID NO: 1. In some cases, a subject Ago polypeptide has at least a PAZ domain, a MID domain, and a PIWI domain, and comprises an amino acid sequence having 70% or more sequence identity (e.g., 75% or more, 80% or more, 85% or more, 90% or more, 92% or more, 95% or more, 97% or more, 98% or more, 99.2% or more, 99.3% or more, 99.4% or more, 99.5% or more, 99.6% or more, 99.7% or more, 99.8% or more, 99.9% or more, or 100%) with amino acids 282-430 and/or 431-639 of the wild type MpAgo protein set forth in SEQ ID NO: 1.

As another example, in some cases, a subject Ago polypeptide comprises an amino acid sequence having 70% or more sequence identity (e.g., 75% or more, 80% or more, 85% or more, 90% or more, 92% or more, 95% or more, 97% or more, 98% or more, 99.2% or more, 99.3% or more, 99.4% or more, 99.5% or more, 99.6% or more, 99.7% or more, 99.8% or more, 99.9% or more, or 100%) with the wild type MpAgo protein set forth in SEQ ID NO: 1. In some cases, a subject Ago polypeptide has at least a PAZ domain, a MID domain, and a PIWI domain, and comprises an amino acid sequence having 70% or more sequence identity (e.g., 75% or more, 80% or more, 85% or more, 90% or more, 92% or more, 95% or more, 97% or more, 98% or more, 99.2% or more, 99.3% or more, 99.4% or more, 99.5% or more, 99.6% or more, 99.7% or more, 99.8% or more, 99.9% or more, or 100%) with the wild type MpAgo protein set forth in SEQ ID NO: 1.

In some embodiments, a subject Ago polypeptide can be codon optimized. In some cases, a codon optimized Ago polypeptide is a variant MpAgo polypeptide. In some cases, a codon optimized Ago polypeptide is a chimeric MpAgo polypeptide. Codon optimization is known in the art and entails the mutation of foreign-derived DNA to mimic the codon preferences of the intended host organism or host cell while encoding the same protein. Thus, the codons are changed, but the encoded protein remains unchanged. For example, if the intended target cell was a human cell, a human codon optimized subject Ago polypeptide (or MpAgo variant) would be a suitable Ago polypeptide. As another non-limiting example, if the intended host cell were a mouse cell, than a mouse codon optimized subject Ago polypeptide (or MpAgo variant, e.g., enzymatically inactive variant) would be a suitable Ago polypeptide. While codon optimization is not required, it is acceptable and may be preferable in certain cases.

Variant MgAgo Polypeptide

In some embodiments (e.g., in methods of binding, in methods of modifying a target DNA without target DNA cleavage, etc.), a subject Ago polypeptide is a variant MpAgo polypeptide. As used herein, the term "variant MpAgo polypeptide" refers to a subject Ago polypeptide that has an amino acid sequence that is different than (i.e., not identical to) the wild type MpAgo protein set forth in SEQ ID NO: 1. In some embodiments, a variant MpAgo polypeptide is a chimeric MpAgo polypeptide. In some embodiments, a variant MpAgo polypeptide is a mutant MpAgo polypeptide. In some cases, a variant MpAgo polypeptide is a chimeric and a mutant MpAgo polypeptide. Thus, the term "variant MpAgo polypeptide" encompasses both of the terms "chimeric MpAgo polypeptide" and "mutant MpAgo polypeptide."

Chimeric MpAgo Polypeptide

A "chimeric MpAgo polypeptide" (also referred to herein as an MpAgo fusion polypeptide) is a subject Ago polypeptide (as described above) having a heterologous amino acid sequence (e.g., a fusion partner). A MpAgo fusion poypeptide is a variant MpAgo polypeptide by virtue of differing in sequence from a wild type MpAgo polypeptide. An MpAgo fusion poypeptide is a subject Ago polypeptide (e.g., a wild type MpAgo polypeptide, a variant MpAgo polypeptide, a variant MpAgo polypeptide with reduced nuclease activity, and the like) fused to a covalently linked heterologous polypeptide (also referred to as a "fusion partner"). In some cases, a MpAgo fusion poypeptide is a variant MpAgo polypeptide with reduced nuclease activity fused to a covalently linked heterologous polypeptide. For example, a chimeric MpAgo polypeptide can include one or more mutations as described below for a "mutant MpAgo polypeptide." In some cases, the heterologous polypeptide exhibits (and therefore provides for) an activity (e.g., an enzymatic activity) that will also be exhibited by the MpAgo fusion polypeptide (e.g., methyltransferase activity, acetyltransferase activity, kinase activity, ubiquitinating activity, etc.). In some such cases, a method of binding, e.g., where the subject Ago polypeptide is a variant MpAgo polypeptide having a fusion partner (i.e., having a heterologous polypeptide) with an activity (e.g., an enzymatic activity) that modifies the target nucleic acid, the method can also be considered to be a method of modifying the target nucleic acid. In some cases, a method of binding a target nucleic acid (e.g., a single stranded target nucleic acid) can result in modification of the target nucleic acid. Thus, in some cases, a method of binding a target nucleic acid (e.g., a single stranded target nucleic acid) can be a method of modifying the target nucleic acid.

In some cases, the heterologous sequence provides for subcellular localization (i.e., the heterologous sequence is a subcellular localization sequence (e.g., a nuclear localization signal (NLS) for targeting to the nucleus, a sequence to keep the fusion protein out of the nucleus (e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a variant MpAgo does not include a NLS so that the protein is not targeted to the nucleus (which can be advantageous, e.g., when the target nucleic acid is an RNA that is present in the cytosol). In some embodiments, the heterologous sequence can provide a tag (i.e., the heterologous sequence is a detectable label) for ease of tracking and/or purification (e.g., a fluorescent protein, e.g., green fluorescent protein (GFP), YFP, RFP, CFP, mCherry, tdTomato, and the like; a histidine tag, e.g., a 6×His tag; a hemagglutinin (HA) tag; a FLAG tag; a Myc tag; and the like). In some embodiments, the heterologous sequence can provide for increased or decreased stability (i.e., the heterologous sequence is a stability control peptide, e.g., a degron, which in some cases is controllable (e.g., a temperature sensitive or drug controllable degron sequence, see below). In some embodiments, the heterologous sequence can provide for increased or decreased transcription from the target nucleic acid (i.e., the heterologous sequence is a transcription modulation sequence, e.g., a transcription factor/activator or a fragment thereof, a protein or fragment thereof that recruits a transcription factor/activator, a transcription repressor or a fragment thereof, a protein or fragment thereof that recruits a transcription repressor, a small molecule/drug-responsive transcription regulator, etc.). In some embodiments, the heterologous sequence can provide a binding domain (i.e., the heterologous sequence is a protein binding sequence, e.g., to provide the ability of a MpAgo fusion polypeptide to bind to another protein of interest, e.g., a DNA or histone modifying protein, a transcription factor or transcription repressor, a recruiting protein, an RNA modification enzyme, an RNA-binding protein, a translation initiation factor, an RNA splicing factor, etc.). A heterologous nucleic acid sequence may be linked to another nucleic acid sequence (e.g., by genetic engineering) to generate a chimeric nucleotide sequence encoding a chimeric polypeptide.

Suitable fusion partners that provide for increased or decreased stability include, but are not limited to degron sequences. Degrons are readily understood by one of ordinary skill in the art to be amino acid sequences that control the stability of the protein of which they are part. For example, the stability of a protein comprising a degron sequence is controlled in part by the degron sequence. In some cases, a suitable degron is constitutive such that the degron exerts its influence on protein stability independent of experimental control (i.e., the degron is not drug inducible, temperature inducible, etc.) In some cases, the degron provides the variant MpAgo polypeptide with controllable stability such that the variant MpAgo polypeptide can be turned "on" (i.e., stable) or "off" (i.e., unstable, degraded) depending on the desired conditions. For example, if the degron is a temperature sensitive degron, the variant MpAgo polypeptide may be functional (i.e., "on", stable) below a threshold temperature (e.g., 42° C., 41° C., 40° C., 39° C., 38° C., 37° C., 36° C., 35° C., 34° C., 33° C., 32° C., 31° C., 30° C., etc.) but non-functional (i.e., "off", degraded) above the threshold temperature. As another example, if the degron is a drug inducible degron, the presence or absence of drug can switch the protein from an "off" (i.e., unstable) state to an "on" (i.e., stable) state or vice versa. An exemplary drug inducible degron is derived from the FKBP12 protein. The stability of the degron is controlled by the presence or absence of a small molecule that binds to the degron.

Examples of suitable degrons include, but are not limited to those degrons controlled by Shield-1, DHFR, auxins, and/or temperature. Non-limiting examples of suitable degrons are known in the art (e.g., Dohmen et al., Science, 1994. 263(5151): p. 1273-1276: Heat-inducible degron: a method for constructing temperature-sensitive mutants; Schoeber et al., Am J Physiol Renal Physiol. 2009 January; 296(1):F204-11: Conditional fast expression and function of multimeric TRPV5 channels using Shield-1; Chu et al., Bioorg Med Chem Lett. 2008 Nov. 15; 18(22):5941-4: Recent progress with FKBP-derived destabilizing domains; Kanemaki, Pflugers Arch. 2012 Dec. 28: Frontiers of protein expression control with conditional degrons; Yang et al., Mol Cell. 2012 Nov. 30; 48(4):487-8: Titivated for destruction: the methyl degron; Barbour et al., Biosci Rep. 2013 Jan. 18; 33(1): Characterization of the bipartite degron that regulates ubiquitin-independent degradation of thymidylate synthase; and Greussing et al., J Vis Exp. 2012 Nov. 10; (69): Monitoring of ubiquitin-proteasome activity in living cells using a Degron (dgn)-destabilized green fluorescent protein (GFP)-based reporter protein; all of which are hereby incorporated in their entirety by reference).

Exemplary degron sequences have been well-characterized and tested in both cells and animals. Thus, fusing a subject Ago polypeptide (e.g., wild type MpAgo; variant MpAgo; variant MpAgo with reduced nuclease activity; and the like) to a degron sequence produces a "tunable" and "inducible" Ago polypeptide. Any of the fusion partners described herein can be used in any desirable combination. As one non-limiting example to illustrate this point, a MpAgo fusion protein (i.e., a chimeric MpAgo polypeptide) can comprise a YFP sequence for detection, a degron sequence for stability, and transcription activator sequence to increase transcription of the target nucleic acid. A suitable reporter protein for use as a fusion partner for a subject Ago polypeptide (e.g., wild type MpAgo, variant MpAgo, variant MpAgo with reduced nuclease function, etc.), includes, but is not limited to, the following exemplary proteins (or functional fragment thereof): his3, β-galactosidase, a fluorescent protein (e.g., GFP, RFP, YFP, cherry, tomato, etc., and various derivatives thereof), luciferase, β-glucuronidase, and alkaline phosphatase. Furthermore, the number of fusion partners that can be used in a MpAgo fusion protein is unlimited. In some cases, a MpAgo fusion protein comprises one or more (e.g. two or more, three or more, four or more, or five or more) heterologous sequences.

Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity, any of which can be directed at modifying nucleic acid directly (e.g., methylation of DNA or RNA) or at modifying a nucleic acid-associated polypeptide (e.g., a histone, a DNA binding protein, and RNA binding protein, and the like). Further suitable fusion partners include, but are not limited to boundary elements (e.g., CTCF), proteins and fragments thereof that provide periphery recruitment (e.g., Lamin A, Lamin B, etc.), and protein docking elements (e.g., FKBP/FRB, Pill/Abyl, etc.).

Examples of various additional suitable fusion partners (or fragments thereof) for a subject variant MpAgo polypeptide include, but are not limited to, those described in the PCT patent applications: WO2010075303, WO2012068627, and WO2013155555 which are hereby incorporated by reference in their entirety.

Suitable fusion partners include, but are not limited to, a polypeptide that provides an activity that indirectly increases transcription by acting directly on the target nucleic acid or on a polypeptide (e.g., a histone, a DNA-binding protein, an RNA-binding protein, an RNA editing protein, etc.) associated with the target nucleic acid. Suitable fusion partners include, but are not limited to, a polypeptide that provides for methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, or demyristoylation activity.

Additional suitable fusion partners include, but are not limited to, a polypeptide that directly provides for increased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.).

Non-limiting examples of fusion partners to accomplish increased or decreased transcription include transcription activator and transcription repressor domains (e.g., the Krüppel associated box (KRAB or SKD); the Mad mSIN3 interaction domain (SID); the ERF repressor domain (ERD), etc). In some such cases, a MpAgo fusion protein is targeted by the guide nucleic acid to a specific location (i.e., sequence) in the target nucleic acid and exerts locus-specific regulation such as blocking RNA polymerase binding to a promoter (which selectively inhibits transcription activator function), and/or modifying the local chromatin status (e.g., when a fusion sequence is used that modifies the target nucleic acid or modifies a polypeptide associated with the target nucleic acid). In some cases, the changes are transient (e.g., transcription repression or activation). In some cases, the changes are inheritable (e.g., when epigenetic modifications are made to the target nucleic acid or to proteins associated with the target nucleic acid, e.g., nucleosomal histones).

Non-limiting examples of fusion partners for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a fusion partner can include the entire protein or in some cases can include a fragment of the protein (e.g., a functional domain).

In some embodiments, the heterologous sequence can be fused to the C-terminus of a subject Ago polypeptide. In some embodiments, the heterologous sequence can be fused to the N-terminus of a subject Ago polypeptide. In some embodiments, the heterologous sequence can be fused to an internal portion (i.e., a portion other than the N- or C-terminus) a subject Ago polypeptide.

In addition, the fusion partner of a chimeric MpAgo polypeptide can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; endonucleases (for example RNase I I I, the CRR22 DYW domain, Dicer, and PIN (PilT N-terminus) domains from proteins such as SMG5 and SMG6); proteins and protein domains responsible for stimulating RNA cleavage (for example CPSF, CstF, CFIm and CFIIm); Exonucleases (for example XRN-1 or Exonuclease T); Deadenylases (for example HNT3); proteins and protein domains responsible for nonsense mediated RNA decay (for example UPF1, UPF2, UPF3, UPF3b, RNP S1, Y14, DEK, REF2, and SRm160); proteins and protein domains responsible for stabilizing RNA (for example PABP); proteins and protein domains responsible for repressing translation (for example Ago2 and Ago4); proteins and protein domains responsible for stimulating translation (for example Staufen); proteins and protein domains responsible for polyadenylation of RNA (for example PAP1, GLD-2, and Star-PAP); proteins and protein domains responsible for polyuridinylation of RNA (for example CI D1 and terminal uridylate transferase); proteins and protein domains responsible for RNA localization (for example from IMP1, ZBP1, She2p, She3p, and Bicaudal-D); proteins and protein domains responsible for nuclear retention of RNA (for example Rrp6); proteins and protein domains responsible for nuclear export of RNA (for example TAP, NXF1, THO, TREX, REF, and Aly); proteins and protein domains responsible for repression of RNA splicing (for example PTB, Sam68, and hnRNP A1); proteins and protein domains responsible for stimulation of RNA splicing (for example Serine/Arginine-rich (SR) domains); proteins and protein domains responsible for reducing the efficiency of transcription (for example FUS (TLS)); and proteins and protein domains responsible for stimulating transcription (for example CDK7 and HIV Tat). Alternatively, the effector domain may be selected from the group comprising endonucleases; proteins and protein domains capable of stimulating RNA cleavage; exonucleases; Deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable fusion partner is a PUF RNA-binding domain, which is described in more detail in WO2012068627.

Some RNA splicing factors that can be used (in whole or as fragments thereof) as fusion partners for a subject Ago polypeptide have modular organization, with separate sequence-specific RNA binding modules and splicing effector domains. For example, members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP Al binds to exonic splicing silencers (ESSs) through its RRM domains and inhibits exon inclusion through a C-terminal Glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP Al can bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cω-elements that are located in either the core exon region or the exon extension region (i.e., between the two alternative 5' splice sites). For more examples, see WO2010075303.

In some embodiments, a subject Ago polypeptide (e.g., a wild type MpAgo, a variant MpAgo, a variant MpAgo with reduced nuclease activity, etc.) can be linked to a fusion partner via a peptide spacer.

Mutant MpAgo Polypeptide

A "mutant MpAgo polypeptide" is a subject Ago polypeptide (as described above) having an amino acid sequence that includes one or more mutations (e.g, insertions, deletions, substitutions, etc.) relative to (i.e., compared to) the wild type MpAgo protein set forth in SEQ ID NO: 1. Thus, in some embodiments, a variant MpAgo polypeptide (e.g, a mutant MpAgo polypeptide) includes an amino acid sequence having one or more mutations relative to the wild type MpAgo protein (SEQ ID NO: 1), and having 70% or more sequence identity (e.g., 75% or more, 80% or more, 85% or more, 90% or more, 92% or more, 95% or more, 97% or more, 98% or more, 99.2% or more, 99.3% or more, 99.4% or more, 99.5% or more, 99.6% or more, 99.7% or more, 99.8% or more, 99.9% or more, or 100%) with amino acids 153-212 and/or 282-430 and/or 431-639 (e.g., 282-430 and/or 431-639; 153-212, 282-430, and 431-639; etc.) of the wild type MpAgo protein set forth in SEQ ID NO: 1. In some cases, a variant MpAgo polypeptide includes an amino acid sequence having (i) one or more mutations relative to the wild type MpAgo (SEQ ID NO: 1), (ii) at least a PAZ domain, a MID domain, and a PIWI domain, and (iii) 70% or more sequence identity (e.g., 75% or more, 80% or more, 85% or more, 90% or more, 92% or more, 95% or more, 97% or more, 98% or more, 99.2% or more, 99.3% or more, 99.4% or more, 99.5% or more, 99.6% or more, 99.7% or more, 99.8% or more, 99.9% or more, or 100%) with amino acids 153-212 and/or 282-430 and/or 431-639 of the wild type MpAgo protein set forth in SEQ ID NO: 1.

Figure 2A:
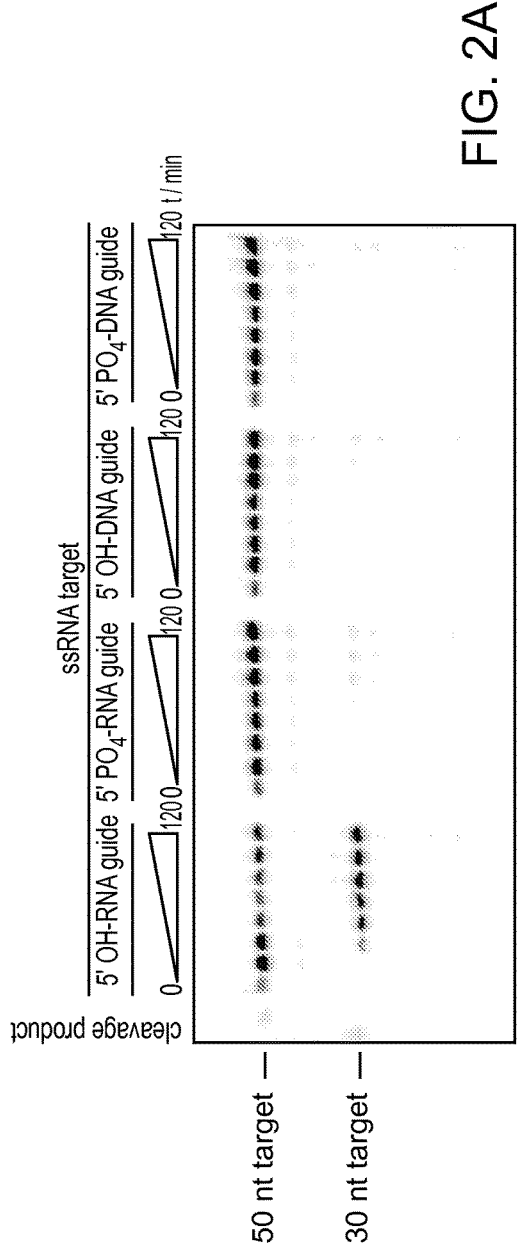
FIGS. 2A-D depict cleavage assays testing the parameters (e.g., guide RNA parameters, target nucleic acid parameters, etc.) of MpAgo cleavage activity; and depict a Western blot showing the binding of polyclonal anti-MpAgo antibodies to MpAgo.
Figure 2B:
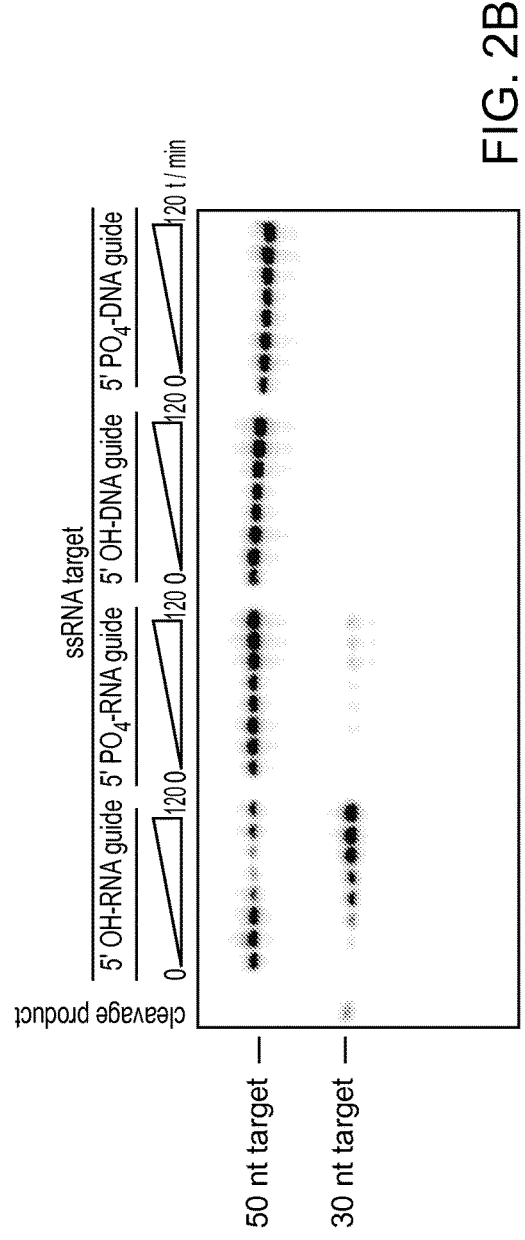
Figure 2C:
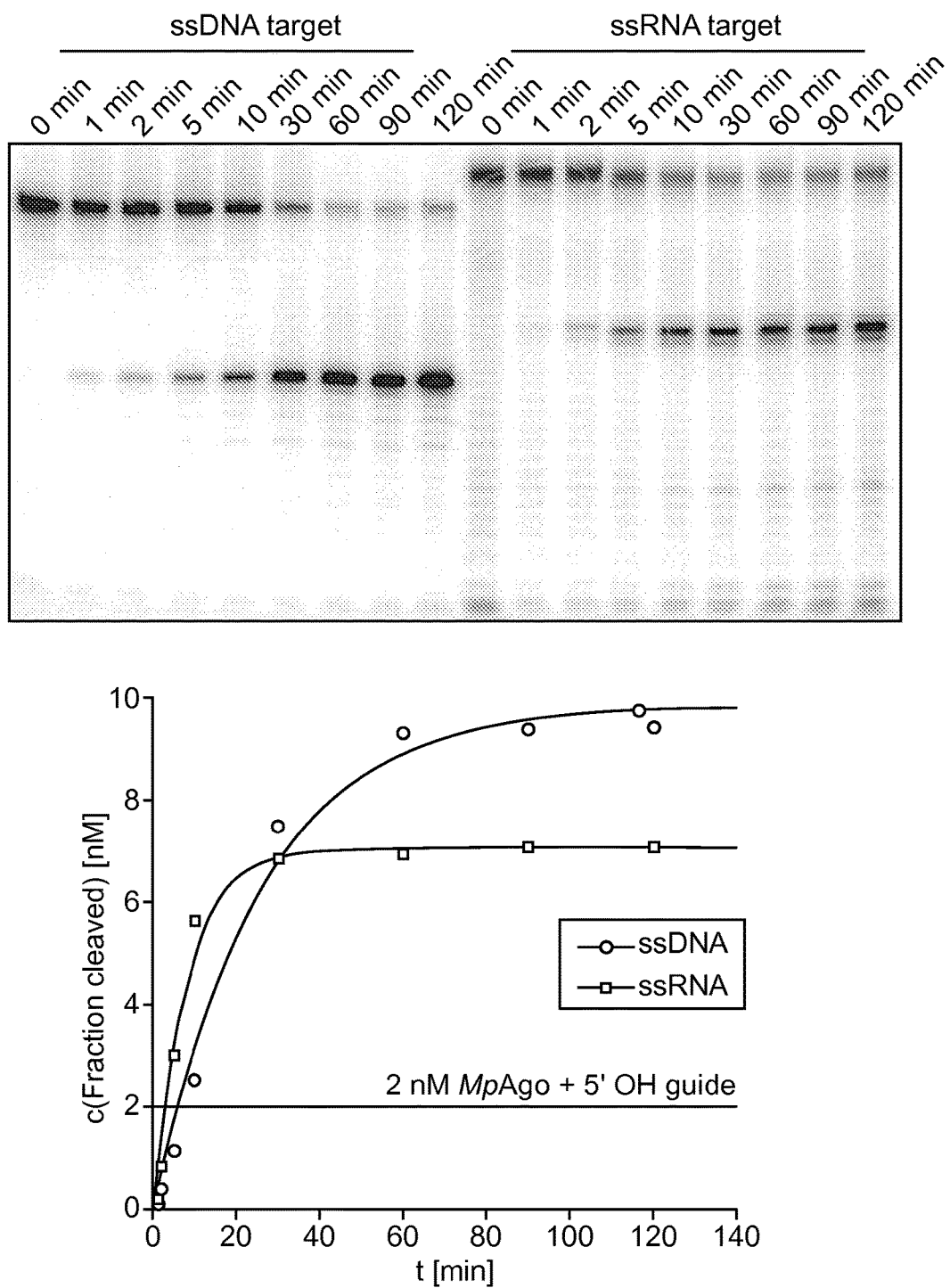
Figure 2D:
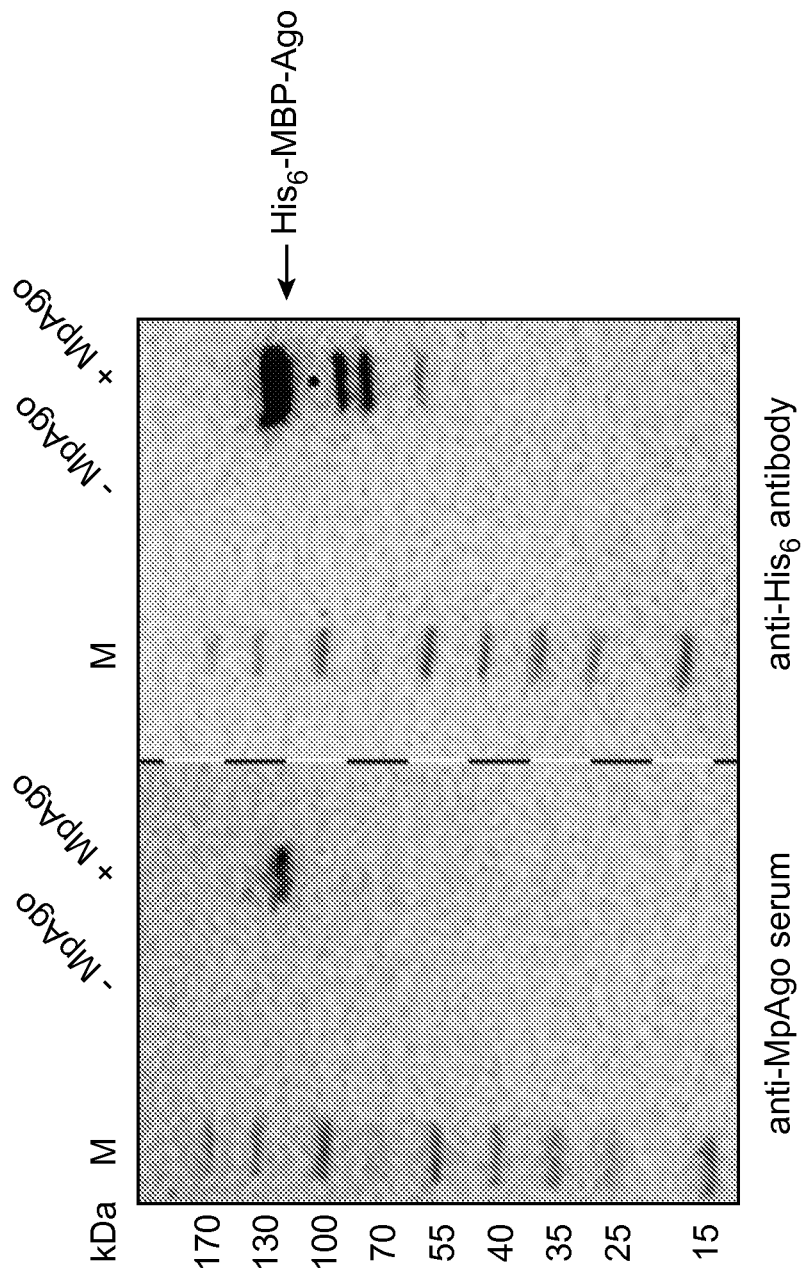
Figure 3B:
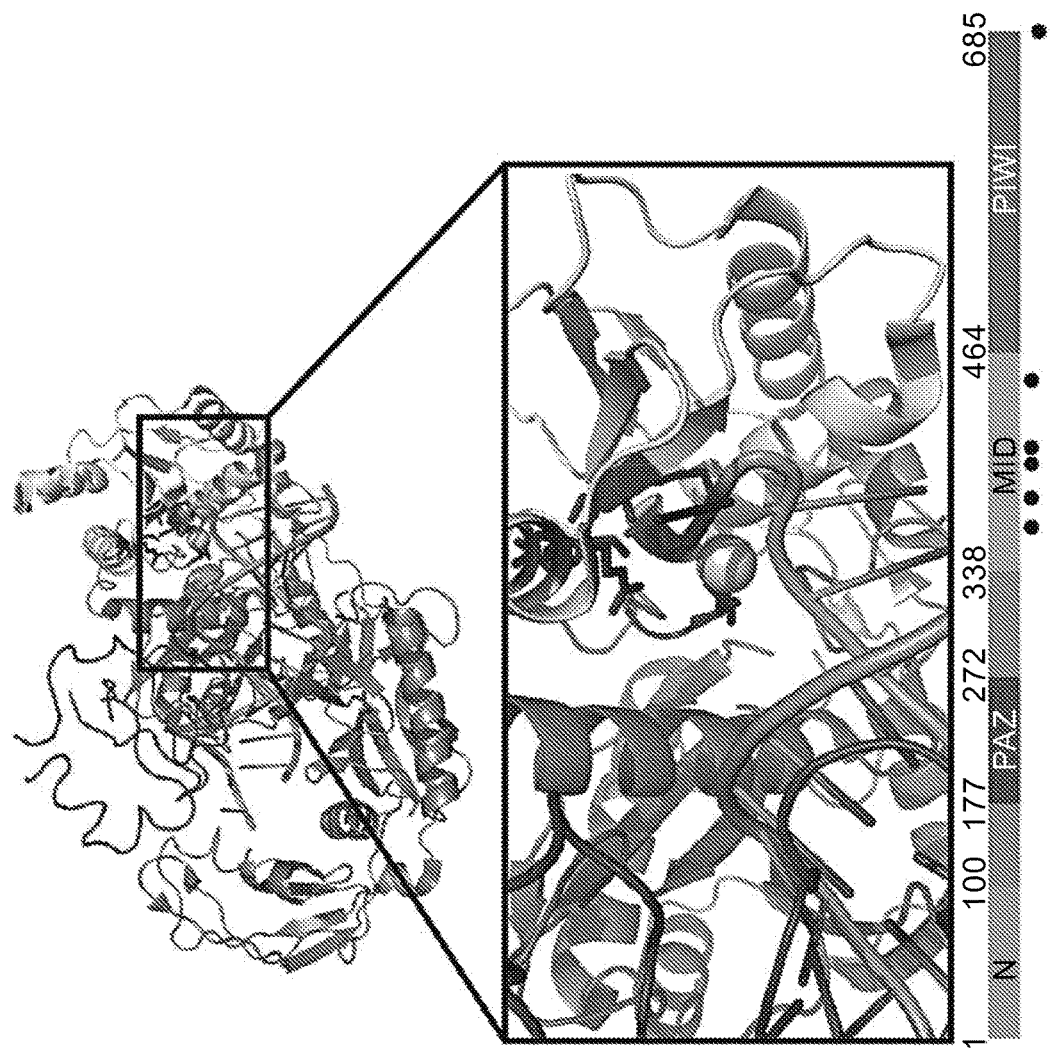

In some cases, a variant MpAgo polypeptide exhibits reduced nuclease activity compared to the wild type MpAgo protein set forth in SEQ ID NO: 1. Thus, in some cases, a subject variant MpAgo polypeptide is a mutant MpAgo polypeptide that has one or more mutations and exhibits reduced nuclease activity compared to the wild type MpAgo protein set forth in SEQ ID NO: 1. For example, in some instances, the variant (e.g., mutant) MpAgo polypeptide has 50% or less (e.g., 40% or less, 30% or less, 20% or less, 25% or less, 15% or less, 10% or less, 5% or less, 1% or less, or none) of the nuclease activity of the corresponding wild-type MpAgo polypeptide (SEQ ID NO: 1). Assays to determine nuclease activity include assays that cleave a single stranded target nucleic acid and can be any convenient nucleic acid cleavage assay that tests for nucleic acid cleavage of a target single stranded nucleic acid. Exemplary cleavage assays are shown in FIG. 1, FIG. 2, FIG. 3, and FIG. 4 and include cleavage assays that include contacting a target single stranded nucleic acid with a guide RNA and a subject Ago polypeptide, and detecting the presence or absence of a cleavage product. In some cases, the variant MpAgo polypeptide has no substantial nuclease activity. Based on both secondary structure and sequence alignments, the catalytic tetrad (the so called DEDX motif) in the active site of the PIWI domain is: Asp446 (D446), Glu482 (E482), Asp516 (D516), and Asn624 (N624) (FIG. 3A).

Figure 4:
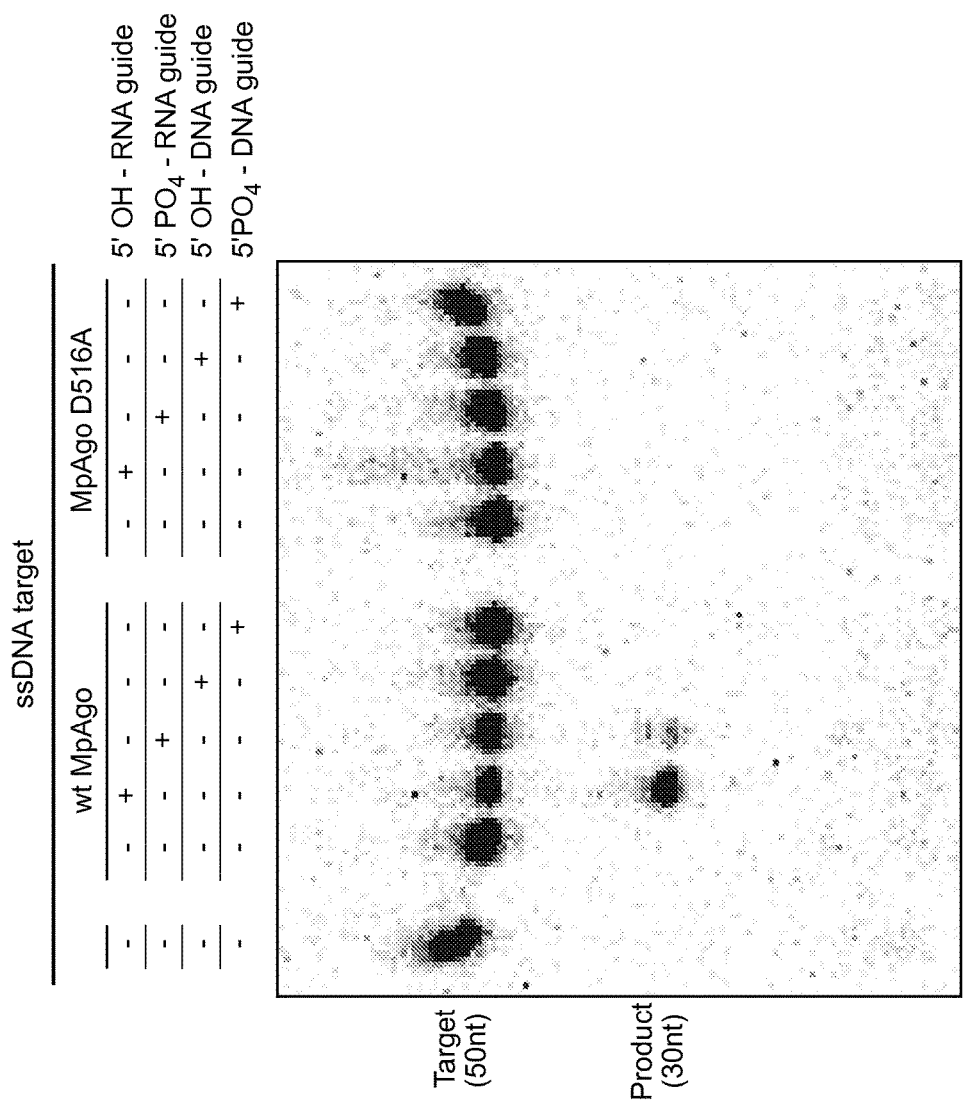
FIG. 4 depicts results from cleavage assays comparing the activity of wild type MpAgo to a D516A mutant MpAgo.

In some cases, a variant MpAgo polypeptide with reduced nuclease activity includes a mutation relative to the wild type MpAgo protein set forth in SEQ ID NO: 1 that modifies (e.g., substitutes for) or removes at least one of: D446, E482, D516, and N624. In some cases, a variant MpAgo polypeptide includes a mutation (or mutations) relative to the wild type MpAgo protein set forth in SEQ ID NO: 1 that modifies (e.g., substitutes for) or removes one or more (e.g., 2 or more, 3 or more, or all 4) of the amino acids at positions: D446, E482, D516, and N624. In some cases, a variant MpAgo polypeptide includes an amino acid sequence having a substitution or deletion in one or more amino acid positions selected from: D446, E482, D516, and N624 compared to the wild type MpAgo protein set forth in SEQ ID NO: 1. In some cases, a mutation relative to the wild type MpAgo protein set forth in SEQ ID NO: 1 is a substitution to any amino acid selected from: A, V, I, L, M, or G. In some cases, the mutation is one or more mutations (e.g., 2 or more, 3 or more, or all 4) selected from: D446A, E482A, D516A, and N624A. In some cases, the one or more mutations includes D516A (FIG. 4).

In some embodiments, a mutant MpAgo polypeptide is mutated to enhance or reduce the preference for a 5'-OH guide RNA over a 5'-phosphorylated guide RNA. Residues in the MID domain predicted to be involved in binding the 5'-end of the guide RNA are (based on modeling of wild type MpAgo into the known structure of PfAgo) are: Ile363 (I363), Glu367 (E367), Ile383 (I383), Val387 (V387), Asp392 (D392), Asn393 (N393), and Lys418 (K418). In addition, amino acids D340, E367, D392, N393, and D406 are highly conserved in the Ago proteins of other organisms, but not conserved in wild type MpAgo.

In some cases, a variant MpAgo polypeptide includes at least one mutation (e.g., 1 or more mutations, 2 or more mutations, 3 or more mutations, 4 or more mutations, 5 or more mutations, 6 or more mutations, 7 or more mutations, 8 or more mutations, up to 9 mutations, up to 8 mutations, up to 7 mutations, up to 6 mutations, up to 5 mutations, up to 4 mutations, up to 3 mutations, up to 2 mutations, or 1 mutation) relative to the wild type MpAgo protein set forth in SEQ ID NO: 1 that modifies (e.g., substitutes for) or removes an amino acid selected from: D340, I363, E367, I383, V387, D392, N393, D406, and K418. In some such cases, the mutation is a substitution to any amino acid selected from: A, V, I, L, M, or G. In some cases, the mutation is selected from: D340A, I363A, E367A, I383A, V387A, D392A, N393A, D406A, and K418A. As such, in some embodiments, a variant MpAgo polypeptide includes up to 9 mutations (e.g., up to 8 mutations, up to 7 mutations, up to 6 mutations, up to 5 mutations, up to 4 mutations, up to 3 mutations, up to 2 mutations, or 1 mutation) relative to the wild type MpAgo protein set forth in SEQ ID NO: 1, selected from: D340A, I363A, E367A, I383A, V387A, D392A, N393A, D406A, and K418A. In some embodiments, a variant MpAgo polypeptide includes at least one mutation (e.g., 1 or more mutations, 2 or more mutations, 3 or more mutations, 4 or more mutations, 5 or more mutations, 6 or more mutations, 7 or more mutations, 8 or more mutations, etc.) relative to the wild type MpAgo protein set forth in SEQ ID NO: 1, selected from: D340A, I363A, E367A, I383A, V387A, D392A, N393A, D406A, and K418A.

In some cases, the mutation modifies the subject variant MpAgo polypeptide (relative to the wild type MpAgo protein set forth in SEQ ID NO: 1) to become more like other known Ago polypeptides (e.g., human, *drosophila, Pyrococcus furiosus, Thermus thermophilus*, etc.)(see FIG. 3A). For example, such a modification can cause the variant MpAgo to have a decreased preference for a guide RNA with a 5'-OH and/or an increased preference for a guide RNA with a 5'-phosphate. In some such cases, the mutation is selected from: D340R/K, I363F, E367R/K, I383V, D392T/S, N393Q, and D406R/K. This is equivalent to saying that in some such cases, the mutation is selected from: D340R, D340K, I363F, E367R, E367K, I383V, D392T, D392S, N393Q, D406R, and D406K. As such, in some embodiments, a variant MpAgo polypeptide includes up to 9 mutations (e.g., up to 8 mutations, up to 7 mutations, up to 6 mutations, up to 5 mutations, up to 4 mutations, up to 3 mutations, up to 2 mutations, or 1 mutation) relative to the wild type MpAgo protein set forth in SEQ ID NO: 1, selected from: D340R, D340K, I363F, E367R, E367K, I383V, D392T, D392S, N393Q, D406R, and D406K. In some embodiments, a variant MpAgo polypeptide includes up to 8 mutations (e.g., up to 7 mutations, up to 6 mutations, up to 5 mutations, up to 4 mutations, up to 3 mutations, up to 2 mutations, or 1 mutation) relative to the wild type MpAgo protein set forth in SEQ ID NO: 1, selected from: D340R, D340K, E367R, E367K, I383V, D392T, D392S, N393Q, D406R, and D406K. In some such cases, the C-terminus from another Ago polypeptide can be fused to the C-terminus of the subject variant MpAgo polypeptide (the C-terminus that is present in many other Ago polypeptides is not present in the MpAgo polypeptide, as set forth in SEQ ID NO: 1).

In some embodiments, a variant MpAgo polypeptide includes at least one mutation (e.g., 1 or more mutations, 2 or more mutations, 3 or more mutations, 4 or more mutations, 5 or more mutations, 6 or more mutations, 7 or more mutations, 8 or more mutations, etc.) relative to the wild type MpAgo protein set forth in SEQ ID NO: 1, selected from: D340R, D340K, I363F, E367R, E367K, I383V, D392T, D392S, N393Q, D406R, and D406K. In some embodiments, a variant MpAgo polypeptide includes at least one mutation (e.g., 1 or more mutations, 2 or more mutations, 3 or more mutations, 4 or more mutations, 5 or more mutations, 6 or more mutations, 7 or more mutations, 8 or more mutations, etc.) relative to the wild type MpAgo protein set forth in SEQ ID NO: 1, selected from: D340R, D340K, E367R, E367K, I383V, D392T, D392S, N393Q, D406R, and D406K.

Nucleic Acids Encoding a Guide RNA, a Precursor RNA, a Subject Ago Polypeptide, and/or a 5'-OH Generating Nuclease The present disclosure provides compositions and methods that include one or more of: a guide RNA, a precursor RNA, a subject Ago polypeptide, and a 5'-OH generating nuclease. In some cases, a guide RNA and/or a precursor RNA and/or a subject Ago polypeptide, and/or a 5'-OH generating nuclease is provided as a nucleic acid. In some embodiments, a subject nucleic acid is an expression vector, e.g., a recombinant expression vector. As such, in some embodiments, a subject method involves contacting a target nucleic acid (e.g., a single stranded target nucleic acid) or introducing into a cell (or a population of cells) at least one of: a guide RNA, a precursor RNA, a subject Ago polypeptide, and a 5'-OH generating nuclease. In some embodiments a cell comprising a target nucleic acid is in vitro and/or ex vivo. In some embodiments a cell comprising a target nucleic acid is in vivo. Suitable nucleic acids comprising nucleotide sequences encoding a precursor RNA, a subject Ago polypeptide, and/or a 5'-OH generating nuclease include expression vectors, where an expression vector comprising a nucleotide sequence encoding a precursor RNA, a subject Ago polypeptide, and/or a 5'-OH generating nuclease is a "recombinant expression vector."

In some embodiments, the recombinant expression vector is a viral construct, e.g., a recombinant adeno-associated virus construct (see, e.g., U.S. Pat. No. 7,078,387), a recombinant adenoviral construct, a recombinant lentiviral construct, a recombinant retroviral construct, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

In some embodiments, a nucleotide sequence encoding precursor RNA, a subject Ago polypeptide, and/or a 5'-OH generating nuclease is operably linked to a control element, e.g., a transcriptional control element, such as a promoter. The transcriptional control element may be functional in either a eukaryotic cell, e.g., a mammalian cell; or a prokaryotic cell (e.g., bacterial or archaeal cell). In some embodiments, a nucleotide sequence encoding precursor RNA, a subject Ago polypeptide, and/or a 5'-OH generating nuclease is operably linked to multiple control elements that allow expression of the nucleotide sequence encoding precursor RNA, a subject Ago polypeptide, and/or a 5'-OH generating nuclease in both prokaryotic and eukaryotic cells.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression. The expression vector may also include nucleotide sequences encoding protein tags (e.g., 6×His tag, hemagglutinin tag, green fluorescent protein, etc.) that are fused to a subject Ago polypeptide, thus resulting in a chimeric polypeptide.

In some embodiments, a nucleotide sequence encoding a precursor RNA and/or a subject Ago polypeptide and/or a 5'-OH generating nuclease is operably linked to an inducible promoter. In some embodiments, a nucleotide sequence encoding precursor RNA and/or a subject Ago polypeptide and/or a 5'-OH generating nuclease is operably linked to a constitutive promoter.

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6) (Miyagishi et al., Nature Biotechnology 20, 497-500 (2002)), an enhanced U6 promoter (e.g., Xia et al., Nucleic Acids Res. 2003 Sep. 1; 31(17)), a human H1 promoter (H1), and the like.

Examples of inducible promoters include, but are not limited to T7 RNA polymerase promoter, T3 RNA polymerase promoter, Isopropyl-beta-D-thiogalactopyranoside (IPTG)-regulated promoter, lactose induced promoter, heat shock promoter, Tetracycline-regulated promoter, Steroid-regulated promoter, Metal-regulated promoter, estrogen receptor-regulated promoter, etc. Inducible promoters can therefore be regulated by molecules including, but not limited to, doxycycline; RNA polymerase, e.g., T7 RNA polymerase; an estrogen receptor; an estrogen receptor fusion; etc.

In some embodiments, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used and the choice of suitable promoter (e.g., a brain specific promoter, a promoter that drives expression in a subset of neurons, a promoter that drives expression in the germline, a promoter that drives expression in the lungs, a promoter that drives expression in muscles, a promoter that drives expression in islet cells of the pancreas, etc.) will depend on the organism. For example, various spatially restricted promoters are known for plants, flies, worms, mammals, mice, etc. Thus, a spatially restricted promoter can be used to regulate the expression of a nucleic acid encoding a subject Cas9 polypeptide in a wide variety of different tissues and cell types, depending on the organism. Some spatially restricted promoters are also temporally restricted such that the promoter is in the "ON" state or "OFF" state during specific stages of embryonic development or during specific stages of a biological process (e.g., hair follicle cycle in mice).

For illustration purposes, examples of spatially restricted promoters include, but are not limited to, neuron-specific promoters, adipocyte-specific promoters, cardiomyocyte-specific promoters, smooth muscle-specific promoters, photoreceptor-specific promoters, etc. Neuron-specific spatially restricted promoters include, but are not limited to, a neuron-specific enolase (NSE) promoter (see, e.g., EMBL HSENO2, X51956); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19; and Llewellyn, et al. (2010) Nat. Med. 16(10):1161-1166); a serotonin receptor promoter (see, e.g., GenBank S62283); a tyrosine hydroxylase promoter (TH) (see, e.g., Oh et al. (2009) Gene Ther 16:437; Sasaoka et al. (1992) Mol. Brain Res. 16:274; Boundy et al. (1998) J. Neurosci. 18:9989; and Kaneda et al. (1991) Neuron 6:583-594); a GnRH promoter (see, e.g., Radovick et al. (1991) Proc. Natl. Acad. Sci. USA 88:3402-3406); an L7 promoter (see, e.g., Oberdick et al. (1990) Science 248:223-226); a DNMT promoter (see, e.g., Bartge et al. (1988) Proc. Natl. Acad. Sci. USA 85:3648-3652); an enkephalin promoter (see, e.g., Comb et al. (1988) EMBO J. 17:3793-3805); a myelin basic protein (MBP) promoter; a Ca2+-calmodulin-dependent protein kinase II-alpha (CamKIIα) promoter (see, e.g., Mayford et al. (1996) Proc. Natl. Acad. Sci. USA 93:13250; and Casanova et al. (2001) Genesis 31:37); a CMV enhancer/platelet-derived growth factor-β promoter (see, e.g., Liu et al. (2004) Gene Therapy 11:52-60); and the like.

Adipocyte-specific spatially restricted promoters include, but are not limited to aP2 gene promoter/enhancer, e.g., a region from −5.4 kb to +21 bp of a human aP2 gene (see, e.g., Tozzo et al. (1997) Endocrinol. 138:1604; Ross et al. (1990) Proc. Natl. Acad. Sci. USA 87:9590; and Pavjani et al. (2005) Nat. Med. 11:797); a glucose transporter-4 (GLUT4) promoter (see, e.g., Knight et al. (2003) Proc. Natl. Acad. Sci. USA 100:14725); a fatty acid translocase (FAT/CD36) promoter (see, e.g., Kuriki et al. (2002) Biol. Pharm. Bull. 25:1476; and Sato et al. (2002) J. Biol. Chem. 277:15703); a stearoyl-CoA desaturase-1 (SCD1) promoter (Tabor et al. (1999) J. Biol. Chem. 274:20603); a leptin promoter (see, e.g., Mason et al. (1998) Endocrinol. 139: 1013; and Chen et al. (1999) Biochem. Biophys. Res. Comm. 262:187); an adiponectin promoter (see, e.g., Kita et al. (2005) Biochem. Biophys. Res. Comm. 331:484; and Chakrabarti (2010) Endocrinol. 151:2408); an adipsin promoter (see, e.g., Platt et al. (1989) Proc. Natl. Acad. Sci. USA 86:7490); a resistin promoter (see, e.g., Seo et al. (2003) Molec. Endocrinol. 17:1522); and the like.

Cardiomyocyte-specific spatially restricted promoters include, but are not limited to control sequences derived from the following genes: myosin light chain-2, α-myosin heavy chain, AE3, cardiac troponin C, cardiac actin, and the like. Franz et al. (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

Smooth muscle-specific spatially restricted promoters include, but are not limited to an SM22α promoter (see, e.g., Akytirek et al. (2000) Mol. Med. 6:983; and U.S. Pat. No. 7,169,874); a smoothelin promoter (see, e.g., WO 2001/018048); an α-smooth muscle actin promoter; and the like. For example, a 0.4 kb region of the SM22α promoter, within which lie two CArG elements, has been shown to mediate vascular smooth muscle cell-specific expression (see, e.g., Kim, et al. (1997) Mol. Cell. Biol. 17, 2266-2278; Li, et al., (1996) J. Cell Biol. 132, 849-859; and Moessler, et al. (1996) Development 122, 2415-2425).

Photoreceptor-specific spatially restricted promoters include, but are not limited to, a rhodopsin promoter; a rhodopsin kinase promoter (Young et al. (2003) Ophthalmol. Vis. Sci. 44:4076); a beta phosphodiesterase gene promoter (Nicoud et al. (2007) J. Gene Med. 9:1015); a retinitis pigmentosa gene promoter (Nicoud et al. (2007) supra); an interphotoreceptor retinoid-binding protein (IRBP) gene enhancer (Nicoud et al. (2007) supra); an IRBP gene promoter (Yokoyama et al. (1992) Exp Eye Res. 55:225); and the like.

Methods of introducing a nucleic acid into a host cell are known in the art, and any known method can be used to introduce a nucleic acid (e.g., an expression construct) into a cell. Suitable methods include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

Contacting cells with a guide RNA and/or subject Ago polypeptide and/or 5'-OH generating nuclease may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Conditions that promote the survival of cells are typically permissive of the subject cleavage and binding methods In some embodiments, a subject Ago polypeptide can be codon optimized. In some cases, a codon optimized Ago polypeptide is a variant MpAgo polypeptide. In some cases, a codon optimized Ago polypeptide is a chimeric MpAgo polypeptide. Codon optimization is known in the art and entails the mutation of foreign-derived DNA to mimic the codon preferences of the intended host organism or host cell while encoding the same protein. Thus, the codons are changed, but the encoded protein remains unchanged. For example, if the intended target cell was a human cell, a human codon optimized subject Ago polypeptide (or MpAgo variant) would be a suitable Ago polypeptide. As another non-limiting example, if the intended host cell were a mouse cell, than a mouse codon optimized subject Ago polypeptide (or MpAgo variant, e.g., enzymatically inactive variant) would be a suitable Ago polypeptide. While codon optimization is not required, it is acceptable and may be preferable in certain cases.

In some embodiments, a guide RNA and/or precursor RNA and/or subject Ago polypeptide and/or 5'-OH generating nuclease can be provided as RNA. In such cases, the guide RNA and/or precursor RNA and/or subject Ago polypeptide and/or 5'-OH generating nuclease can be produced by direct chemical synthesis or may be transcribed in vitro from a DNA (e.g., encoding the guide RNA and/or precursor RNA and/or subject Ago polypeptide and/or 5'-OH generating nuclease). Methods of synthesizing RNA from a DNA template are well known in the art. In some cases, the guide RNA and/or precursor RNA and/or subject Ago polypeptide and/or 5'-OH generating nuclease will be synthesized in vitro using an RNA polymerase enzyme (e.g., T7 polymerase, T3 polymerase, SP6 polymerase, etc.). In some cases, (e.g., when a guide RNA is synthesized) a precursor RNA can be first produced and then modified and/or cleaved to generate a suitable guide RNA. Once synthesized, the RNA may directly contact a target nucleic acid or may be introduced into a cell by any of the well-known techniques for introducing nucleic acids into cells (e.g., microinjection, electroporation, transfection, etc).

Nucleotides encoding a subject precursor RNA (introduced either as DNA or RNA) and/or Ago polypeptide (introduced either as DNA or RNA) and/or 5'-OH generating nuclease (introduced either as DNA or RNA) may be provided to the cells using well-developed transfection techniques; see, e.g. Angel and Yanik (2010) PLoS ONE 5(7): e11756, and the commercially available TransMessenger® reagents from Qiagen, Stemfect™ RNA Transfection Kit from Stemgent, and TransIT®-mRNA Transfection Kit from Mirus Bio LLC. See also Beumer et al. (2008), Efficient gene targeting in *Drosophila* by direct embryo injection with zinc-finger nucleases. PNAS 105(50):19821-19826. Alternatively, nucleic acids encoding a precursor RNA and/or subject Ago polypeptide and/or 5'-OH generating nuclease may be provided on DNA vectors. Many vectors, e.g. plasmids, cosmids, minicircles, phage, viruses, etc., useful for transferring nucleic acids into target cells are available. The vectors comprising the nucleic acid(s) may be maintained episomally, e.g. as plasmids, minicircle DNAs, viruses such cytomegalovirus, adenovirus, etc., or they may be integrated into the target cell genome, through homologous recombination or random integration, e.g. retrovirus-derived vectors such as MMLV, HIV-1, ALV, etc.

Vectors may be provided directly to the subject cells. In other words, the cells are contacted with vectors comprising the nucleic acid encoding a precursor RNA and/or subject Ago polypeptide and/or 5'-OH generating nuclease such that the vectors are taken up by the cells. Methods for contacting cells with nucleic acid vectors that are plasmids, including electroporation, calcium chloride transfection, microinjection, and lipofection are well known in the art. For viral vector delivery, the cells are contacted with viral particles comprising the nucleic acid encoding a precursor RNA and/or subject Ago polypeptide and/or 5'-OH generating nuclease. Retroviruses, for example, lentiviruses, are particularly suitable to the method of the invention. Commonly used retroviral vectors are "defective", i.e. unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, this envelope protein determining the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing the retroviral vectors comprising the nucleic acid encoding the reprogramming factors into packaging cell lines and of collecting the viral particles that are generated by the packaging lines are well known in the art. Nucleic acids can also introduced by direct micro-injection (e.g., injection of RNA into a zebrafish embryo, into a gamete, into a single cell of a multicellular organism, etc.).

Vectors used for providing the nucleic acids encoding a precursor RNA and/or subject Ago polypeptide and/or 5'-OH generating nuclease to the subject cells will typically comprise suitable promoters for driving the expression, that is, transcriptional activation, of the nucleic acid of interest. In other words, the nucleic acid of interest will be operably linked to a promoter. This may include ubiquitously acting promoters, for example, the CMV-β-actin promoter, or inducible promoters, such as promoters that are active in particular cell populations or that respond to the presence of drugs such as tetracycline. By transcriptional activation, it is intended that transcription will be increased above basal levels in the target cell by 10 fold, by 100 fold, more usually by 1000 fold. In addition, vectors used for providing a precursor RNA and/or subject Ago polypeptide and/or 5'-OH generating nuclease to the subject cells may include nucleic acid sequences that encode for selectable markers in the target cells, so as to identify cells that have taken up the precursor RNA and/or subject Ago polypeptide and/or 5'-OH generating nuclease A subject guide RNA and/or precursor RNA and/or subject Ago polypeptide and/or 5'-OH generating nuclease may be used to contact DNA or introduced into cells as RNA. Methods of introducing RNA into cells are known in the art and may include, for example, direct injection, transfection, or any other method used for the introduction of DNA.

A subject Ago polypeptide and/or 5'-OH generating nuclease may instead be provided to cells as a polypeptide. Such a polypeptide may optionally be fused to a polypeptide domain that increases solubility of the product. The domain may be linked to the polypeptide through a defined protease cleavage site, e.g. a TEV sequence, which is cleaved by TEV protease. The linker may also include one or more flexible sequences, e.g. from 1 to 10 glycine residues. In some embodiments, the cleavage of the fusion protein is performed in a buffer that maintains solubility of the product, e.g. in the presence of from 0.5 to 2 M urea, in the presence of polypeptides and/or polynucleotides that increase solubility, and the like. Domains of interest include endoosmolytic domains, e.g. influenza HA domain; and other polypeptides that aid in production, e.g. IF2 domain, GST domain, GRPE domain, and the like. The polypeptide may be formulated for improved stability. For example, the peptides may be PEGylated, where the polyethyleneoxy group provides for enhanced lifetime in the blood stream.

Additionally or alternatively, a subject Ago polypeptide and/or 5'-OH generating nuclease may be fused to a polypeptide permeant domain to promote uptake by the cell. A number of permeant domains are known in the art and may be used in the non-integrating polypeptides of the present invention, including peptides, peptidomimetics, and non-peptide carriers. For example, a permeant peptide may be derived from the third alpha helix of Drosophila melanogaster transcription factor Antennapaedia, referred to as penetratin, which comprises the amino acid sequence RQIKIWFQNRRMKWKK (SEQ ID NO: 11). As another example, the permeant peptide comprises the HIV-1 tat basic region amino acid sequence, which may include, for example, amino acids 49-57 of naturally-occurring tat protein. Other permeant domains include poly-arginine motifs, for example, the region of amino acids 34-56 of HIV-1 rev protein, nona-arginine, octa-arginine, and the like. (See, for example, Futaki et al. (2003) Curr Protein Pept Sci. 2003 April; 4(2): 87-9 and 446; and Wender et al. (2000) Proc. Natl. Acad. Sci. U.S.A 2000 Nov. 21; 97(24):13003-8; published U.S. Patent applications 20030220334; 20030083256; 20030032593; and 20030022831, herein specifically incorporated by reference for the teachings of translocation peptides and peptoids). The nona-arginine (R9) sequence is one of the more efficient PTDs that have been characterized (Wender et al. 2000; Uemura et al. 2002). The site at which the fusion is made may be selected in order to optimize the biological activity, secretion or binding characteristics of the polypeptide. The optimal site will be determined by routine experimentation.

A subject Ago polypeptide and/or 5'-OH generating nuclease may be produced in vitro or by eukaryotic cells or by prokaryotic cells, and it may be further processed by unfolding, e.g. heat denaturation, DTT reduction, etc. and may be further refolded, using methods known in the art.

Modifications of interest that do not alter primary sequence include chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Also included in the subject disclosure are guide RNA, precursor RNAs, subject Ago polypeptides, and/or 5'-OH generating nucleases that have been modified using ordinary molecular biological techniques and synthetic chemistry so as to improve their resistance to proteolytic degradation, to change the target sequence specificity, to optimize solubility properties, to alter protein activity (e.g., transcription modulatory activity, enzymatic activity, etc) or to render them more suitable as a therapeutic agent. Analogs of such polypeptides include those containing residues other than naturally occurring L-amino acids, e.g. D-amino acids or non-naturally occurring synthetic amino acids. D-amino acids may be substituted for some or all of the amino acid residues.

The subject Ago polypeptides, and/or 5'-OH generating nucleases may be prepared by in vitro synthesis, using conventional methods as known in the art. Various commercial synthetic apparatuses are available, for example, automated synthesizers by Applied Biosystems, Inc., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The subject Ago polypeptides and/or 5'-OH generating nucleases may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise 20% or more by weight of the desired product, more usually 75% or more by weight, preferably 95% or more by weight, and for therapeutic purposes, usually 99.5% or more by weight, in relation to contaminants related to the method of preparation of the product and its purification. Usually, the percentages will be based upon total protein.

To induce cleavage or any desired modification to a target nucleic acid, or any desired modification to a polypeptide associated with target nucleic acid, the guide RNA and/or precursor RNA and/or subject Ago polypeptide and/or 5'-OH generating nuclease, whether they be introduced as nucleic acids or polypeptides, can be provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g. one time, twice, three times, or more than three times, and the cells allowed to incubate with the agent(s) for some amount of time following each contacting event e.g. 16-24 hours, after which time the media is replaced with fresh media and the cells are cultured further.

In cases in which two or more different targeting complexes are provided to the cell (e.g., two different guide RNAs that are complementary to different sequences within the same or different target nucleic acids), the complexes may be provided simultaneously (e.g. as two polypeptides and/or nucleic acids). Alternatively, they may be provided consecutively, e.g. the targeting complex being provided first, followed by the second targeting complex, etc. or vice versa.

Nucleic Acid Modifications

In some embodiments, a subject nucleic acid (e.g., a guide RNA, a precursor RNA, etc.) has one or more modifications, e.g., a base modification, a backbone modification, etc., to provide the nucleic acid with a new or enhanced feature (e.g., improved stability). A nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Suitable nucleic acid modifications include, but are not limited to: 2' Omethyl modified nucleotides, 2' Fluoro modified nucleotides, locked nucleic acid (LNA) modified nucleotides, peptide nucleic acid (PNA) modified nucleotides, nucleotides with phosphorothioate linkages, and a 5' cap (e.g., a 7-methylguanylate cap (m7G)). Additional details and additional modifications are described below.

A 2'-O-Methyl modified nucleotide (also referred to as 2'-O-Methyl RNA) is a naturally occurring modification of RNA found in tRNA and other small RNAs that arises as a post-transcriptional modification. Oligonucleotides can be directly synthesized that contain 2'-O-Methyl RNA. This modification increases Tm of RNA:RNA duplexes but results in only small changes in RNA:DNA stability. It is stabile with respect to attack by single-stranded ribonucleases and is typically 5 to 10-fold less susceptible to DNases than DNA. It is commonly used in antisense oligos as a means to increase stability and binding affinity to the target message.

2' Fluoro modified nucleotides (e.g., 2' Fluoro bases) have a fluorine modified ribose which increases binding affinity (Tm) and also confers some relative nuclease resistance when compared to native RNA. These modifications are commonly employed in ribozymes and siRNAs to improve stability in serum or other biological fluids.

LNA bases have a modification to the ribose backbone that locks the base in the C3'-endo position, which favors RNA A-type helix duplex geometry. This modification significantly increases Tm and is also very nuclease resistant. Multiple LNA insertions can be placed in an oligo at any position except the 3'-end. Applications have been described ranging from antisense oligos to hybridization probes to SNP detection and allele specific PCR. Due to the large increase in Tm conferred by LNAs, they also can cause an increase in primer dimer formation as well as self-hairpin formation. In some cases, the number of LNAs incorporated into a single oligo is 10 bases or less.

The phosphorothioate (PS) bond (i.e., a phosphorothioate linkage) substitutes a sulfur atom for a non-bridging oxygen in the phosphate backbone of a nucleic acid (e.g., an oligo). This modification renders the internucleotide linkage resistant to nuclease degradation. Phosphorothioate bonds can be introduced between the last 3-5 nucleotides at the 5'- or 3'-end of the oligo to inhibit exonuclease degradation. Including phosphorothioate bonds within the oligo (e.g., throughout the entire oligo) can help reduce attack by endonucleases as well.

In some embodiments, a subject nucleic acid (e.g., a guide RNA, a precursor RNA, etc.) has one or more nucleotides that are 2'-O-Methyl modified nucleotides. In some embodiments, a subject nucleic acid (e.g., a guide RNA, a precursor RNA, etc.) has one or more 2' Fluoro modified nucleotides. In some embodiments, a subject nucleic acid (e.g., a guide RNA, a precursor RNA, etc.) has one or more LNA bases. In some embodiments, a subject nucleic acid (e.g., a guide RNA, a precursor RNA, etc.) has one or more nucleotides that are linked by a phosphorothioate bond (i.e., the subject nucleic acid has one or more phosphorothioate linkages). In some embodiments, a subject nucleic acid (e.g., a precursor RNA) has a 5' cap (e.g., a 7-methylguanylate cap (m7G)). In some embodiments, a subject nucleic acid (e.g., a guide RNA, a precursor RNA, etc.) has a combination of modified nucleotides. For example, a subject nucleic acid (e.g., a precursor RNA) can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

In some embodiments, a subject guide RNA and/or precursor RNA has one or more nucleotides that are 2'-O-Methyl modified nucleotides. In some embodiments, a subject guide RNA and/or precursor RNA has one or more 2' Fluoro modified nucleotides. In some embodiments, a subject guide RNA and/or precursor RNA has one or more LNA bases. In some embodiments, a subject guide RNA and/or precursor RNA has one or more nucleotides that are linked by a phosphorothioate bond (i.e., the subject nucleic acid has one or more phosphorothioate linkages). In some embodiments, a precursor RNA has a 5' cap (e.g., a 7-methylguanylate cap (m7G)). In some embodiments, a subject guide RNA and/or precursor RNA has a combination of modified nucleotides. For example, a subject precursor RNA can have a 5' cap (e.g., a 7-methylguanylate cap (m7G)) in addition to having one or more nucleotides with other modifications (e.g., a 2'-O-Methyl nucleotide and/or a 2' Fluoro modified nucleotide and/or a LNA base and/or a phosphorothioate linkage).

Modified Backbones and Modified Internucleoside Linkages

Examples of suitable nucleic acids containing modifications include nucleic acids containing modified backbones or non-natural internucleoside linkages. Nucleic acids having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids having morpholino backbone structures as described in, e.g., U.S. Pat. No. 5,034,506. For example, in some embodiments, a subject nucleic acid comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat.

No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA). The furanose ring normally present in a DNA/RNA molecule is replaced with a cyclohexenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—$CH_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10° C.), stability towards 3'-exonucleolytic degradation and good solubility properties. Potent and nontoxic antisense oligonucleotides containing LNAs have been described (e.g., Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (e.g., Koshkin et al., Tetrahedron, 1998, 54, 3607-3630). LNAs and preparation thereof are also described in WO 98/39352 and WO 99/14226, as well as U.S. applications 20120165514, 20100216983, 20090041809, 20060117410, 20040014959, 20020094555, and 20020086998.

Modified Sugar Moieties

A subject nucleic acid can also include one or more substituted sugar moieties. Suitable polynucleotides comprise a sugar substituent group selected from: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other suitable polynucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—$CH_2$ $CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further suitable modification includes 2'-dimethylaminooxyethoxy, i.e., a $O(CH_2)_2ON(CH_3)2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)2$.

Other suitable sugar substituent groups include methoxy (—O—$CH_3$), aminopropoxy (—O $CH_2$ $CH_2$ $CH_2NH_2$), allyl (—$CH_2$—CH=$CH_2$), —O-allyl (—O— $CH_2$—CH=$CH_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido(5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Conjugates

Another possible modification of a subject nucleic acid involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.

A conjugate may include a "Protein Transduction Domain" or PTD (also known as a CPP—cell penetrating peptide), which may refer to a polypeptide, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from extracellular space to intracellular space, or cytosol to within an organelle. In some embodiments, a PTD is covalently linked to the amino terminus of an exogenous polypeptide (e.g., a Cas9 polypeptide). In some embodiments, a PTD is covalently linked to the carboxyl terminus of an exogenous polypeptide (e.g., a Cas9 polypeptide). In some embodiments, a PTD is covalently linked to a nucleic acid (e.g., a guide nucleic acid, a polynucleotide encoding a guide nucleic acid, a polynucleotide encoding a Cas9 polypeptide, etc.). Exemplary PTDs include but are not limited to a minimal undecapeptide protein transduction domain (corresponding to residues 47-57 of HIV-1 TAT comprising YGRKKRRQRRR; SEQ ID NO: 12); a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO: 13); Transportan GWTLNSAGYLLGKINLKALAALAKKIL (SEQ ID NO: 14); KALAWEAKLAKALAKA-LAKHLAKALAKALKCEA (SEQ ID NO: 15); and RQIKI-WFQNRRMKWKK (SEQ ID NO: 16). Exemplary PTDs include but are not limited to, YGRKKRRQRRR (SEQ ID NO: 12), RKKRRQRRR (SEQ ID NO: 17); an arginine homopolymer of from 3 arginine residues to 50 arginine residues; Exemplary PTD domain amino acid sequences include, but are not limited to, any of the following: YGRK-KRRQRRR (SEQ ID NO: 12); RKKRRQRR (SEQ ID NO: 18); YARAAARQARA (SEQ ID NO: 19); THRL-PRRRRRR (SEQ ID NO: 20); and GGRRARRRRRR (SEQ ID NO: 9). In some embodiments, the PTD is an activatable CPP (ACPP) (Aguilera et al. (2009) *Integr Biol (Camb)* June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

Methods

The present disclosure provides methods for cleaving a single stranded target nucleic acid (and/or modifying a polypeptide associated with a single stranded target nucleic acid). The present disclosure provides methods for binding a single stranded target nucleic acid (and/or modifying a polypeptide associated with a single stranded target nucleic acid). Generally, a subject method of cleaving involves contacting a single stranded target nucleic acid with (e.g., by introducing into a cell) a subject guide RNA and a subject Ago polypeptide (e.g., a wild type MpAgo polypeptide, a variant MpAgo polypeptide, a variant MpAgo polypeptide with reduced nuclease activity, etc.). Generally, a subject method of binding involves contacting a single stranded target nucleic acid with (e.g., by introducing into a cell), a guide RNA and a subject Ago polypeptide (e.g., a variant Cas9 polypeptide, a chimeric MpAgo polypeptide, a mutant MpAgo polypeptide with reduced nuclease activity, etc.).

In some embodiments of the subject methods, the target nucleic acid is inside of a cell (which can be referred to as a "host cell" or a "target cell"). In some cases, the method involves contacting a cell with (e.g., introducing into a cell) a guide RNA (or a precursor RNA or a nucleic acid encoding the same), and/or a subject Ago polypeptide (or a nucleic acid encoding the same). In some embodiments of the subject methods, the host cell provides one or more of the components (e.g., the cell can be genetically modified to express a subject Ago polypeptide and/or a guide RNA and/or a precursor RNA and/or a 5'-OH generating nuclease). In some such cases, the methods therefore include adding those components not provided by the host cell. For example, if the host cell is genetically modified to express a subject Ago polypeptide, the method can include introducing into the cell a guide RNA and/or a precursor RNA (which would therefore constitute a method of contacting a target nucleic acid with a subject Ago polypeptide, a guide RNA, and/or a precursor RNA).

As discussed above, a subject guide RNA and a subject Ago polypeptide form a complex. The guide RNA provides target specificity to the complex by comprising a nucleotide sequence that is complementary to a sequence of a target nucleic acid. The subject Ago polypeptide of the complex provides the site-specific activity (e.g., nuclease activity). In some embodiments, a subject complex cleaves a target single stranded nucleic acid. In some embodiments, a subject complex binds a target single stranded nucleic acid. In some cases, the subject Ago polypeptide exhibits nuclease activity that cleaves target nucleic acid at a target sequence (target site) defined by the region of complementarity between the guide RNA and the target nucleic acid.

In some embodiments, when the method is a method of binding, the target nucleic acid can be contacted with a variant MpAgo polypeptide (e.g., a mutant MpAgo polypeptide that has reduced nuclease activity, as described above). Such a variant MpAgo polypeptide can still bind to target nucleic acids in a sequence-specific manner, but the binding does not necessarily result in cleavage of the target nucleic acid (e.g, if the mutant MpAgo polypeptide has no substantial nuclease activity, e.g., a mutant MpAgo polypeptide harboring a D516A mutation). Thus, methods of binding can be used to visualize, image, isolate, collect, and/or analyze single stranded target nucleic acids in a sequence-specific manner. A subject Ago polypeptide (e.g., a variant MpAgo polypeptide that has reduced nuclease activity) can bind to a single stranded target nucleic acid in the presence of a guide RNA.

In some cases, in addition to contacting a target nucleic acid with a guide RNA, a variant MpAgo polypeptide (e.g., with reduced nuclease activity) (which produces a variant-MpAgo polypeptide/target nucleic acid complex), a subject method further includes isolating the variant-MpAgo polypeptide/target nucleic acid complex, and collecting and/or analyzing a single stranded target nucleic acid and/or a polypeptide (or polypeptides) associated with a single stranded target nucleic acid. In some cases, the method includes, prior to collecting and/or analyzing, releasing the single stranded target nucleic acid from the complex. In some cases, the variant-MpAgo polypeptide/target nucleic acid complex, once formed, self dissociates. For example, in some cases, the variant MpAgo polypeptide has a fusion partner (e.g., a fusion partner having enzymatic activity) that modifies the target nucleic acid, and once modified the variant-MpAgo polypeptide/target nucleic acid complex dissociates.

A variant-MpAgo polypeptide/target nucleic acid complex can be isolated by any convenient method. For example, the complex can be isolated by immunoprecipitation (e.g., using an antibody against the subject Ago polypeptide and/or using a labeled subject Ago polypeptide) (various labels are described above). As one non-limiting example, the subject Ago polypeptide can be labeled with biotin then immobilized on a solid support (e.g. agarose-streptavidin), and the RNA can be isolated and/or analyzed (e.g., via column chromatography, via RNA purification and sequencing, etc.). In some cases, the target nucleic acid will also be bound by other nucleic acids and/or proteins there were present prior to contacting with a subject Ago polypeptide. In some such cases, after a subject binding method is performed, the target nucleic acid remains bound to the other nucleic acids and/or proteins (e.g., proteins and/or nucleic acids of a cell that normally interact with the target nucleic acid). As such, a subject binding method can be used to study the molecules (e.g., nucleic acids and/or proteins) that interact with any target nucleic acid of interest.

In addition, a method of binding can be used to visualize the target nucleic acid (e.g., visualize the subcellular distribution of a target nucleic acid, visualize single stranded regions of a double stranded DNA molecule, etc.). Because the Ago polypeptide/guide RNA forms a complex at a targeted site of a target single stranded nucleic acid, any one of the components (the subject Ago polypeptide, the guide RNA) can be detectably labeled (i.e., can have an indirect and/or direct label moiety, defined above) in order to visualize the complex. The term "detectable label" includes directly and/or indirectly detectable labels. In some cases, a guide RNA (and/or a precursor RNA) can have a label moiety that can be indirectly detected (an RNA aptamer, a nucleic acid sequence that is bound by a labeled protein, biotin, etc.) and/or directly detected (e.g., a fluorescent dye).

In some instances, one or more components (e.g, a target nucleic acid, a guide RNA, and/or a subject Ago polypeptide) is labeled with (e.g., linked to) a donor molecule, while another component is labeled with (e.g., linked to) an acceptor molecule, and detection of an association between the labeled components is by fluorescence resonance energy transfer (also referred to as "Förster resonance energy transfer" or "FRET").

FRET is phenomenon wherein excitation of one emissive dye is transferred to another without emission of a photon. A FRET pair consists of a donor chromophore and an acceptor chromophore (where the acceptor chromophore may be a quencher molecule). The emission spectrum of the donor and the absorption spectrum of the acceptor must overlap, and the two molecules must be in close proximity. The distance between donor and acceptor at which 50% of donors are deactivated (transfer energy to the acceptor) is defined by the Förster radius, which is typically 10-100 angstroms. Changes in the emission spectrum comprising FRET pairs can be detected, indicating changes in the number of that are in close proximity (i.e., within 100 angstroms of each other). This will typically result from the binding or dissociation of two molecules, one of which is labeled with a FRET donor and the other of which is labeled with a FRET acceptor, wherein such binding brings the FRET pair in close proximity.

Binding of such molecules will result in an increased emission of the acceptor and/or quenching of the fluorescence emission of the donor. FRET pairs (donor/acceptor) suitable for use include, but are not limited to, EDANS/fluorescein, IAEDANS/fluorescein, fluorescein/tetramethylrhodamine, fluorescein/Cy 5, IEDANS/DABCYL, fluorescein/QSY-7, fluorescein/LC Red 640, fluorescein/Cy 5.5 and fluorescein/LC Red 705. In addition, a fluorophore/quantum dot donor/acceptor pair can be used. EDANS is (5-((2-Aminoethyl)amino)naphthalene-1-sulfonic acid); IAEDANS is 5-({2-[(iodoacetyl)amino]ethyl}amino)naphthalene-1-sulfonic acid); DABCYL is 4-(4-dimethylaminophenyl) diazenylbenzoic acid.

Cy3, Cy5, Cy 5.5, and the like, are cyanines. For example, Cy3 and Cy5 are reactive water-soluble fluorescent dyes of the cyanine dye family. Cy3 dyes are red (~550 nm excitation, ~570 nm emission and therefore appear green), while Cy5 is fluorescent in the red region (~650/670 nm) but absorbs in the orange region (~649 nm). Alexa Fluor dyes, Dylight, IRIS Dyes, Seta dyes, SeTau dyes, SRfluor dyes and Square dyes can also be used.

In another aspect of FRET, an emissive donor molecule and a nonemissive acceptor molecule ("quencher") may be employed. In this application, emission of the donor will increase when quencher is displaced from close proximity to the donor and emission will decrease when the quencher is brought into close proximity to the donor. Useful quenchers include, but are not limited to, DABCYL, QSY 7 and QSY 33. Useful fluorescent donor/quencher pairs include, but are not limited to EDANS/DABCYL, Texas Red/DABCYL, BODIPY/DABCYL, Lucifer yellow/DABCYL, coumarin/DABCYL and fluorescein/QSY 7 dye.

In some instances, one or more components (e.g., a target nucleic acid, a guide RNA, a subject Ago polypeptide, and/or a precursor RNA) is labeled with (e.g., linked to, fused with, bound by, etc.) a first member of a split fluorophore, while another component is labeled with (e.g., linked to, fused with, bound by, etc.) a second member of a split fluorophore, and detection of the fluorophore can occur when the first and second split fluorophores are brought into close proximity. For example, in some cases, one component (a subject Ago polypeptide, a guide RNA) can be labeled with a first member of a split fluorophore and the other component can be labeled with a second member of the split fluorophore such that, when the Ago polypeptide/guide RNA complex is formed (the components are brought into close proximity), a signal can be detected. Any convenient split fluorophore can be used. For more information related to split fluorophores (e.g., a split-GFP), refer to Cabantous et al., Sci Rep. 2013 Oct. 4; 3:2854. doi: 10.1038/srep02854, which is hereby incorporated by reference in its entirety.

Multiple Guide RNAs

In some embodiments, multiple guide RNAs and/or multiple precursor RNAs are used to simultaneously cleave and/or bind multiple different target nucleic acids or multiple different locations on the same target nucleic. For example, for methods of binding, each guide RNA and/or precursor RNA can have a detectable label that is distinguishable from another guide RNA and/or precursor RNA, and thus, multiple different target nucleic acids can be simultaneously bound (e.g., visualized). In some embodiments, two or more guide RNAs and/or precursor RNAs target the same gene or transcript or locus. In some embodiments, two or more guide RNAs and/or precursor RNAs target different unrelated target nucleic acids. In some embodiments, two or more guide RNAs and/or precursor RNAs target different, but related target nucleic acids.

Because the guide RNAs and/or precursor RNAs can be small and robust, multiple guide RNAs and/or precursor RNAs can be simultaneously present on the same expression vector and can even be under the same transcriptional control if so desired. In some embodiments, two or more (e.g., 3 or more, 4 or more, 5 or more, 10 or more, 15 or more, 20 or more, 25 or more, 30 or more, 35 or more, 40 or more, 45 or more, or 50 or more) guide RNAs and/or precursor RNAs are simultaneously expressed in a target cell (from the same or different vectors).

To express multiple guide RNAs, an artificial RNA processing system mediated by a nuclease (e.g., the Csy4 endoribonuclease) can be used. Multiple guide RNAs can be concatenated into a tandem array on a precursor transcript (e.g., expressed from a U6 promoter), and separated by nuclease specific cleavage sites (e.g., a Csy4-specific RNA sequence). In some such cases, a cleave site can be positioned 5' of each targeting sequence and/or 3' of each targeting sequence such that multiple guide RNAs (e.g., each with a 5'-OH) can be generated from the same precursor RNA. Thus, when the appropriate nuclease (e.g., csy4) is co-expressed, the nuclease cleaves the precursor transcript into multiple guide RNAs. Advantages for using an RNA processing system include: (i) there is no need to use multiple promoters; and (ii) since all guide RNAs are processed from a precursor transcript, their concentrations are normalized for similar Ago-binding.

Csy4 is a small endoribonuclease (RNase) protein derived from bacteria *Pseudomonas aeruginosa*. Csy4 specifically recognizes a minimal 17-bp RNA hairpin, and exhibits rapid (<1 min) and highly efficient (>99.9% or more) RNA cleavage. Unlike most RNases, the cleaved RNA fragment remains stable and functionally active. The Csy4-based RNA cleavage can be repurposed into an artificial RNA processing system. In this system, the 17-bp RNA hairpins are inserted between multiple RNA fragments that are transcribed as a precursor transcript from a single promoter. Co-expression of Csy4 is effective in generating individual RNA fragments.

In some embodiments (e.g., in some cases where the subject Ago polypeptide is a chimeric MpAgo polypeptide), a subject complex modifies a target polypeptide associated with target nucleic acid (e.g., a histone, a DNA-binding protein, an RNA-binding protein, an RNA editing protein etc.), leading to, for example, protein methylation, protein acetylation, protein ubiquitination, and the like. The target nucleic acid may be, for example, a single stranded nucleic acid outside of a cell in vitro, a single stranded nucleic acid inside of a cell in vitro, a single stranded nucleic acid inside of a cell ex vivo, or a single stranded nucleic acid inside of a cell in vivo. In some cases, the nuclease activity of the subject Ago polypeptide cleaves single stranded target nucleic acid, causing degradation of, and a reduction in the levels of, the target nucleic acid.

In some embodiments, a subject guide RNA and a subject Ago polypeptide are used as an inducible system for shutting off gene expression in cells. For example, in some cases, nucleic acids encoding an appropriate guide RNA (as a precursor RNA) and/or an appropriate subject Ago polypeptide and/or an appropriate 5'-OH generating nuclease (for cleaving a precursor RNA) can be incorporated into the chromosome of a target cell and are under control of an inducible promoter. When the guide RNA (as a precursor RNA) and/or an appropriate subject Ago polypeptide and/or an appropriate 5'-OH generating nuclease are induced, the target nucleic acid is cleaved (or otherwise modified) at the location of interest, when the guide RNA and the subject Ago polypeptide are present and bind the single stranded target nucleic acid. As such, in some cases, cells are engineered to include nucleic acid sequences encoding an appropriate subject Ago polypeptide in the genome and/or an appropriate guide RNA (as a precursor RNA) (e.g., on a plasmid, e.g., under control of an inducible promoter), allowing experiments in which the expression of any targeted gene (expressed from a separate plasmid introduced into the cell) could be controlled by inducing expression of the guide RNA and/or the subject Ago polypeptide. Any of the components can be provided as an RNA.

In some cases, a subject Ago polypeptide has enzymatic activity that modifies target nucleic acid in ways other than introducing strand cleavage. Enzymatic activity of interest that may be used to modify target nucleic acid (e.g., by fusing a heterologous polypeptide with enzymatic activity to a subject Ago polypeptide, thereby generating a chimeric MpAgo polypeptide) includes, but is not limited methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity).

In some cases, the subject Ago polypeptide has activity that modulates the production of a protein encoded by a single stranded target nucleic acid (e.g., mRNA) (e.g., by cleaving and thereby degrading the mRNA). In some cases, the subject method is used to cleave a targeted coding-RNA (protein-encoding gene) and/or a targeted non-coding RNA (e.g., tRNA, rRNA, snoRNA, siRNA, miRNA, long ncRNA, etc.).

In some cases, the subject Ago polypeptide has enzymatic activity that modifies a polypeptide associated with a target nucleic acid (e.g. a histone, a DNA-binding protein, an RNA-binding protein, an RNA editing protein, a single stranded nucleic acid binding protein, and the like). In some embodiments, the enzymatic activity is methyltransferase activity, demethylase activity, acetyltransferase activity, deacetylase activity, kinase activity, phosphatase activity, ubiquitin ligase activity (i.e., ubiquitination activity), deubiquitinating activity, adenylation activity, deadenylation activity, SUMOylating activity, deSUMOylating activity, ribosylation activity, deribosylation activity, myristoylation activity, demyristoylation activity glycosylation activity (e.g., from O-GlcNAc transferase) or deglycosylation activity. The enzymatic activities listed herein catalyze covalent modifications to proteins. Such modifications are known in the art to alter the stability or activity of the target protein (e.g., phosphorylation due to kinase activity can stimulate or silence protein activity depending on the target protein).

Target Cells of Interest

In some of the above applications, the subject methods may be employed to induce target nucleic acid cleavage, target nucleic acid modification, and/or to bind target nucleic acids (e.g., for visualization, for collecting and/or analyzing, etc.) in mitotic or post-mitotic cells in vivo and/or ex vivo and/or in vitro (e.g., to disrupt production of a protein encoded by a targeted mRNA). Because the guide RNA provides specificity by hybridizing to target nucleic acid, a mitotic and/or post-mitotic cell of interest in the disclosed methods may include a cell from any organism (e.g. a bacterial cell, an archaeal cell, a cell of a single-cell eukaryotic organism, a plant cell, an algal cell, e.g., *Botryococcus braunii, Chlamydomonas reinhardtii, Nannochloropsis gaditana, Chlorella pyrenoidosa, Sargassum patens C. Agardh*, and the like, a fungal cell (e.g., a yeast cell), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal, a cell from a rodent, a cell from a human, etc.).

Any type of cell may be of interest (e.g. a stem cell, e.g. an embryonic stem (ES) cell, an induced pluripotent stem (iPS) cell, a germ cell; a somatic cell, e.g. a fibroblast, a hematopoietic cell, a neuron, a muscle cell, a bone cell, a hepatocyte, a pancreatic cell; an in vitro or in vivo embryonic cell of an embryo at any stage, e.g., a 1-cell, 2-cell, 4-cell, 8-cell, etc. stage zebrafish embryo; etc.). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro. Target cells are in many embodiments unicellular organisms, or are grown in culture.

If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, phosphate-buffered saline (PBS), Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% or more DMSO, 50% or more serum, and about 40% buffered medium, or some other such solution as is commonly used in the art to preserve cells at such freezing temperatures, and thawed in a manner as commonly known in the art for thawing frozen cultured cells.

Introducing Components into a Target Cell

A guide RNA (or a nucleic acid comprising a nucleotide sequence encoding same), a precursor RNA (or a nucleic acid comprising a nucleotide sequence encoding same), a 5'-OH generating nuclease (or a nucleic acid comprising a nucleotide sequence encoding same), and/or a subject Ago polypeptide (or a nucleic acid comprising a nucleotide sequence encoding same) can be introduced into a host cell by any of a variety of well-known methods. Similarly, where a subject method involves introducing into a host cell a nucleic acid comprising a nucleotide sequence encoding a subject Ago polypeptide, such a nucleic acid can be introduced into a host cell by any of a variety of well-known methods.

Methods of introducing a nucleic acid into a host cell are known in the art, and any known method can be used to introduce a nucleic acid (e.g., an expression construct) into a stem cell or progenitor cell. Suitable methods include, include e.g., viral or bacteriophage infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et., al Adv Drug Deliv Rev. 2012 Sep. 13. pii: S0169-409X(12)00283-9. doi: 10.1016/j.addr.2012.09.023), and the like.

For methods of cleaving and/or binding a single stranded target nucleic acid, in some cases, the subject Ago polypeptide and/or 5'-OH generating nuclease is provided as a nucleic acid (e.g., an mRNA, a DNA, a plasmid, an expression vector, etc.) that encodes the Ago or 5'-OH generating protein. In some cases, the subject Ago polypeptide and/or 5'-OH generating nuclease is provided directly as a protein. As one non-limiting example, fungi (e.g., yeast) can be transformed with exogenous protein and/or nucleic acid using spheroplast transformation (see Kawai et al., Bioeng Bugs. 2010 November-December; 1(6):395-403: "Transformation of *Saccharomyces cerevisiae* and other fungi: methods and possible underlying mechanism"; and Tanka et al., Nature. 2004 Mar. 18; 428(6980):323-8: "Conformational variations in an infectious protein determine prion strain differences"; both of which are herein incorporated by reference in their entirety). Thus, a subject Ago polypeptide and/or a 5'-OH generating nuclease can be incorporated into a spheroplast (with or without a guide RNA, a precursor RNA, and/or a DNA encoding a precursor RNA) and the spheroplast can be used to introduce the content into a yeast cell. A subject Ago polypeptide and/or a 5'-OH generating nuclease can be introduced into a cell (provided to the cell) by any convenient method; such methods are known to those of ordinary skill in the art. As another non-limiting example, a subject Ago polypeptide and/or a 5'-OH generating nuclease can be injected directly into a cell (e.g., with or without a guide RNA, a precursor RNA, and/or a DNA encoding a precursor RNA), e.g., a cell of a zebrafish embryo, the pronucleus of a fertilized mouse oocyte, etc.

Genetically Modified Host Cells

In some embodiments, a genetically modified host cell has been genetically modified with an exogenous nucleic acid comprising a nucleotide sequence encoding a subject Ago polypeptide (e.g., a naturally occurring MpAgo; a modified, i.e., mutated or variant, MpAgo; a chimeric MpAgo; etc.) and/or a 5'-OH generating nuclease. Single stranded nucleic acids of the genetically modified host cell can be targeted for modification by introducing into the cell a guide RNA (e.g., as a an RNA molecule, as a precursor RNA, or as a DNA encoding a precursor RNA). In some embodiments, the nucleotide sequence encoding a subject Ago polypeptide and/or 5'-OH generating nuclease is operably linked to an inducible promoter (e.g., heat shock promoter, Tetracycline-regulated promoter, Steroid-regulated promoter, Metal-regulated promoter, estrogen receptor-regulated promoter, etc.). In some embodiments, the nucleotide sequence encoding a subject Ago polypeptide and/or 5'-OH generating nuclease is operably linked to a spatially restricted and/or temporally restricted promoter (e.g., a tissue specific promoter, a cell type specific promoter, etc.). In some embodiments, the nucleotide sequence encoding a subject Ago polypeptide and/or 5'-OH generating nuclease is operably linked to a constitutive promoter.

In some embodiments, a subject genetically modified host cell is in vitro. In some embodiments, a subject genetically modified host cell is in vivo. In some embodiments, a subject genetically modified host cell is a prokaryotic cell or is derived from a prokaryotic cell. In some embodiments, a subject genetically modified host cell is a bacterial cell or is derived from a bacterial cell. In some embodiments, a subject genetically modified host cell is an archaeal cell or is derived from an archaeal cell. In some embodiments, a subject genetically modified host cell is a eukaryotic cell or is derived from a eukaryotic cell. In some embodiments, a subject genetically modified host cell is a plant cell or is derived from a plant cell. In some embodiments, a subject genetically modified host cell is an animal cell or is derived from an animal cell. In some embodiments, a subject genetically modified host cell is an invertebrate cell or is derived from an invertebrate cell. In some embodiments, a subject genetically modified host cell is a vertebrate cell or is derived from a vertebrate cell. In some embodiments, a subject genetically modified host cell is a mammalian cell or is derived from a mammalian cell. In some embodiments, a subject genetically modified host cell is a rodent cell or is derived from a rodent cell. In some embodiments, a subject genetically modified host cell is a human cell or is derived from a human cell.

The present disclosure further provides progeny of a subject genetically modified cell, where the progeny can comprise the same exogenous nucleic acid or polypeptide as the subject genetically modified cell from which it was derived. The present disclosure further provides a composition comprising a subject genetically modified host cell.

In other aspects of the disclosure, a guide RNA and/or a precursor RNA and/or a subject Ago polypeptide and/or a 5'-OH generating nuclease are employed to modify single stranded nucleic acid (ssRNA, ssDNA) in vivo, for purposes such as gene therapy, e.g. to treat a disease or as an antiviral, antipathogenic, or anticancer therapeutic, or for biological research. In in vivo embodiments, a guide RNA and/or a precursor RNA and/or a subject Ago polypeptide and/or a 5'-OH generating nuclease are administered directly to an individual. A guide RNA and/or a precursor RNA and/or a subject Ago polypeptide and/or a 5'-OH generating nuclease may be administered by any of a number of well-known methods in the art for the administration of peptides, small molecules and nucleic acids to a subject. A guide RNA and/or a precursor RNA and/or a subject Ago polypeptide and/or a 5'-OH generating nuclease can be incorporated into a variety of formulations. More particularly, a guide RNA and/or a precursor RNA and/or a subject Ago polypeptide and/or a 5'-OH generating nuclease of the present invention can be formulated into pharmaceutical compositions by combination with appropriate pharmaceutically acceptable carriers or diluents.

Pharmaceutical preparations are compositions that include one or more of: a guide RNA and/or a precursor RNA and/or a subject Ago polypeptide and/or a 5'-OH generating nuclease present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the a guide RNA and/or a precursor RNA and/or a subject Ago polypeptide and/or a 5'-OH generating nuclease can be achieved in various ways, including oral, buccal, rectal, parenteral, intraperitoneal, intradermal, transdermal, intratracheal, intraocular, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversibly affixed (see e.g. US Application Nos. 20080081064 and 20090196903, incorporated herein by reference).

Typically, an effective amount of a guide RNA and/or a precursor RNA and/or a subject Ago polypeptide and/or a 5'-OH generating nuclease are provided. As discussed above with regard to ex vivo methods, an effective amount or effective dose of a guide RNA and/or a precursor RNA and/or a subject Ago polypeptide and/or a 5'-OH generating nuclease in vivo is the amount to induce a 2 fold (or greater) reduction in the amount of intact target nucleic acid (for methods of cleaving) relative to a negative control, e.g. a cell contacted with an empty vector or irrelevant polypeptide. The amount of intact target nucleic acid may be measured by any convenient method, e.g. as described above and known in the art. The calculation of the effective amount or effective dose of a guide RNA and/or a precursor RNA and/or a subject Ago polypeptide and/or a 5'-OH generating nuclease to be administered is within the skill of one of ordinary skill in the art. The final amount to be administered will be dependent upon the route of administration and upon the nature of the disorder or condition that is to be treated.

The effective amount given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, a guide RNA and/or a precursor RNA and/or a subject Ago polypeptide and/or a 5'-OH generating nuclease may be obtained from a suitable commercial source. As a general proposition, the total pharmaceutically effective amount of a guide RNA and/or a precursor RNA and/or a subject Ago polypeptide and/or a 5'-OH generating nuclease administered parenterally per dose will be in a range that can be measured by a dose response curve.

Therapies based on a guide RNA and/or a precursor RNA and/or a subject Ago polypeptide and/or a 5'-OH generating nuclease, i.e. preparations of a guide RNA and/or a precursor RNA and/or a subject Ago polypeptide and/or a 5'-OH generating nuclease to be used for therapeutic administration, must be sterile. Sterility is readily accomplished by filtration through sterile filtration membranes (e.g., 0.2 µm membranes). Therapeutic compositions generally are placed into a container having a sterile access port, for example, an intravenous solution bag or vial having a stopper pierceable by a hypodermic injection needle. The therapies based on a guide RNA and/or a precursor RNA and/or a subject Ago polypeptide and/or a 5'-OH generating nuclease may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., National Food (NF) grade, generally analytical grade, and more typically pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Compositions

The present invention provides a composition comprising a subject guide RNA and a subject Ago polypeptide. In some cases, the subject Ago polypeptide is a variant MpAgo polypeptide. In some cases, the subject Ago polypeptide is a chimeric MpAgo polypeptide. In some cases, the subject Ago polypeptide is a mutant MpAgo polypeptide. A subject composition is useful for carrying out a method of the present disclosure, e.g., a method for cleaving a single stranded target nucleic acid; a method for binding a single stranded target nucleic acid; etc.

Compositions Comprising a Guide Nucleic Acid

The present invention provides a composition comprising a subject guide RNA and/or a precursor RNA and/or a subject Ago polypeptide (or nucleic acid encoding the same). The composition can comprise, in addition, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), MES sodium salt, 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a nuclease inhibitor; and the like. For example, in some cases, a subject composition comprises a subject guide RNA and a buffer for stabilizing nucleic acids.

In some embodiments, a subject guide RNA and/or precursor RNA and/or a subject Ago polypeptide present in a subject composition is pure, e.g., 75% or more, 80% or more, 85% or more, 90% or more, 95% or more, 98% or more, 99% or more, or more than 99% or more pure, where "% or more purity" means that the subject guide RNA and/or precursor RNA and/or a subject Ago polypeptide is the recited percent free from other macromolecules, or contaminants that may be present during the production of the guide RNA and/or precursor RNA and/or a subject Ago polypeptide.

Kits and Libraries

The present disclosure provides kits for carrying out a subject method. A subject kit can include one or more of (e.g., two or more, three or more, or all four): a subject Ago polypeptide (or a nucleic acid, e.g., RNA, DNA, encoding the same); a guide RNA; a precursor RNA (or a DNA encoding the same); and a 5'-OH generating nuclease, all of which are described in detail above. A kit may include a complex that includes a subject Ago polypeptide and a guide RNA.

A subject kit can include one or more recombinant expression vectors. A subject recombinant expression vector can include nucleotide sequences encoding a subject Ago polypeptide and/or a subject precursor RNA. In some cases, a subject recombinant expression vector includes a nucleotide sequence encoding a 5'-OH generating nuclease.

In some cases, a subject recombinant expression vector includes an insert region (e.g., a multiple cloning site, e.g., a site having sequences that allow for the insertion of a sequence using any of a large number of convenient methods for genetic engineering) that is positioned 3' of the cleavage site and allows for the insertion of a targeting nucleotide sequence of interest. As such, an insert region allows for the insertion of a targeting sequence while the recombinant expression vector provides the nucleic acid means for expressing the targeting sequence in a precursor RNA, which can be modified and/or cleaved to produce a guide RNA (as described above). As such, in some cases, a recombinant expression vector includes a cleavage site (for a ribozyme and/or for a 5'-OH generating nuclease) near an insert region (e.g., 5' of the insert region) such that a user can insert a targeting sequence of interest and the recombinant expression vector will provide the appropriate nucleic acid sequences for the production of a precursor RNA (which can then be cleaved to produce a subject guide RNA) (e.g., see description of a precursor RNA (e.g., cleavage sites) above). In some cases, a recombinant expression vector includes a cleavage site for a ribozyme near an insert region (e.g., 5' of the insert region), and ribozyme sequences such that a user can insert a targeting sequence of interest and the recombinant expression vector will provide the appropriate nucleic acid sequences for the production of a precursor RNA that can self-cleave to generate a guide RNA. Thus, in some cases, a subject recombinant expression vector includes an insert region for the insertion of a targeting sequence of interest, and a nucleotide sequence encoding a subject Ago polypeptide (e.g., a wild type MpAgo polypeptide, a variant MpAgo polypeptide, etc.). In some cases, a subject recombinant expression vector includes an insert region for the insertion of a targeting sequence of interest; a nucleotide sequence encoding a subject Ago polypeptide (e.g., a wild type MpAgo polypeptide, a variant MpAgo polypeptide, etc.); and a nucleotide sequence encoding a 5'-OH generating nuclease.

In some embodiments of any of the above kits, the kit includes a guide RNA. In some embodiments of any of the above kits, the kit includes a precursor RNA. In some embodiments of any of the above kits, the kit includes a subject Ago polypeptide. In some embodiments of any of the above kits, the kit comprises a 5'-OH generating nuclease. In some embodiments of any of the above kits, the kit includes two or more guide RNAs. In some embodiments of any of the above kits, the kit includes two or more precursor RNAs. In some embodiments of any of the above kits, a guide RNA (e.g., including two or more guide RNAs) and/or a precursor RNA (e.g., including two or more precursor RNAs) can be provided as an array (e.g., an array of RNA molecules, an array of DNA molecules, e.g., encoding the guide RNA(s) and/or precursor RNA(s), etc.). Such kits can be useful, for example, for use in conjunction with the above described genetically modified host cells that comprise a subject Ago polypeptide. Components of a subject kit can be in separate containers; or can be combined in a single container.

Any of the above-described kits can further include one or more additional reagents, where such additional reagents can be selected from: a dilution buffer; a reconstitution solution; a wash buffer; a control reagent; a control expression vector or RNA polynucleotide; a reagent for in vitro production of a subject Ago polypeptide and/or 5'-OH generating nuclease from DNA, and the like. In some cases, a subject kit comprises a variant MpAgo polypeptide that exhibits reduced nuclease activity relative to wild-type MpAgo. In some cases, a subject kit comprises a nucleic acid comprising a nucleotide sequence encoding a variant MpAgo polypeptide that exhibits reduced nuclease activity relative to wild-type MpAgo. In some cases, a subject kit comprises a nucleic acid comprising a nucleotide sequence encoding a variant MpAgo polypeptide that exhibits a different 5' guide preference (e.g., with respect to preference toward a guide RNA with a 5'-OH or a 5'-phosphate, with respect to the degree of preference, etc.) relative to wild-type MpAgo.

A subject kit can further include one or more additional reagents, where such additional reagents can be selected from: a buffer; a wash buffer; a control reagent; a control expression vector or RNA polynucleotide; a reagent for in vitro production of a subject Ago polypeptide and/or 5'-OH generating nuclease from DNA; and the like. In some cases, a subject Ago polypeptide included in a subject kit is a wild type MpAgo polypeptide. In some cases, a subject Ago polypeptide included in a subject kit is a variant MpAgo polypeptide. In some cases, a subject Ago polypeptide included in a subject kit is a chimeric MpAgo polypeptide. In some cases, a subject Ago polypeptide included in a subject kit is a mutant MpAgo polypeptide.

Components of a subject kit can be in separate containers; or can be combined in a single container.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The present disclosure provides a library of two or more guide RNAs and/or precursor RNAs. The guide RNAs and/or precursor RNAs can be present in the library as RNA molecules or as DNA molecules (e.g., recombinant expression vectors) comprising nucleotides encoding precursor RNAs. A subject library can comprise from 2 to $10^{12}$ guide RNAs and/or precursor RNAs (e.g., from 2 to $10^2$, from $10^2$ to $10^3$, from $10^3$ to $10^5$, from $10^5$ to $10^7$, from $10^7$ to $10^9$, or from $10^9$ to $10^{12}$) where the targeting sequences of at least two guide RNAs and/or precursor RNAs of the library are different.

Utility

A method for cleaving and/or binding a single-stranded target nucleic acid according to the present disclosure finds use in a variety of applications, which are also provided. Applications include research applications; diagnostic applications; industrial applications; and treatment applications. Applications include, e.g., determining the effect (e.g., in a target cell) of reducing the presence of a target nucleic acid (e.g., mRNA, tRNA, rRNA, microRNA, ncRNA, lncRNA, etc.) (i.e., target-selected and target-specific RNA degradation); and/or treating an individual by degrading a particular targeted single stranded DNA or single stranded RNA.

As described above, applications also include (e.g., when using a binding method to visualize a target nucleic acid) the visualization and subcellular localization of specific single stranded target nucleic acids (e.g., in real time) (e.g., multicolor RNA imaging inside of a cell). Also as described above, applications include (e.g., when using a binding method to collect and/or analyze single stranded target nucleic acid) RNA-protein pulldown assays from living cells (e.g., in vitro, ex vivo, and/or in vivo). As described above, applications include (e.g., when a binding method is used to isolate and/or collect and/or analyze target nucleic acid) the identification of target nucleic acid-associated proteins (e.g., via mass spectrometry analysis), or even purification of intact target RNA:protein complexes and subsequent biochemical or biophysical studies.

A subject cleaving method can be used for drug discovery and target validation. High through-put genomic analysis can be carried out using a subject cleaving method. A library (e.g., a subject library) comprising a plurality of nucleic acids used in the genomic analysis can include, for example: a promoter operably linked to a precursor RNA-encoding nucleotide sequence, where each nucleic acid can include a different targeting sequence, and in some cases, common cleavage sites. A library (e.g., a subject library) comprising a plurality of nucleic acids used in the genomic analysis can include, for example: a guide RNA (e.g., already including a 5'-OH), or a precursor RNA, where each guide RNA and/or precursor RNA can include a different targeting sequence, and in some cases, common cleavage sites (e.g., multiple precursor RNAs can have the same cleavage sites in order to facilitate cleavage and production of guide RNAs). Applications include large-scale phenotyping and gene-to-function mapping.

In addition, targeting sequences of multiple guide RNAs can be designed such that cleavage of a target nucleic acid can result in double strand break (e.g., if two targeted single stranded nucleic acids are on opposite strands of a single-stranded region of dsDNA). Such a method can be used for genome editing akin to the use of a Cas9 polypeptide (e.g., described in international patent application WO2013176772, which is hereby incorporated by reference in its entirety).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Figure 1C:
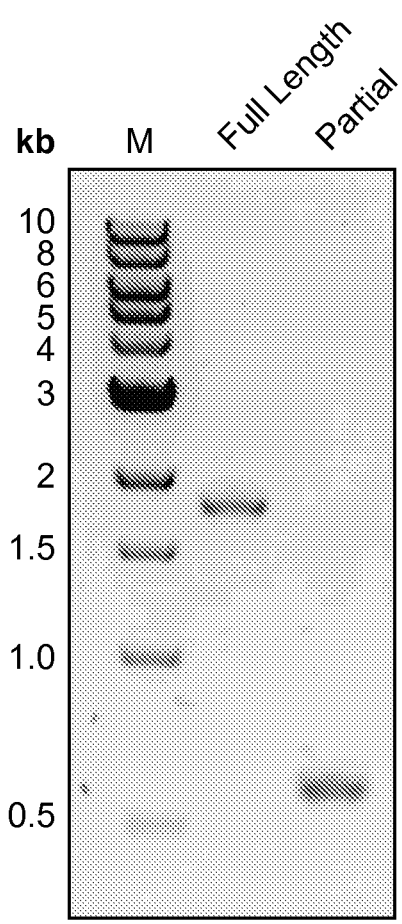

Sequence analysis of the recently discovered extremophile bacterium *Marinitoga piezophila* identified a subtype III-B CRISPR/Cas locus in its genome, which encodes an Argonaute protein (FIG. 1A). Sequence alignments with other Argonaute proteins revealed that the gene encodes for a full-length Argonaute, including the Piwi nuclease domain and the catalytically essential DEDX motif (FIG. 1B). Furthermore, RNA extraction and reverse transcription PCR (RT-PCR) shows that the protein is actively produced in *M. piezophila* (FIG. 1C). Highly specific polyclonal antibodies were produced by immunizing a rabbit with recombinant full length protein (FIG. 2D).

Figure 1D:
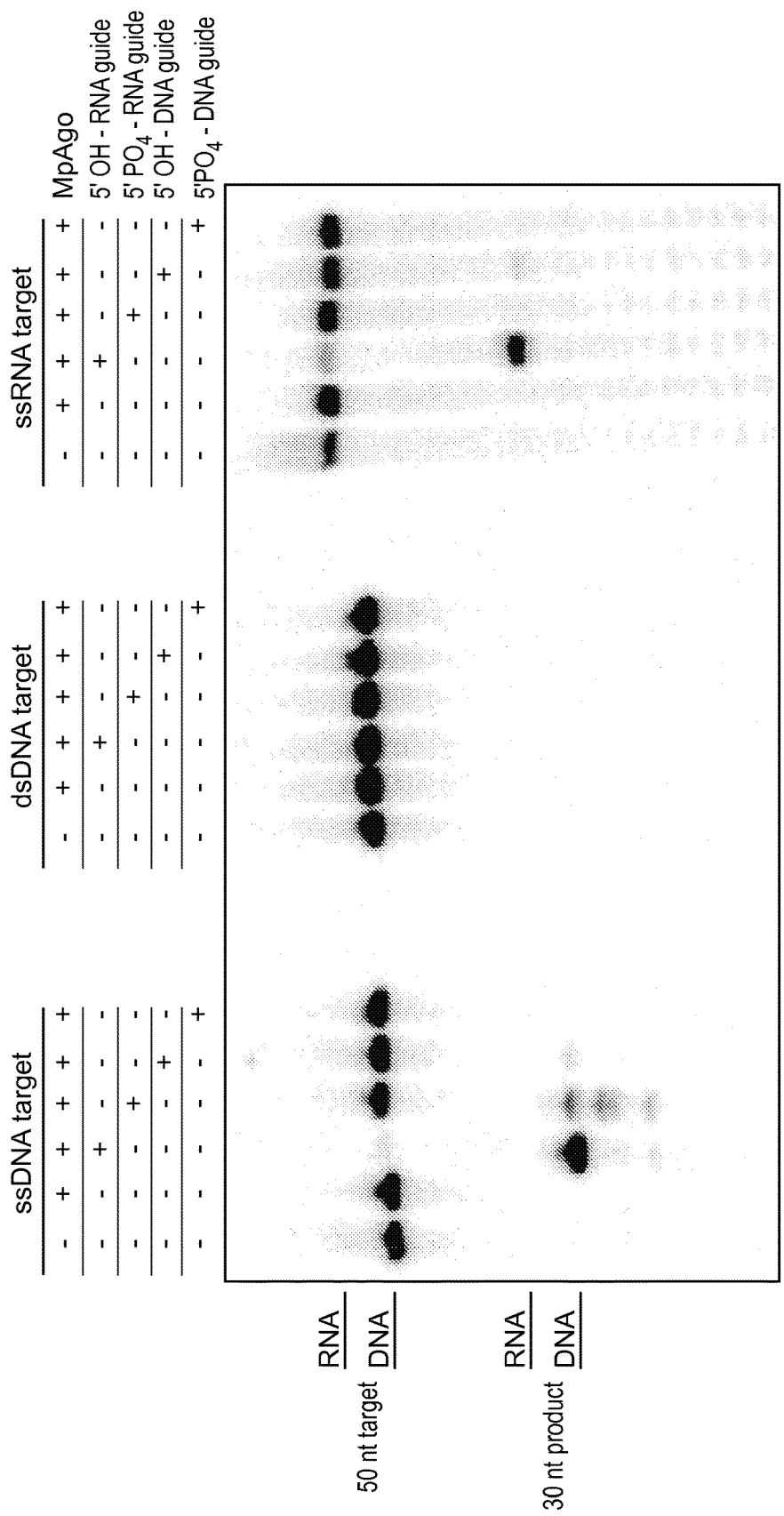
Figure 1E:
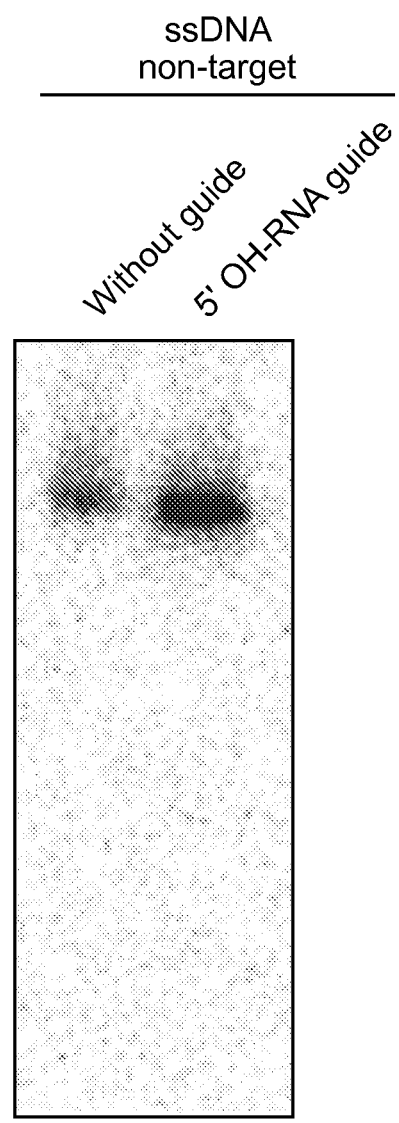

For the biochemical characterization of *M. piezophila* argonaute (MpAgo), the wild type protein was recombinantly expressed in *E. coli* and purified. The enzyme was then programmed with 21 nt DNA or RNA guides and used in cleavage assays with various target nucleic acids (FIG. 1D). MpAgo preferentially used RNA guides with a 5'-OH and not, as seen for all other argonaute (Ago) proteins so far investigated, guides with a 5'-$PO_4$ (5'-phosphate) (FIG. 1D, FIG. 2A, FIG. 2B). In these experiments the highest activity was observed for RNA guided ssDNA cleavage followed by ssRNA cleavage, while no cleavage was observed for dsDNA targets. To show that the cleavage is based on sequence complementarity between the 5'-OH RNA guide and the target strand, cleavage experiments were performed with a non-complimentary guide DNA. As presented in FIG. 1E, no target cleavage could be observed when MpAgo was reconstituted with a non-complimentary guide.

FIG. 1. (A) Representation of the subtype III-b CRISPR/Cas locus of *Marinitoga piezophila* KA3 (Accession number NC_016751.1). The CRISPR/Cas locus is composed of two putative cas operons flanked by three CRISPR arrays. One cas operon encodes a primase small α-subunit like protein, Cas1, Cas2, and an Argonaute protein. A second operon, which is located at the opposite strand, encodes the Cmr complex (Cmr1-6), the endonuclease Cas6, and the proteins Csx1 and Csm6. The three CRISPR arrays consist of a highly conserved leader sequence followed by identical repeats (R; greens rectangles) interspersed with different spacers (S; blue rectangles); (B) Sequence alignment of the PIWI domains (ClustalW2 algorithm, ClustalX color code) comparing human Ago2 (residues 579-859 of SEQ ID NO:26), *Drosophila* Ago1 (residues 703-984 of SEQ ID NO:27), *M. piezophila* Ago (MpAgo) (residues 423-639 of SEQ ID NO:1), *Thermus thermophilus* Ago (TtAgo) (residues 461-685 or SEQ ID NO:28), and *Pyrococcus furiosus* (PfAgo) (residues 541-770 of SEQ ID NO: 29). The DEDX motif residues, which are essential for endonuclease activity, are conserved in slicer active Argonaute proteins and are highlighted with red frames and dots; (C) Reverse transcription PCR (RT-PCR) of *M. piezophila* cDNA was performed using primers to amplify full length MpAgo (2000 bp) and the last 670 bp of the gene. The PCR reactions were separated using 1% Agarose gel electrophoresis and visualized via SYBR safe staining. The expected fragments for MpAgo mRNA could be detected, showing that MpAgo is being actively transcribed in the cell; (D) In vitro cleavage experiments using reconstituted MpAgo with either (1) 5'-OH RNA guide, (2) 5'-$PO_4$ RNA guide, (3) 5'-OH DNA guide, or (4) 5'-$PO_4$ DNA guide. The length of the guides used was 21 nt and is reverse complement to a sequence within a 5'-radiolabeled 50 nt RNA or DNA target. MpAgo preferentially uses a 5'-OH RNA guide to cleave a ssRNA or ssDNA target at the $10^{th}$ nucleotide counting from the 5'-end of the guide, resulting in a 30 nt 5'-radiolabeled cleavage product. No cleavage was observed for dsDNA target; (E) In vitro cleavage experiments using reconstituted MpAgo with a 5'-OH RNA guide that has no basepair complementarity to the target ssDNA does not cleave the target. This shows that MpAgo is a sequence specific, RNA guided ssRNA/ssDNA endonuclease.

FIGS. 2. (A) and (B) MpAgo preferentially cleaves ssDNA in the presence of a 5'-OH RNA guide. Substantial cleavage was also observed for ssRNA cleavage in the presence of the 5'-OH RNA guide. A decreased cleavage activity was observed for MpAgo reconstituted with 5'-$PO_4$ DNA-guide targeting ssDNA. No activity could be detected for DNA-guided ssDNA cleavage experiments. Shown are kinetic cleavage experiments using reconstituted MpAgo with the guides (1)-(4) to target ssRNA (A) or ssDNA (B). Reconstituted MpAgo was incubated with 5'-radiolabeled targets at 60° C. and reactions were quenched at different time points using 2×RNA loading dye supplemented with 20 mM EDTA. The reactions were separated by 12% denaturing PAGE and visualized via phosphoimaging. (C) MpAgo is a multiple turnover enzyme, as known for other Argonaute proteins. Reconstituted MpAgo was incubated with a 5-fold excess of ssDNA and ssRNA target. The reactions were resolved on a 12% denaturing PAGE and visualized via phosphoimaging. The results were analyzed using ImageQuant (GE Healthcare) and the data fitted with KaleidaGraph (SYNERGY Software) to exponential decay. (D) Recombinant MpAgo produced in *E. coli* was used to immunize a rabbit. The rabbit serum containing polyclonal antibodies was then tested in Western Blots against *E. coli* cell lysate without MpAgo and lysate containing $His_6$-MBP-tagged MpAgo.

Figure 3C:
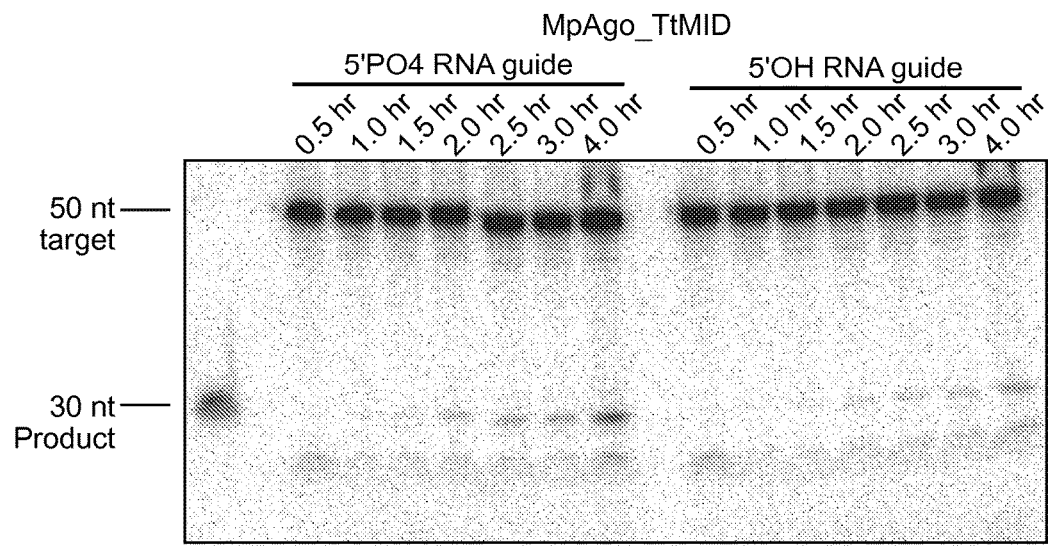
Figure 3D:
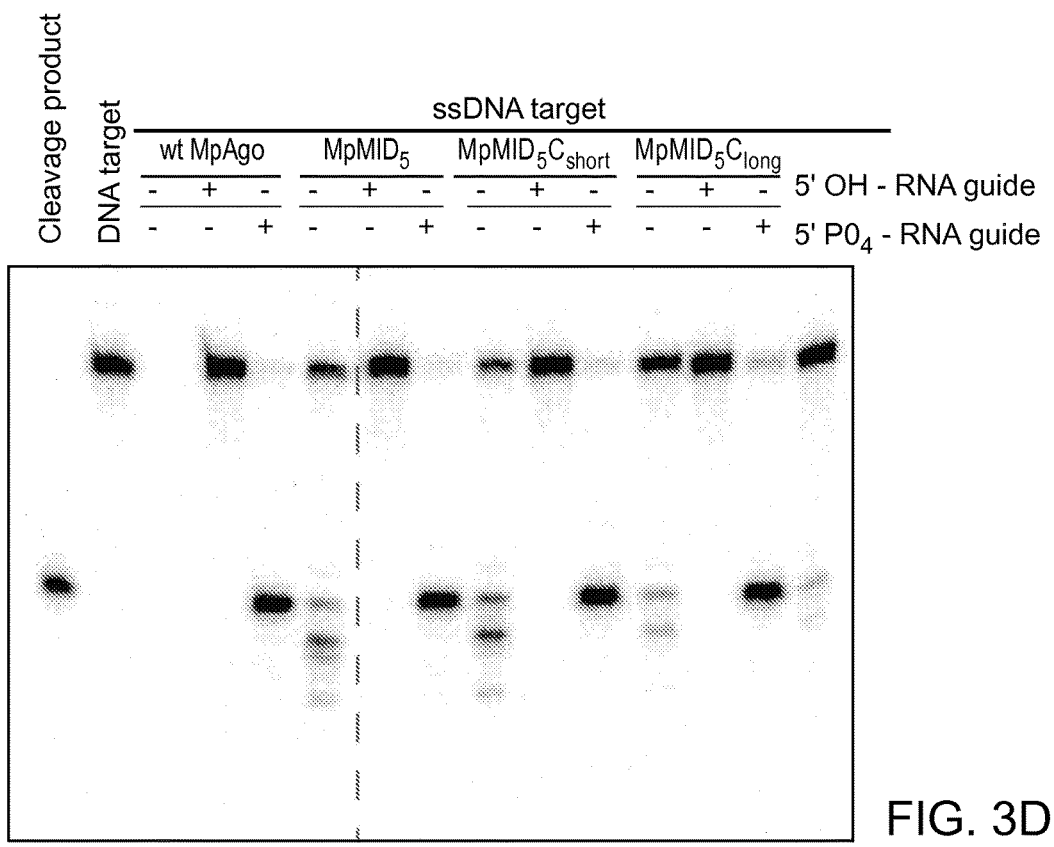

In order to investigate the 5'-guide end preference of MpAgo, an alignment of the MID domain of MpAgo with other, well characterized Agos was performed (FIG. 3A, B). The MID domain of Agos is known to provide the 5'-binding pocket of the guide strand. The alignment clearly shows differences between MpAgo and the other Agos at residues in the MID domain that are involved in binding of the guide 5'-$PO_4$. To test whether these differences in the MID domain are responsible for the altered 5'-end binding preference of MpAgo, we exchanged the MID domain of MpAgo with the MID domain of *Thermus thermophilus* Ago (TtAgo). The chimeric Ago (MpAgo_TtMID) was successfully cloned, expressed in *E. coli*, and purified. In cleavage assays, MpAgo_TtMID showed an overall reduced activity compared to the wildtype protein (FIG. 3C). Nonetheless, the chimeric protein was able to use the 5'-phosphorylated and 5'-hydroxyl RNAs with the same efficiency for sequence specific target cleavage. In an effort to investigate the 5' binding pocket in more detail, we introduced point mutations into the MID-domain that are conserved in other Agos but altered in MpAgo. A C-terminal loop that is also conserved among other Agos but missing in MpAgo was introduced and tested together with the MID domain mutations (FIG. 3D). None of these mutations were able to convert the 5'-OH binding preference of MpAgo to a more canonical 5'-phosphate binding preference. The ability of MpAgo to recognize RNAs with a 5'-OH is of particular interest, since the hydroxyl group at the 5'-end is a conserved property of crRNAs.

FIG. 3. (A) Sequence alignment including the MID domains (ClustalW2 algorithm, ClustalX color code) comparing human Ago2 (residues 453-619 of SEQ ID NO:26), *Drosophila* Ago1 (residues 577-743 of SEQ ID NO:27), MpAgo (residues 312-467 of SEQ ID NO:1), TtAgo (residues 371-498 or SEQ ID NO:28), and PfAgo (SEQ ID NO: 30). Residues that have been shown in the TtAgo:DNA: DNA co-crystal structure (B; PDB 3HM9) to be involved in 5' phosphate binding are marked with a black dot. The alignment reveals mutations in the MpAgo MID domain of conserved residues (highlighted with red dots). Furthermore, the crystal structure shows interactions with non-polar residues at the C-terminus of TtAgo with the 5'-binding pocket; (C) The MID domain of MpAgo was exchanged with the TtAgo MID domain (MpAgo_TtMID) and tested in time course cleavage experiments. Herein, ssDNA target was incubated with a 250-fold excess of reconstituted MpAgo_TtMID (5'-OH RNA and 5'-$PO_4$ RNA guide, respectively). Overall, the test MID domain exchange mutant enzyme is less active than the wildtype MpAgo based on the intensity of the cleavage product band, but utilizes both guides for targeted cleave; (D) Conserved mutations were introduced into the MID domain of MpAgo based on the alignment in FIG. 3A. The mutations were tested either alone or in combination with two different C-terminal extensions mimicking the C-terminus of TtAgo (+4 and +9 amino acids). All mutants retained wildtype activity with the 5'-OH RNA guide and no increased preference for a 5'-$PO_4$ RNA guide. "$MpMID_5$" (SEQ ID NO: 23) is MpAgo (SEQ ID NO: 1) with mutations I363F/E367K/D392S/N393Q/D406R; "$MpMID_5C_{short}$" (SEQ ID NO: 24) is MpAgo (SEQ ID NO: 1) with mutations I363F/E367K/D392S/N393Q/D406R plus an LFFV (SEQ ID NO: 21) extension at the C-terminus; "$MpMID_5C_{long}$" (SEQ ID NO: 25) is MpAgo (SEQ ID NO: 1) with mutations I363F/E367K/D392S/N393Q/D406R+VDREKLFFV (SEQ ID NO: 22) extension at C-terminus.

To test whether the nuclease activity of MpAgo could be reduced by amino acid mutation, a D516A mutation was made because D516 is one of the four amino acids predicted to be part of the catalytic triad of the DEDX motif of MpAgo (FIG. 1). In this assay, 1 nM wild type and mutant (D516A) MpAgo were reconstituted with equimolar amounts of different 21 nt guides for 30 min at 37° C. and tested in a cleavage reaction with a 50 nt complementary ssDNA target (0.1 nM). The cleavage reaction was conducted at 60° C. for 1 h. the reaction was resolved on 12% denaturing PAGE and visualized via phosphoimaging (Storm, GE Healthcare). The data show that the D516A mutation abolished the nuclease activity of MpAgo (FIG. 4).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of binding a single stranded target nucleic acid, the method comprising:
   contacting the single stranded target nucleic acid with:
   (i) an argonaute (Ago) polypeptide comprising (a) an amino-terminal domain (N-domain), (b) a PIWI/Argonaute/Zwille (PAZ) domain, (c) a MID domain, and (d) a PIWI domain,
   wherein the MID domain comprises an amino acid sequence having 80% or more sequence identity with amino acids 282-430 of the wild type Marinitoga piezophila argonaute (MpAgo) amino acid sequence set forth in SEQ ID NO: 1, and/or the PIWI domain comprises an amino acid sequence having 80% or more sequence identity with amino acids 431-639 of the amino acid sequence set forth in SEQ ID NO: 1,
   wherein the Ago polypeptide is a mutant MpAgo polypeptide that, compared to the wild type MpAgo protein set forth in SEQ ID NO: 1, comprises an amino acid sequence having one or more mutations and exhibits reduced nuclease activity; and
   (ii) a guide RNA comprising a targeting nucleotide sequence of 15 to 35 nucleotides (nt) in length that is complementary to a target sequence of the target nucleic acid.

2. The method according to claim 1, wherein the guide RNA comprises a 5'-OH.

3. The method according to claim 1, wherein the length of the guide RNA is in a range of from 15 to 30 nucleotides.

4. The method according to claim 1, wherein the length of the targeting nucleotide sequence of the guide RNA is in a range of from 15 to 30 nucleotides.

5. The method according to claim 1, wherein the targeting nucleotide sequence of the guide RNA has 70% or more complementarity to the target sequence of the target nucleic acid over 15 or more contiguous nucleotides.

6. The method according to claim 1, wherein the single stranded target nucleic acid is inside of a cell.

7. The method according to claim 6, wherein the cell is a prokaryotic cell.

8. The method according to claim 6, wherein the cell is a eukaryotic cell.

9. The method according to claim 6, wherein contacting the target nucleic acid with the Ago polypeptide comprises introducing the Ago polypeptide into the cell, or introducing into the cell a nucleic acid encoding the Ago polypeptide.

10. The method according to claim 1, wherein the mutant MpAgo polypeptide comprises an amino acid sequence having a substitution or deletion in one or more amino acid positions selected from: D446, E482, D516, and N624 compared to the wild type MpAgo protein set forth in SEQ ID NO: 1.

11. A recombinant expression vector comprising a nucleotide sequence that encodes:
   an argonaute (Ago) polypeptide comprising (a) an amino-terminal domain (N-domain), (b) a PIWI/Argonaute/Zwille (PAZ) domain, (c) a MID domain, and (d) a PIWI domain,
   wherein the MID domain comprises an amino acid sequence having 80% or more sequence identity with amino acids 282-430 of the wild type *Marinitoga piezophila* argonaute (MpAgo) amino acid sequence set forth in SEQ ID NO: 1, and/or the PIWI domain comprises an amino acid sequence having 70% or more sequence identity with amino acids 431-639 of the amino acid sequence set forth in SEQ ID NO: 1.

12. The recombinant expression vector of claim 11, wherein the Ago polypeptide is:
   (i) a mutant MpAgo polypeptide that, compared to the wild type MpAgo protein set forth in SEQ ID NO: 1, comprises an amino acid sequence having one or more mutations and exhibits reduced nuclease activity; or
   (ii) a chimeric MpAgo polypeptide comprising a fusion partner having an amino acid sequence that provides for a modification of the target nucleic acid other than cleavage.

13. The recombinant expression vector of claim 11, further comprising a nucleotide sequence that encodes a guide RNA that comprises a targeting nucleotide sequence of 15 to 35 nucleotides (nt) in length that is complementary to a target sequence of a single stranded target nucleic acid.

14. The recombinant expression vector of claim 13, wherein the guide RNA comprises a 5'-OH.

15. A method of modifying a single stranded target nucleic acid, the method comprising:
   contacting the single stranded target nucleic acid with:
   A) a fusion polypeptide comprising:
      a) an argonaute (Ago) polypeptide comprising: (i) an amino-terminal domain (N-domain), (ii) a PIWI/Argonante/Zwille (PAZ) domain, (iii) a MID domain, and (iv) a PIWI domain,
      wherein the MID domain comprises an amino acid sequence having 80% or more sequence identity with amino acids 282-430 of the wild type *Marinitoga piezophila* argonaute (MpAgo) amino acid sequence set forth in SEQ ID NO: 1, and/or the PIWI domain comprises an amino acid sequence having 80% or more sequence identity with amino acids 431-639 of the amino acid sequence set forth in SEQ ID NO: 1; and
      b) a fusion partner having an amino acid sequence that provides for a modification of the target nucleic acid other than cleavage; and
   B) a guide RNA comprising a targeting nucleotide sequence of 15 to 35 nucleotides (nt) in length that is complementary to a target sequence of the target nucleic acid.

16. The method according to claim 15, wherein the guide RNA comprises a 5'-OH.

17. The method according to claim 15, wherein the length of the guide RNA is in a range of from 15 to 30 nucleotides.

18. The method according to claim 15, wherein the length of the targeting nucleotide sequence of the guide RNA is in a range of from 15 to 30 nucleotides.

19. The method according to claim 15, wherein the targeting nucleotide sequence of the guide RNA has 70% or more complementarity to the target sequence of the target nucleic acid over 15 or more contiguous nucleotides.

20. The method according to claim 15, wherein the single stranded target nucleic acid is inside of a cell.

21. The method according to claim 20, wherein the cell is a prokaryotic cell.

22. The method according to claim 20, wherein the cell is a eukaryotic cell.

23. The method according to claim 20, wherein contacting the target nucleic acid with the Ago polypeptide comprises introducing the Ago polypeptide into the cell, or introducing into the cell a nucleic acid encoding the Ago polypeptide.

24. A kit, comprising:
   an argonaute (Ago) polypeptide, or a nucleic acid encoding the same, wherein the Ago polypeptide comprises (a) an amino-terminal domain (N-domain), (b) a PIWI/Argonaute/Zwille (PAZ) domain, (c) a MID domain, and (d) a PIWI domain,
   wherein the MID domain comprises an amino acid sequence having 80% or more sequence identity with amino acids 282-430 of the wild type *Marinitoga piezophila* argonaute (MpAgo) amino acid sequence set forth in SEQ ID NO: 1, and/or the PIWI domain comprises an amino acid sequence having 70% or more sequence identity with amino acids 431-639 of the amino acid sequence set forth in SEQ ID NO: 1, wherein the Ago polypeptide is a mutant MpAgo polypeptide that, compared to the wild type MpAgo protein set forth in SEQ ID NO: 1, comprises an amino acid sequence having one or more mutations and exhibits reduced nuclease activity.

25. The kit of claim 24, wherein the guide RNA comprises a 5'-OH.

26. The kit of claim 25, further comprising a 5'-OH generating nuclease or nucleic acid encoding the same.

27. The kit of claim 24, further comprising a nucleotide sequence that encodes a guide RNA that comprises a targeting nucleotide sequence of 15 to 35 nucleotides (nt) in length that is complementary to a target sequence of a single stranded target nucleic acid.

28. A kit, comprising:
a fusion polypeptide comprising:
a) an argonaute (Ago) polypeptide comprising: (i) an amino-terminal domain (N-domain), (ii) a PIWI/Argonaute/Zwille (PAZ) domain, (iii) a MID domain, and (iv) a PIWI domain,
wherein the MID domain comprises an amino acid sequence having 80% or more sequence identity with amino acids 282-430 of the wild type Marinitoga piezophila argonaute (MpAgo) amino acid sequence set forth in SEQ ID NO: 1, and/or the PIWI domain comprises an amino acid sequence having 80% or more sequence identity with amino acids 431-639 of the amino acid sequence set forth in SEQ ID NO: 1; and
b) a fusion partner having an amino acid sequence that provides for a modification of the target nucleic acid other than cleavage.

29. The kit of claim 28, wherein the guide RNA comprises a 5'-OH.

30. The kit of claim 29, further comprising a 5'-OH generating nuclease or nucleic acid encoding the same.

31. The kit of claim 28, further comprising a nucleotide sequence that encodes a guide RNA that comprises a targeting nucleotide sequence of 15 to 35 nucleotides (nt) in length that is complementary to a target sequence of a single stranded target nucleic acid.

* * * * *

UNITED STATES PATENT AND TRADEMARK OFFICE
CERTIFICATE OF CORRECTION

PATENT NO. : 10,253,311 B2
APPLICATION NO. : 15/129382
DATED : April 9, 2019
INVENTOR(S) : Doudna et al.

Page 1 of 1

It is certified that error appears in the above-identified patent and that said Letters Patent is hereby corrected as shown below:

Column 20, Line 14, should read:
U per unit dose, e.g., from about 100,000 U to about Column 20, Line 17, should read:
U to about 800,000 U per unit dose. In some embodiments, Column 38, Line 25, should read:
steroids as asthma therapy). Allergy to bakers/brewers yeast, Column 38, Line 43, should read:
with scores in the ≤ 3$^{rd}$ percentile in all areas tested, dem- Column 39, Line 2, should read:
calculated at the 99th percentile, and speech therapy was Column 39, under TABLE 1 header "Example 2", should read:
Impact of Vitamin E and Omega 3 Supplementation in Children with Verbal Apraxia Column 40, Line 50, should read:
3. Antigliadin IgG antibodies: High in 15/19 (79%)

Signed and Sealed this
Twentieth Day of August, 2019

Andrei Iancu
*Director of the United States Patent and Trademark Office*

SEQUENCE LISTING

```
<160> NUMBER OF SEQ ID NOS: 30

<210> SEQ ID NO 1
<211> LENGTH: 639
<212> TYPE: PRT
<213> ORGANISM: Marinitoga piezophila

<400> SEQUENCE: 1

Met Tyr Leu Asn Leu Tyr Lys Ile Asp Ile Pro Lys Lys Ile Lys Arg
1               5                   10                  15

Leu Tyr Phe Tyr Asn Pro Asp Met Glu Pro Lys Leu Phe Ala Arg Asn
            20                  25                  30

Leu Ser Arg Val Asn Asn Phe Lys Phe Gln Asp Ser Asn Asp Leu Val
        35                  40                  45

Trp Ile Glu Ile Pro Asp Ile Asp Phe Gln Ile Thr Pro Lys Asn Val
    50                  55                  60
```

Phe Gln Tyr Lys Val Glu Lys Glu Ile Ile Lys Glu Glu Asp
65                  70                  75                  80

Lys Lys Leu Phe Val Lys Thr Leu Tyr Lys Tyr Ile Lys Lys Leu Phe
            85                  90                  95

Leu Asp Asn Asp Phe Tyr Phe Lys Lys Gly Asn Asn Phe Ile Ser Asn
                100                 105                 110

Ser Glu Val Phe Ser Leu Asp Ser Asn Glu Asn Val Asn Ala His Leu
        115                 120                 125

Thr Tyr Lys Ile Lys Ile His Asn Ile Ser Asn Glu Tyr Tyr Leu Ser
    130                 135                 140

Ile Leu Pro Lys Phe Thr Phe Leu Ser Lys Glu Pro Ala Leu Glu Ser
145                 150                 155                 160

Ala Ile Lys Ser Gly Tyr Leu Tyr Asn Ile Lys Ser Gly Lys Ser Phe
                165                 170                 175

Pro Tyr Ile Ser Gly Leu Asp Gly Ile Leu Lys Ile Asp Ile Gly Asn
                180                 185                 190

Asn Gln Ile Val Glu Val Ala Tyr Pro Glu Asn Tyr Leu Phe Asn Phe
        195                 200                 205

Thr Thr Arg Asp Ala Glu Lys Tyr Gly Phe Ser Lys Glu Val His Glu
    210                 215                 220

Ile Tyr Lys Asn Lys Val Phe Glu Gly Phe Lys Lys Ile Pro Lys Thr
225                 230                 235                 240

Leu Gly Phe Leu Asn Lys Ile Thr Asn Leu Asn Glu Asn Tyr Gln Leu
                245                 250                 255

Lys Asp Gly Tyr Lys Ile Phe Ile Asn Val Ile Tyr Lys Phe Lys Asn
                260                 265                 270

Gly Glu Ser Arg Tyr Ala Lys Asp Val Phe Lys Tyr Ser Phe Tyr Lys
        275                 280                 285

Asn Glu Gln Pro Leu Lys Ala Ile Phe Phe Ser Ser Lys Lys Gln
    290                 295                 300

Phe Phe Glu Val Gln Lys Ser Leu Lys Glu Leu Phe His Asn Lys His
305                 310                 315                 320

Ser Val Phe Tyr Arg Ala Ala Ala Glu Leu Gly Phe Ser Lys Val Glu
                325                 330                 335

Phe Leu Arg Asp Ser Lys Thr Lys Ser Ser Ala Phe Leu Tyr Asn Pro
        340                 345                 350

Glu Glu Phe Thr Val Lys Asn Thr Glu Phe Ile Asn Gln Ile Glu Asp
    355                 360                 365

Asn Val Met Ala Ile Val Leu Leu Asp Lys Tyr Ile Gly Asn Ile Asp
370                 375                 380

Pro Leu Val Arg Asn Phe Pro Asp Asn Leu Ile Leu Gln Pro Ile Leu
385                 390                 395                 400

Lys Glu Lys Leu Glu Asp Ile Lys Pro Phe Ile Ile Lys Ser Tyr Val
                405                 410                 415

Tyr Lys Met Gly Asn Phe Ile Pro Glu Cys Lys Pro Phe Ile Leu Lys
                420                 425                 430

Lys Met Glu Asp Lys Glu Lys Asn Leu Tyr Ile Gly Ile Asp Leu Ser
        435                 440                 445

His Asp Thr Tyr Ala Arg Lys Thr Asn Leu Cys Ile Ala Ala Val Asp
    450                 455                 460

Asn Thr Gly Asp Ile Leu Tyr Ile Gly Lys His Lys Asn Leu Glu Leu
465                 470                 475                 480

Asn Glu Lys Met Asn Leu Asp Ile Leu Glu Lys Glu Tyr Ile Lys Ala

```
                    485                 490                 495
Phe Glu Lys Tyr Ile Glu Lys Phe Asn Val Ser Pro Glu Asn Val Phe
                500                 505                 510

Ile Leu Arg Asp Gly Arg Phe Ile Glu Asp Ile Glu Ile Ile Lys Asn
            515                 520                 525

Phe Ile Ser Tyr Asn Asp Thr Lys Tyr Thr Leu Val Glu Val Asn Lys
        530                 535                 540

Asn Thr Asn Ile Asn Ser Tyr Asp Asp Leu Lys Glu Trp Ile Ile Lys
545                 550                 555                 560

Leu Asp Glu Asn Thr Tyr Ile Tyr Tyr Pro Lys Thr Phe Leu Asn Gln
                565                 570                 575

Lys Gly Val Glu Val Lys Ile Leu Glu Asn Asn Thr Asp Tyr Thr Ile
                580                 585                 590

Glu Glu Ile Ile Glu Gln Ile Tyr Leu Leu Thr Arg Val Ala His Ser
            595                 600                 605

Thr Pro Tyr Thr Asn Tyr Lys Leu Pro Tyr Pro Leu His Ile Ala Asn
        610                 615                 620

Lys Val Ala Leu Thr Asp Tyr Glu Trp Lys Leu Tyr Ile Pro Tyr
625                 630                 635

<210> SEQ ID NO 2
<211> LENGTH: 109
<212> TYPE: PRT
<213> ORGANISM: Artificial sequence
<220> FEATURE:
<223> OTHER INFORMATION: Synthetic amino acid sequence

<400> SEQUENCE: 2

Met Tyr Leu Asn Leu Tyr Lys Ile Asp Ile Pro Lys Lys Ile Lys Arg
1               5                   10                  15

Leu Tyr Phe Tyr Asn Pro Asp Met Glu Pro Lys Leu Phe Ala Arg Asn
            20                  25                  30

Leu Ser Arg Val Asn Asn Phe Lys Phe Gln Asp Ser Asn Asp Leu Val
        35                  40                  45

Trp Ile Glu Ile Pro Asp Ile Asp Phe Gln Ile Thr Pro Lys Asn Val
    50                  55                  60

Phe Gln Tyr Lys Val Glu Lys Glu Ile Ile Lys Glu Glu Glu Asp
65                  70                  75                  80

Lys Lys Leu Phe Val Lys Thr Leu Tyr Lys Tyr Ile Lys Lys Leu Phe
                85                  90                  95

Leu Asp Asn Asp Phe Tyr Phe Lys Lys Gly Asn Asn Phe
            100                 105

<210> SEQ ID NO 3
<211> LENGTH: 43
<212> TYPE: PRT
<213> ORGANISM: Artificial sequence
<220> FEATURE:
<223> OTHER INFORMATION: Synthetic amino acid sequence

<400> SEQUENCE: 3

Ile Ser Asn Ser Glu Val Phe Ser Leu Asp Ser Asn Glu Asn Val Asn
1               5                   10                  15

Ala His Leu Thr Tyr Lys Ile Lys Ile His Asn Ile Ser Asn Glu Tyr
            20                  25                  30

Tyr Leu Ser Ile Leu Pro Lys Phe Thr Phe Leu
        35                  40
```

```
<210> SEQ ID NO 4
<211> LENGTH: 60
<212> TYPE: PRT
<213> ORGANISM: Artificial sequence
<220> FEATURE:
<223> OTHER INFORMATION: Synthetic amino acid sequence

<400> SEQUENCE: 4

Ser Lys Glu Pro Ala Leu Glu Ser Ala Ile Lys Ser Gly Tyr Leu Tyr
1               5                   10                  15

Asn Ile Lys Ser Gly Lys Ser Phe Pro Tyr Ile Ser Gly Leu Asp Gly
            20                  25                  30

Ile Leu Lys Ile Asp Ile Gly Asn Asn Gln Ile Val Glu Val Ala Tyr
        35                  40                  45

Pro Glu Asn Tyr Leu Phe Asn Phe Thr Thr Arg Asp
    50                  55                  60

<210> SEQ ID NO 5
<211> LENGTH: 69
<212> TYPE: PRT
<213> ORGANISM: Artificial sequence
<220> FEATURE:
<223> OTHER INFORMATION: Synthetic amino acid sequence

<400> SEQUENCE: 5

Ala Glu Lys Tyr Gly Phe Ser Lys Glu Val His Glu Ile Tyr Lys Asn
1               5                   10                  15

Lys Val Phe Glu Gly Phe Lys Lys Ile Pro Lys Thr Leu Gly Phe Leu
            20                  25                  30

Asn Lys Ile Thr Asn Leu Asn Glu Asn Tyr Gln Leu Lys Asp Gly Tyr
        35                  40                  45

Lys Ile Phe Ile Asn Val Ile Tyr Lys Phe Lys Asn Gly Glu Ser Arg
    50                  55                  60

Tyr Ala Lys Asp Val
65

<210> SEQ ID NO 6
<211> LENGTH: 149
<212> TYPE: PRT
<213> ORGANISM: Artificial sequence
<220> FEATURE:
<223> OTHER INFORMATION: Synthetic amino acid sequence

<400> SEQUENCE: 6

Phe Lys Tyr Ser Phe Tyr Lys Asn Glu Gln Pro Leu Lys Ala Ile Phe
1               5                   10                  15

Phe Phe Ser Ser Lys Lys Gln Phe Phe Glu Val Gln Lys Ser Leu Lys
            20                  25                  30

Glu Leu Phe His Asn Lys His Ser Val Phe Tyr Arg Ala Ala Ala Glu
        35                  40                  45

Leu Gly Phe Ser Lys Val Glu Phe Leu Arg Asp Ser Thr Lys Ser
    50                  55                  60

Ser Ala Phe Leu Tyr Asn Pro Glu Glu Phe Thr Val Lys Asn Thr Glu
65                  70                  75                  80

Phe Ile Asn Gln Ile Glu Asp Asn Val Met Ala Ile Val Leu Leu Asp
            85                  90                  95

Lys Tyr Ile Gly Asn Ile Asp Pro Leu Val Arg Asn Phe Pro Asp Asn
            100                 105                 110

Leu Ile Leu Gln Pro Ile Leu Lys Glu Lys Leu Glu Asp Ile Lys Pro
```

```
                        115                 120                 125
Phe Ile Ile Lys Ser Tyr Val Tyr Lys Met Gly Asn Phe Ile Pro Glu
            130                 135                 140

Cys Lys Pro Phe Ile
145

<210> SEQ ID NO 7
<211> LENGTH: 209
<212> TYPE: PRT
<213> ORGANISM: Artificial sequence
<220> FEATURE:
<223> OTHER INFORMATION: Synthetic amino acid sequence

<400> SEQUENCE: 7

Leu Lys Lys Met Glu Asp Lys Glu Lys Asn Leu Tyr Ile Gly Ile Asp
1               5                   10                  15

Leu Ser His Asp Thr Tyr Ala Arg Lys Thr Asn Leu Cys Ile Ala Ala
            20                  25                  30

Val Asp Asn Thr Gly Asp Ile Leu Tyr Ile Gly Lys His Lys Asn Leu
        35                  40                  45

Glu Leu Asn Glu Lys Met Asn Leu Asp Ile Leu Glu Lys Glu Tyr Ile
    50                  55                  60

Lys Ala Phe Glu Lys Tyr Ile Glu Lys Phe Asn Val Ser Pro Glu Asn
65                  70                  75                  80

Val Phe Ile Leu Arg Asp Gly Arg Phe Ile Glu Asp Ile Glu Ile Ile
                85                  90                  95

Lys Asn Phe Ile Ser Tyr Asn Asp Thr Lys Tyr Thr Leu Val Glu Val
            100                 105                 110

Asn Lys Asn Thr Asn Ile Asn Ser Tyr Asp Asp Leu Lys Glu Trp Ile
        115                 120                 125

Ile Lys Leu Asp Glu Asn Thr Tyr Ile Tyr Tyr Pro Lys Thr Phe Leu
    130                 135                 140

Asn Gln Lys Gly Val Glu Val Lys Ile Leu Glu Asn Asn Thr Asp Tyr
145                 150                 155                 160

Thr Ile Glu Glu Ile Ile Glu Gln Ile Tyr Leu Leu Thr Arg Val Ala
                165                 170                 175

His Ser Thr Pro Tyr Thr Asn Tyr Lys Leu Pro Tyr Pro Leu His Ile
            180                 185                 190

Ala Asn Lys Val Ala Leu Thr Asp Tyr Glu Trp Lys Leu Tyr Ile Pro
        195                 200                 205

Tyr

<210> SEQ ID NO 8
<211> LENGTH: 770
<212> TYPE: PRT
<213> ORGANISM: Pyrococcus furiosus

<400> SEQUENCE: 8

Met Lys Ala Ile Val Val Ile Asn Leu Val Lys Ile Asn Lys Ile
1               5                   10                  15

Ile Pro Asp Lys Ile Tyr Val Tyr Arg Leu Phe Asn Asp Pro Glu Glu
            20                  25                  30

Glu Leu Gln Lys Glu Gly Tyr Ser Ile Tyr Arg Leu Ala Tyr Glu Asn
        35                  40                  45

Val Gly Ile Val Ile Asp Pro Glu Asn Leu Ile Ile Ala Thr Thr Lys
    50                  55                  60
```

-continued

Glu Leu Glu Tyr Glu Gly Glu Phe Ile Pro Glu Gly Glu Ile Ser Phe
65                  70                  75                  80

Ser Glu Leu Arg Asn Asp Tyr Gln Ser Lys Leu Val Leu Arg Leu Leu
            85                  90                  95

Lys Glu Asn Gly Ile Gly Glu Tyr Glu Leu Ser Lys Leu Leu Arg Lys
        100                 105                 110

Phe Arg Lys Pro Lys Thr Phe Gly Asp Tyr Lys Val Ile Pro Ser Val
    115                 120                 125

Glu Met Ser Val Ile Lys His Asp Glu Asp Phe Tyr Leu Val Ile His
130                 135                 140

Ile Ile His Gln Ile Gln Ser Met Lys Thr Leu Trp Glu Leu Val Asn
145                 150                 155                 160

Lys Asp Pro Lys Glu Leu Glu Phe Leu Met Thr His Lys Glu Asn
                165                 170                 175

Leu Met Leu Lys Asp Ile Ala Ser Pro Leu Lys Thr Val Tyr Lys Pro
            180                 185                 190

Cys Phe Glu Glu Tyr Thr Lys Lys Pro Lys Leu Asp His Asn Gln Glu
        195                 200                 205

Ile Val Lys Tyr Trp Tyr Asn Tyr His Ile Glu Arg Tyr Trp Asn Thr
    210                 215                 220

Pro Glu Ala Lys Leu Glu Phe Tyr Arg Lys Phe Gly Gln Val Asp Leu
225                 230                 235                 240

Lys Gln Pro Ala Ile Leu Ala Lys Phe Ala Ser Lys Ile Lys Lys Asn
                245                 250                 255

Lys Asn Tyr Lys Ile Tyr Leu Leu Pro Gln Leu Val Val Pro Thr Tyr
            260                 265                 270

Asn Ala Glu Gln Leu Glu Ser Asp Val Ala Lys Glu Ile Leu Glu Tyr
        275                 280                 285

Thr Lys Leu Met Pro Glu Glu Arg Lys Glu Leu Leu Glu Asn Ile Leu
    290                 295                 300

Ala Glu Val Asp Ser Asp Ile Ile Asp Lys Ser Leu Ser Glu Ile Glu
305                 310                 315                 320

Val Glu Lys Ile Ala Gln Glu Leu Glu Asn Lys Ile Arg Val Arg Asp
                325                 330                 335

Asp Lys Gly Asn Ser Val Pro Ile Ser Gln Leu Asn Val Gln Lys Ser
            340                 345                 350

Gln Leu Leu Leu Trp Thr Asn Tyr Ser Arg Lys Tyr Pro Val Ile Leu
        355                 360                 365

Pro Tyr Glu Val Pro Glu Lys Phe Arg Lys Ile Arg Glu Ile Pro Met
    370                 375                 380

Phe Ile Ile Leu Asp Ser Gly Leu Leu Ala Asp Ile Gln Asn Phe Ala
385                 390                 395                 400

Thr Asn Glu Phe Arg Glu Leu Val Lys Ser Met Tyr Tyr Ser Leu Ala
                405                 410                 415

Lys Lys Tyr Asn Ser Leu Ala Lys Lys Ala Arg Ser Thr Asn Glu Ile
            420                 425                 430

Gly Leu Pro Phe Leu Asp Phe Arg Gly Lys Glu Lys Val Ile Thr Glu
        435                 440                 445

Asp Leu Asn Ser Asp Lys Gly Ile Ile Glu Val Val Glu Gln Val Ser
    450                 455                 460

Ser Phe Met Lys Gly Lys Glu Leu Gly Leu Ala Phe Ile Ala Ala Arg
465                 470                 475                 480

Asn Lys Leu Ser Ser Glu Lys Phe Glu Glu Ile Lys Arg Arg Leu Phe

```
                485                 490                 495
Asn Leu Asn Val Ile Ser Gln Val Val Asn Glu Asp Thr Leu Lys Asn
            500                 505                 510
Lys Arg Asp Lys Tyr Asp Arg Asn Arg Leu Asp Leu Phe Val Arg His
            515                 520                 525
Asn Leu Leu Phe Gln Val Leu Ser Lys Leu Gly Val Lys Tyr Tyr Val
            530                 535                 540
Leu Asp Tyr Arg Phe Asn Tyr Asp Tyr Ile Ile Gly Ile Asp Val Ala
545                 550                 555                 560
Pro Met Lys Arg Ser Glu Gly Tyr Ile Gly Gly Ser Ala Val Met Phe
                565                 570                 575
Asp Ser Gln Gly Tyr Ile Arg Lys Ile Val Pro Ile Lys Ile Gly Glu
            580                 585                 590
Gln Arg Gly Glu Ser Val Asp Met Asn Glu Phe Lys Glu Met Val
            595                 600                 605
Asp Lys Phe Lys Glu Phe Asn Ile Lys Leu Asp Asn Lys Lys Ile Leu
            610                 615                 620
Leu Leu Arg Asp Gly Arg Ile Thr Asn Asn Glu Glu Glu Gly Leu Lys
625                 630                 635                 640
Tyr Ile Ser Glu Met Phe Asp Ile Glu Val Val Thr Met Asp Val Ile
                645                 650                 655
Lys Asn His Pro Val Arg Ala Phe Ala Asn Met Lys Met Tyr Phe Asn
                660                 665                 670
Leu Gly Gly Ala Ile Tyr Leu Ile Pro His Lys Leu Lys Gln Ala Lys
            675                 680                 685
Gly Thr Pro Ile Pro Ile Lys Leu Ala Lys Lys Arg Ile Ile Lys Asn
            690                 695                 700
Gly Lys Val Glu Lys Gln Ser Ile Thr Arg Gln Asp Val Leu Asp Ile
705                 710                 715                 720
Phe Ile Leu Thr Arg Leu Asn Tyr Gly Ser Ile Ser Ala Asp Met Arg
                725                 730                 735
Leu Pro Ala Pro Val His Tyr Ala His Lys Phe Ala Asn Ala Ile Arg
            740                 745                 750
Asn Glu Trp Lys Ile Lys Glu Glu Phe Leu Ala Glu Gly Phe Leu Tyr
            755                 760                 765
Phe Val
    770

<210> SEQ ID NO 9
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 9

Gly Gly Arg Arg Ala Arg Arg Arg Arg Arg
1               5                   10

<210> SEQ ID NO 10
<211> LENGTH: 36
<212> TYPE: RNA
<213> ORGANISM: Artificial sequence
<220> FEATURE:
<223> OTHER INFORMATION: Synthetic nucleic acid sequence

<400> SEQUENCE: 10
```
uaaucccaca gccgccaguu ccgcuggcgg cauuuu        36

```
<210> SEQ ID NO 11
<211> LENGTH: 16
<212> TYPE: PRT
<213> ORGANISM: Artificial sequence
<220> FEATURE:
<223> OTHER INFORMATION: Synthetic amino acid sequence

<400> SEQUENCE: 11

Arg Gln Ile Lys Ile Trp Phe Gln Asn Arg Arg Met Lys Trp Lys Lys
1               5                   10                  15

<210> SEQ ID NO 12
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 12

Tyr Gly Arg Lys Lys Arg Arg Gln Arg Arg Arg
1               5                   10

<210> SEQ ID NO 13
<211> LENGTH: 12
<212> TYPE: PRT
<213> ORGANISM: Artificial sequence
<220> FEATURE:
<223> OTHER INFORMATION: Synthetic amino acid sequence

<400> SEQUENCE: 13

Arg Arg Gln Arg Arg Thr Ser Lys Leu Met Lys Arg
1               5                   10

<210> SEQ ID NO 14
<211> LENGTH: 27
<212> TYPE: PRT
<213> ORGANISM: Artificial sequence
<220> FEATURE:
<223> OTHER INFORMATION: Synthetic amino acid sequence

<400> SEQUENCE: 14

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 15
<211> LENGTH: 33
<212> TYPE: PRT
<213> ORGANISM: Artificial sequence
<220> FEATURE:
<223> OTHER INFORMATION: Synthetic amino acid sequence

<400> SEQUENCE: 15

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 16
<211> LENGTH: 16
<212> TYPE: PRT
```

```
<213> ORGANISM: Artificial sequence
<220> FEATURE:
<223> OTHER INFORMATION: Synthetic amino acid sequence

<400> SEQUENCE: 16

Arg Gln Ile Lys Ile Trp Phe Gln Asn Arg Arg Met Lys Trp Lys Lys
1               5                   10                  15

<210> SEQ ID NO 17
<211> LENGTH: 9
<212> TYPE: PRT
<213> ORGANISM: Artificial sequence
<220> FEATURE:
<223> OTHER INFORMATION: Synthetic amino acid sequence

<400> SEQUENCE: 17

Arg Lys Lys Arg Arg Gln Arg Arg Arg
1               5

<210> SEQ ID NO 18
<211> LENGTH: 8
<212> TYPE: PRT
<213> ORGANISM: Artificial sequence
<220> FEATURE:
<223> OTHER INFORMATION: Synthetic amino acid sequence

<400> SEQUENCE: 18

Arg Lys Lys Arg Arg Gln Arg Arg
1               5

<210> SEQ ID NO 19
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 19

Tyr Ala Arg Ala Ala Ala Arg Gln Ala Arg Ala
1               5                   10

<210> SEQ ID NO 20
<211> LENGTH: 11
<212> TYPE: PRT
<213> ORGANISM: Artificial sequence
<220> FEATURE:
<223> OTHER INFORMATION: Synthetic amino acid sequence

<400> SEQUENCE: 20

Thr His Arg Leu Pro Arg Arg Arg Arg Arg
1               5                   10

<210> SEQ ID NO 21
<211> LENGTH: 4
<212> TYPE: PRT
<213> ORGANISM: Artificial sequence
<220> FEATURE:
<223> OTHER INFORMATION: Synthetic amino acid sequence

<400> SEQUENCE: 21

Leu Phe Phe Val
1

<210> SEQ ID NO 22
<211> LENGTH: 9
<212> TYPE: PRT
<213> ORGANISM: Artificial sequence
```

-continued

```
<220> FEATURE:
<223> OTHER INFORMATION: Synthetic amino acid sequence

<400> SEQUENCE: 22

Val Asp Arg Glu Lys Leu Phe Phe Val
1               5

<210> SEQ ID NO 23
<211> LENGTH: 639
<212> TYPE: PRT
<213> ORGANISM: Artificial sequence
<220> FEATURE:
<223> OTHER INFORMATION: Synthetic amino acid sequence

<400> SEQUENCE: 23

Met Tyr Leu Asn Leu Tyr Lys Ile Asp Ile Pro Lys Lys Ile Lys Arg
1               5                   10                  15

Leu Tyr Phe Tyr Asn Pro Asp Met Glu Pro Lys Leu Phe Ala Arg Asn
                20                  25                  30

Leu Ser Arg Val Asn Asn Phe Lys Phe Gln Asp Ser Asn Asp Leu Val
            35                  40                  45

Trp Ile Glu Ile Pro Asp Ile Asp Phe Gln Ile Thr Pro Lys Asn Val
        50                  55                  60

Phe Gln Tyr Lys Val Glu Lys Glu Ile Ile Lys Glu Glu Asp
65                  70                  75                  80

Lys Lys Leu Phe Val Lys Thr Leu Tyr Lys Tyr Ile Lys Lys Leu Phe
                85                  90                  95

Leu Asp Asn Asp Phe Tyr Phe Lys Lys Gly Asn Asn Phe Ile Ser Asn
                100                 105                 110

Ser Glu Val Phe Ser Leu Asp Ser Asn Glu Asn Val Asn Ala His Leu
            115                 120                 125

Thr Tyr Lys Ile Lys Ile His Asn Ile Ser Asn Glu Tyr Tyr Leu Ser
        130                 135                 140

Ile Leu Pro Lys Phe Thr Phe Leu Ser Lys Glu Pro Ala Leu Glu Ser
145                 150                 155                 160

Ala Ile Lys Ser Gly Tyr Leu Tyr Asn Ile Lys Ser Gly Lys Ser Phe
                165                 170                 175

Pro Tyr Ile Ser Gly Leu Asp Gly Ile Leu Lys Ile Asp Ile Gly Asn
                180                 185                 190

Asn Gln Ile Val Glu Val Ala Tyr Pro Glu Asn Tyr Leu Phe Asn Phe
            195                 200                 205

Thr Thr Arg Asp Ala Gly Lys Tyr Gly Phe Ser Lys Glu Val His Glu
        210                 215                 220

Ile Tyr Lys Asn Lys Val Phe Glu Gly Phe Lys Lys Ile Pro Lys Thr
225                 230                 235                 240

Leu Gly Phe Leu Asn Lys Ile Thr Asn Leu Asn Glu Asn Tyr Gln Leu
                245                 250                 255

Lys Asp Gly Tyr Lys Ile Phe Ile Asn Val Ile Tyr Lys Phe Lys Asn
                260                 265                 270

Gly Glu Ser Arg Tyr Ala Lys Asp Val Phe Lys Tyr Ser Phe Tyr Lys
            275                 280                 285

Asn Glu Gln Pro Leu Lys Ala Ile Phe Phe Ser Ser Lys Lys Gln
        290                 295                 300

Phe Phe Glu Val Gln Lys Ser Leu Lys Glu Leu Phe His Asn Lys His
305                 310                 315                 320

Ser Val Phe Tyr Arg Ala Ala Ala Glu Leu Gly Phe Ser Lys Val Glu
```

```
                    325                 330                 335
Phe Leu Arg Asp Ser Lys Thr Lys Ser Ser Ala Phe Leu Tyr Asn Pro
                340                 345                 350

Glu Glu Phe Thr Val Lys Asn Thr Glu Phe Phe Asn Gln Ile Lys Asp
            355                 360                 365

Asn Val Met Ala Ile Val Leu Leu Asp Lys Tyr Ile Gly Asn Ile Asp
        370                 375                 380

Pro Leu Val Arg Asn Phe Pro Ser Gln Leu Ile Leu Gln Pro Ile Leu
385                 390                 395                 400

Lys Glu Lys Leu Glu Arg Ile Lys Pro Phe Ile Ile Lys Ser Tyr Val
                405                 410                 415

Tyr Lys Met Gly Asn Phe Ile Pro Glu Cys Lys Pro Phe Ile Leu Lys
            420                 425                 430

Lys Met Glu Asp Lys Glu Lys Asn Leu Tyr Ile Gly Ile Asp Leu Ser
        435                 440                 445

His Asp Thr Tyr Ala Arg Lys Thr Asn Leu Cys Ile Ala Ala Val Asp
    450                 455                 460

Asn Thr Gly Asp Ile Leu Tyr Ile Gly Lys His Lys Asn Leu Glu Leu
465                 470                 475                 480

Asn Glu Lys Met Asn Leu Asp Ile Leu Glu Lys Glu Tyr Ile Lys Ala
                485                 490                 495

Phe Glu Lys Tyr Ile Glu Lys Phe Asn Val Ser Pro Glu Asn Val Phe
            500                 505                 510

Ile Leu Arg Asp Gly Arg Phe Ile Glu Asp Ile Glu Ile Ile Lys Asn
        515                 520                 525

Phe Ile Ser Tyr Asn Asp Thr Lys Tyr Thr Leu Val Glu Val Asn Lys
    530                 535                 540

Asn Thr Asn Ile Asn Ser Tyr Asp Asp Leu Lys Glu Trp Ile Ile Lys
545                 550                 555                 560

Leu Asp Glu Asn Thr Tyr Ile Tyr Tyr Pro Lys Thr Phe Leu Asn Gln
                565                 570                 575

Lys Gly Val Glu Val Lys Ile Leu Glu Asn Asn Thr Asp Tyr Thr Ile
            580                 585                 590

Glu Glu Ile Ile Glu Gln Ile Tyr Leu Leu Thr Arg Val Ala His Ser
        595                 600                 605

Thr Pro Tyr Thr Asn Tyr Lys Leu Pro Tyr Pro Leu His Ile Ala Asn
    610                 615                 620

Lys Val Ala Leu Thr Asp Tyr Glu Trp Lys Leu Tyr Ile Pro Tyr
625                 630                 635

<210> SEQ ID NO 24
<211> LENGTH: 643
<212> TYPE: PRT
<213> ORGANISM: Artificial sequence
<220> FEATURE:
<223> OTHER INFORMATION: Synthetic amino acid sequence

<400> SEQUENCE: 24

Met Tyr Leu Asn Leu Tyr Lys Ile Asp Ile Pro Lys Lys Ile Lys Arg
1               5                   10                  15

Leu Tyr Phe Tyr Asn Pro Asp Met Glu Pro Lys Leu Phe Ala Arg Asn
                20                  25                  30

Leu Ser Arg Val Asn Asn Phe Lys Phe Gln Asp Ser Asn Asp Leu Val
            35                  40                  45

Trp Ile Glu Ile Pro Asp Ile Asp Phe Gln Ile Thr Pro Lys Asn Val
```

```
                50              55              60
Phe Gln Tyr Lys Val Glu Lys Glu Glu Ile Ile Lys Glu Glu Glu Asp
65                      70                  75                  80

Lys Lys Leu Phe Val Lys Thr Leu Tyr Lys Tyr Ile Lys Lys Leu Phe
                    85                  90                  95

Leu Asp Asn Asp Phe Tyr Phe Lys Lys Gly Asn Asn Phe Ile Ser Asn
                100                 105                 110

Ser Glu Val Phe Ser Leu Asp Ser Asn Glu Asn Val Asn Ala His Leu
                115                 120                 125

Thr Tyr Lys Ile Lys Ile His Asn Ile Ser Asn Glu Tyr Tyr Leu Ser
                130                 135                 140

Ile Leu Pro Lys Phe Thr Phe Leu Ser Lys Glu Pro Ala Leu Glu Ser
145                 150                 155                 160

Ala Ile Lys Ser Gly Tyr Leu Tyr Asn Ile Lys Ser Gly Lys Ser Phe
                165                 170                 175

Pro Tyr Ile Ser Gly Leu Asp Gly Ile Leu Lys Ile Asp Ile Gly Asn
                180                 185                 190

Asn Gln Ile Val Glu Val Ala Tyr Pro Glu Asn Tyr Leu Phe Asn Phe
                195                 200                 205

Thr Thr Arg Asp Ala Glu Lys Tyr Gly Phe Ser Lys Glu Val His Glu
210                 215                 220

Ile Tyr Lys Asn Lys Val Phe Glu Gly Phe Lys Lys Ile Pro Lys Thr
225                 230                 235                 240

Leu Gly Phe Leu Asn Lys Ile Thr Asn Leu Asn Glu Asn Tyr Gln Leu
                245                 250                 255

Lys Asp Gly Tyr Lys Ile Phe Ile Asn Val Ile Tyr Lys Phe Lys Asn
                260                 265                 270

Gly Glu Ser Arg Tyr Ala Lys Asp Val Phe Lys Tyr Ser Phe Tyr Lys
                275                 280                 285

Asn Glu Gln Pro Leu Lys Ala Ile Phe Phe Ser Ser Lys Lys Gln
                290                 295                 300

Phe Phe Glu Val Gln Lys Ser Leu Lys Glu Leu Phe His Asn Lys His
305                 310                 315                 320

Ser Val Phe Tyr Arg Ala Ala Ala Glu Leu Gly Phe Ser Lys Val Glu
                325                 330                 335

Phe Leu Arg Asp Ser Lys Thr Lys Ser Ser Ala Phe Leu Tyr Asn Pro
                340                 345                 350

Glu Glu Phe Thr Val Lys Asn Thr Glu Phe Phe Asn Gln Ile Lys Asp
                355                 360                 365

Asn Val Met Ala Ile Val Leu Leu Asp Lys Tyr Ile Gly Asn Ile Asp
370                 375                 380

Pro Leu Val Arg Asn Phe Pro Ser Gln Leu Ile Leu Gln Pro Ile Leu
385                 390                 395                 400

Lys Glu Lys Leu Glu Arg Ile Lys Pro Phe Ile Ile Lys Ser Tyr Val
                405                 410                 415

Tyr Lys Met Gly Asn Phe Ile Pro Glu Cys Lys Pro Phe Ile Leu Lys
                420                 425                 430

Lys Met Glu Asp Lys Glu Lys Asn Leu Tyr Ile Gly Ile Asp Leu Ser
                435                 440                 445

His Asp Thr Tyr Ala Arg Lys Thr Asn Leu Cys Ile Ala Ala Val Asp
                450                 455                 460

Asn Thr Gly Asp Ile Leu Tyr Ile Gly Lys His Lys Asn Leu Glu Leu
465                 470                 475                 480
```

Asn Glu Lys Met Asn Leu Asp Ile Leu Glu Lys Glu Tyr Ile Lys Ala
                485                 490                 495

Phe Glu Lys Tyr Ile Glu Lys Phe Asn Val Ser Pro Glu Asn Val Phe
            500                 505                 510

Ile Leu Arg Asp Gly Arg Phe Ile Glu Asp Ile Glu Ile Ile Lys Asn
            515                 520                 525

Phe Ile Ser Tyr Asn Asp Thr Lys Tyr Thr Leu Val Glu Val Asn Lys
            530                 535                 540

Asn Thr Asn Ile Asn Ser Tyr Asp Asp Leu Lys Glu Trp Ile Ile Lys
545                 550                 555                 560

Leu Asp Glu Asn Thr Tyr Ile Tyr Tyr Pro Lys Thr Phe Leu Asn Gln
                565                 570                 575

Lys Gly Val Glu Val Lys Ile Leu Glu Asn Asn Thr Asp Tyr Thr Ile
            580                 585                 590

Glu Glu Ile Ile Glu Gln Ile Tyr Leu Leu Thr Arg Val Ala His Ser
            595                 600                 605

Thr Pro Tyr Thr Asn Tyr Lys Leu Pro Tyr Pro Leu His Ile Ala Asn
            610                 615                 620

Lys Val Ala Leu Thr Asp Tyr Glu Trp Lys Leu Tyr Ile Pro Tyr Leu
625                 630                 635                 640

Phe Phe Val

<210> SEQ ID NO 25
<211> LENGTH: 648
<212> TYPE: PRT
<213> ORGANISM: Artificial sequence
<220> FEATURE:
<223> OTHER INFORMATION: Synthetic amino acid sequence

<400> SEQUENCE: 25

Met Tyr Leu Asn Leu Tyr Lys Ile Asp Ile Pro Lys Lys Ile Lys Arg
1               5                   10                  15

Leu Tyr Phe Tyr Asn Pro Asp Met Glu Pro Lys Leu Phe Ala Arg Asn
                20                  25                  30

Leu Ser Arg Val Asn Asn Phe Lys Phe Gln Asp Ser Asn Asp Leu Val
            35                  40                  45

Trp Ile Glu Ile Pro Asp Ile Asp Phe Gln Ile Thr Pro Lys Asn Val
        50                  55                  60

Phe Gln Tyr Lys Val Glu Lys Glu Ile Ile Lys Glu Glu Glu Asp
65                  70                  75                  80

Lys Lys Leu Phe Val Lys Thr Leu Tyr Lys Tyr Ile Lys Lys Leu Phe
                85                  90                  95

Leu Asp Asn Asp Phe Tyr Phe Lys Lys Gly Asn Asn Phe Ile Ser Asn
                100                 105                 110

Ser Glu Val Phe Ser Leu Asp Ser Asn Glu Asn Val Asn Ala His Leu
            115                 120                 125

Thr Tyr Lys Ile Lys Ile His Asn Ile Ser Asn Glu Tyr Tyr Leu Ser
        130                 135                 140

Ile Leu Pro Lys Phe Thr Phe Leu Ser Lys Glu Pro Ala Leu Glu Ser
145                 150                 155                 160

Ala Ile Lys Ser Gly Tyr Leu Tyr Asn Ile Lys Ser Gly Lys Ser Phe
                165                 170                 175

Pro Tyr Ile Ser Gly Leu Asp Gly Ile Leu Lys Ile Asp Ile Gly Asn
            180                 185                 190

-continued

```
Asn Gln Ile Val Glu Val Ala Tyr Pro Glu Asn Tyr Leu Phe Asn Phe
            195                 200                 205

Thr Thr Arg Asp Ala Glu Lys Tyr Gly Phe Ser Lys Glu Val His Glu
    210                 215                 220

Ile Tyr Lys Asn Lys Val Phe Glu Gly Phe Lys Lys Ile Pro Lys Thr
225                 230                 235                 240

Leu Gly Phe Leu Asn Lys Ile Thr Asn Leu Asn Glu Asn Tyr Gln Leu
                245                 250                 255

Lys Asp Gly Tyr Lys Ile Phe Ile Asn Val Ile Tyr Lys Phe Lys Asn
                260                 265                 270

Gly Glu Ser Arg Tyr Ala Lys Asp Val Phe Lys Tyr Ser Phe Tyr Lys
            275                 280                 285

Asn Glu Gln Pro Leu Lys Ala Ile Phe Phe Ser Ser Lys Lys Gln
    290                 295                 300

Phe Phe Glu Val Gln Lys Ser Leu Lys Glu Leu Phe His Asn Lys His
305                 310                 315                 320

Ser Val Phe Tyr Arg Ala Ala Ala Glu Leu Gly Phe Ser Lys Val Glu
                325                 330                 335

Phe Leu Arg Asp Ser Lys Thr Lys Ser Ser Ala Phe Leu Tyr Asn Pro
            340                 345                 350

Glu Glu Phe Thr Val Lys Asn Thr Glu Phe Phe Asn Gln Ile Lys Asp
    355                 360                 365

Asn Val Met Ala Ile Val Leu Leu Asp Lys Tyr Ile Gly Asn Ile Asp
370                 375                 380

Pro Leu Val Arg Asn Phe Pro Ser Gln Leu Ile Leu Gln Pro Ile Leu
385                 390                 395                 400

Lys Glu Lys Leu Glu Arg Ile Lys Pro Phe Ile Ile Lys Ser Tyr Val
                405                 410                 415

Tyr Lys Met Gly Asn Phe Ile Pro Glu Cys Lys Pro Phe Ile Leu Lys
            420                 425                 430

Lys Met Glu Asp Lys Glu Lys Asn Leu Tyr Ile Gly Ile Asp Leu Ser
    435                 440                 445

His Asp Thr Tyr Ala Arg Lys Thr Asn Leu Cys Ile Ala Ala Val Asp
450                 455                 460

Asn Thr Gly Asp Ile Leu Tyr Ile Gly Lys His Lys Asn Leu Glu Leu
465                 470                 475                 480

Asn Glu Lys Met Asn Leu Asp Ile Leu Glu Lys Glu Tyr Ile Lys Ala
                485                 490                 495

Phe Glu Lys Tyr Ile Glu Lys Phe Asn Val Ser Pro Glu Asn Val Phe
            500                 505                 510

Ile Leu Arg Asp Gly Arg Phe Ile Glu Asp Ile Glu Ile Ile Lys Asn
    515                 520                 525

Phe Ile Ser Tyr Asn Asp Thr Lys Tyr Thr Leu Val Glu Val Asn Lys
530                 535                 540

Asn Thr Asn Ile Asn Ser Tyr Asp Asp Leu Lys Glu Trp Ile Ile Lys
545                 550                 555                 560

Leu Asp Glu Asn Thr Tyr Ile Tyr Tyr Pro Lys Thr Phe Leu Asn Gln
                565                 570                 575

Lys Gly Val Glu Val Lys Ile Leu Glu Asn Asn Thr Asp Tyr Thr Ile
            580                 585                 590

Glu Glu Ile Ile Glu Gln Ile Tyr Leu Leu Thr Arg Val Ala His Ser
    595                 600                 605

Thr Pro Tyr Thr Asn Tyr Lys Leu Pro Tyr Pro Leu His Ile Ala Asn
```

```
            610                 615                 620
Lys Val Ala Leu Thr Asp Tyr Glu Trp Lys Leu Tyr Ile Pro Tyr Val
625                 630                 635                 640

Asp Arg Glu Lys Leu Phe Phe Val
                645

<210> SEQ ID NO 26
<211> LENGTH: 859
<212> TYPE: PRT
<213> ORGANISM: Homo sapiens

<400> SEQUENCE: 26

Met Tyr Ser Gly Ala Gly Pro Ala Leu Ala Pro Pro Ala Pro Pro Pro
1               5                   10                  15

Pro Ile Gln Gly Tyr Ala Phe Lys Pro Pro Arg Pro Asp Phe Gly
            20                  25                  30

Thr Ser Gly Arg Thr Ile Lys Leu Gln Ala Asn Phe Phe Glu Met Asp
            35                  40                  45

Ile Pro Lys Ile Asp Ile Tyr His Tyr Glu Leu Asp Ile Lys Pro Glu
        50                  55                  60

Lys Cys Pro Arg Arg Val Asn Arg Glu Ile Val Glu His Met Val Gln
65                  70                  75                  80

His Phe Lys Thr Gln Ile Phe Gly Asp Arg Lys Pro Val Phe Asp Gly
                85                  90                  95

Arg Lys Asn Leu Tyr Thr Ala Met Pro Leu Pro Ile Gly Arg Asp Lys
            100                 105                 110

Val Glu Leu Glu Val Thr Leu Pro Gly Glu Gly Lys Asp Arg Ile Phe
        115                 120                 125

Lys Val Ser Ile Lys Trp Val Ser Cys Val Ser Leu Gln Ala Leu His
130                 135                 140

Asp Ala Leu Ser Gly Arg Leu Pro Ser Val Pro Phe Glu Thr Ile Gln
145                 150                 155                 160

Ala Leu Asp Val Val Met Arg His Leu Pro Ser Met Arg Tyr Thr Pro
                165                 170                 175

Val Gly Arg Ser Phe Phe Thr Ala Ser Glu Gly Cys Ser Asn Pro Leu
            180                 185                 190

Gly Gly Gly Arg Glu Val Trp Phe Gly Phe His Gln Ser Val Arg Pro
        195                 200                 205

Ser Leu Trp Lys Met Met Leu Asn Ile Asp Val Ser Ala Thr Ala Phe
210                 215                 220

Tyr Lys Ala Gln Pro Val Ile Glu Phe Val Cys Glu Val Leu Asp Phe
225                 230                 235                 240

Lys Ser Ile Glu Glu Gln Gln Lys Pro Leu Thr Asp Ser Gln Arg Val
                245                 250                 255

Lys Phe Thr Lys Glu Ile Lys Gly Leu Lys Val Glu Ile Thr His Cys
            260                 265                 270

Gly Gln Met Lys Arg Lys Tyr Arg Val Cys Asn Val Thr Arg Arg Pro
        275                 280                 285

Ala Ser His Gln Thr Phe Pro Leu Gln Gln Glu Ser Gly Gln Thr Val
290                 295                 300

Glu Cys Thr Val Ala Gln Tyr Phe Lys Asp Arg His Lys Leu Val Leu
305                 310                 315                 320

Arg Tyr Pro His Leu Pro Cys Leu Gln Val Gly Gln Glu Gln Lys His
                325                 330                 335
```

```
Thr Tyr Leu Pro Leu Glu Val Cys Asn Ile Val Ala Gly Gln Arg Cys
            340                 345                 350

Ile Lys Lys Leu Thr Asp Asn Gln Thr Ser Thr Met Ile Arg Ala Thr
        355                 360                 365

Ala Arg Ser Ala Pro Asp Arg Gln Glu Glu Ile Ser Lys Leu Met Arg
    370                 375                 380

Ser Ala Ser Phe Asn Thr Asp Pro Tyr Val Arg Glu Phe Gly Ile Met
385                 390                 395                 400

Val Lys Asp Glu Met Thr Asp Val Thr Gly Arg Val Leu Gln Pro Pro
                405                 410                 415

Ser Ile Leu Tyr Gly Gly Arg Asn Lys Ala Ile Ala Thr Pro Val Gln
            420                 425                 430

Gly Val Trp Asp Met Arg Asn Lys Gln Phe His Thr Gly Ile Glu Ile
        435                 440                 445

Lys Val Trp Ala Ile Ala Cys Phe Ala Pro Gln Arg Gln Cys Thr Glu
    450                 455                 460

Val His Leu Lys Ser Phe Thr Glu Gln Leu Arg Lys Ile Ser Arg Asp
465                 470                 475                 480

Ala Gly Met Pro Ile Gln Gly Gln Pro Cys Phe Cys Lys Tyr Ala Gln
                485                 490                 495

Gly Ala Asp Ser Val Glu Pro Met Phe Arg His Leu Lys Asn Thr Tyr
            500                 505                 510

Ala Gly Leu Gln Leu Val Val Ile Leu Pro Gly Lys Thr Pro Val
        515                 520                 525

Tyr Ala Glu Val Lys Arg Val Gly Asp Thr Val Leu Gly Met Ala Thr
    530                 535                 540

Gln Cys Val Gln Met Lys Asn Val Gln Arg Thr Thr Pro Gln Thr Leu
545                 550                 555                 560

Ser Asn Leu Cys Leu Lys Ile Asn Val Lys Leu Gly Val Asn Asn
                565                 570                 575

Ile Leu Leu Pro Gln Gly Arg Pro Pro Val Phe Gln Gln Pro Val Ile
            580                 585                 590

Phe Leu Gly Ala Asp Val Thr His Pro Pro Ala Gly Asp Gly Lys Lys
        595                 600                 605

Pro Ser Ile Ala Ala Val Val Gly Ser Met Asp Ala His Pro Asn Arg
    610                 615                 620

Tyr Cys Ala Thr Val Arg Val Gln Gln His Arg Gln Glu Ile Ile Gln
625                 630                 635                 640

Asp Leu Ala Ala Met Val Arg Glu Leu Leu Ile Gln Phe Tyr Lys Ser
                645                 650                 655

Thr Arg Phe Lys Pro Thr Arg Ile Ile Phe Tyr Arg Asp Gly Val Ser
            660                 665                 670

Glu Gly Gln Phe Gln Gln Val Leu His His Glu Leu Leu Ala Ile Arg
        675                 680                 685

Glu Ala Cys Ile Lys Leu Glu Lys Asp Tyr Gln Pro Gly Ile Thr Phe
    690                 695                 700

Ile Val Val Gln Lys Arg His His Thr Arg Leu Phe Cys Thr Asp Lys
705                 710                 715                 720

Asn Glu Arg Val Gly Lys Ser Gly Asn Ile Pro Ala Gly Thr Thr Val
                725                 730                 735

Asp Thr Lys Ile Thr His Pro Thr Glu Phe Asp Phe Tyr Leu Cys Ser
            740                 745                 750

His Ala Gly Ile Gln Gly Thr Ser Arg Pro Ser His Tyr His Val Leu
```

```
                755                 760                 765
Trp Asp Asp Asn Arg Phe Ser Ser Asp Glu Leu Gln Ile Leu Thr Tyr
770                 775                 780
Gln Leu Cys His Thr Tyr Val Arg Cys Thr Arg Ser Val Ser Ile Pro
785                 790                 795                 800
Ala Pro Ala Tyr Tyr Ala His Leu Val Ala Phe Arg Ala Arg Tyr His
            805                 810                 815
Leu Val Asp Lys Glu His Asp Ser Ala Glu Gly Ser His Thr Ser Gly
            820                 825                 830
Gln Ser Asn Gly Arg Asp His Gln Ala Leu Ala Lys Ala Val Gln Val
            835                 840                 845
His Gln Asp Thr Leu Arg Thr Met Tyr Phe Ala
850                 855
```

<210> SEQ ID NO 27
<211> LENGTH: 984
<212> TYPE: PRT
<213> ORGANISM: Drosophila melanogaster

<400> SEQUENCE: 27

```
Met Ser Thr Glu Arg Glu Leu Ala Pro Gly Gly Pro Ala Gln Leu His
1               5                   10                  15
Pro His Thr Leu Pro Leu Thr Phe Pro Asp Leu Gln Met Thr Ser Thr
            20                  25                  30
Val Gly Ile Ile Gly Lys Val Tyr Glu Ser Gln Trp Thr Pro Ser Pro
        35                  40                  45
Thr Arg Pro Gln Ser Pro Ser Gln Ala Gln Thr Ser Phe Asp Thr Leu
    50                  55                  60
Thr Ser Pro Pro Ala Pro Gly Ser Ser Val Asn Pro Thr Ala Val Thr
65                  70                  75                  80
Ser Pro Ser Ala Gln Asn Val Ala Ala Gly Ala Thr Val Ala Gly
                85                  90                  95
Ala Ala Ala Thr Ala Ala Gln Val Ala Ser Ala Leu Gly Ala Thr Thr
                100                 105                 110
Gly Ser Val Thr Pro Ala Ile Ala Thr Ala Thr Pro Ala Thr Gln Pro
            115                 120                 125
Asp Met Pro Val Phe Thr Cys Pro Arg Arg Pro Asn Leu Gly Arg Glu
130                 135                 140
Gly Arg Pro Ile Val Leu Arg Ala Asn His Phe Gln Val Thr Met Pro
145                 150                 155                 160
Arg Gly Tyr Val His His Tyr Asp Ile Asn Ile Gln Pro Asp Lys Cys
                165                 170                 175
Pro Arg Lys Val Asn Arg Glu Ile Ile Glu Thr Met Val His Ala Tyr
                180                 185                 190
Ser Lys Ile Phe Gly Val Leu Lys Pro Val Phe Asp Gly Arg Asn Asn
            195                 200                 205
Leu Tyr Thr Arg Asp Pro Leu Pro Ile Gly Asn Glu Arg Leu Glu Leu
        210                 215                 220
Glu Val Thr Leu Pro Gly Glu Gly Lys Asp Arg Ile Phe Arg Val Thr
225                 230                 235                 240
Ile Lys Trp Gln Ala Gln Val Ser Leu Phe Asn Leu Glu Glu Ala Leu
                245                 250                 255
Glu Gly Arg Thr Arg Gln Ile Pro Tyr Asp Ala Ile Leu Ala Leu Asp
                260                 265                 270
```

```
Val Val Met Arg His Leu Pro Ser Met Thr Tyr Thr Pro Val Gly Arg
            275                 280                 285

Ser Phe Phe Ser Ser Pro Glu Gly Tyr Tyr His Pro Leu Gly Gly Gly
290                 295                 300

Arg Glu Val Trp Phe Gly Phe His Gln Ser Val Arg Pro Ser Gln Trp
305             310                 315                 320

Lys Met Met Leu Asn Ile Asp Val Ser Ala Thr Ala Phe Tyr Lys Ala
                325                 330                 335

Gln Pro Val Ile Asp Phe Met Cys Glu Val Leu Asp Ile Arg Asp Ile
                340                 345                 350

Asn Glu Gln Arg Lys Pro Leu Thr Asp Ser Gln Arg Val Lys Phe Thr
            355                 360                 365

Lys Glu Ile Lys Gly Leu Lys Ile Glu Ile Thr His Cys Gly Gln Met
        370                 375                 380

Arg Arg Lys Tyr Arg Val Cys Asn Val Thr Arg Arg Pro Ala Gln Met
385                 390                 395                 400

Gln Ser Phe Pro Leu Gln Leu Glu Asn Gly Gln Thr Val Glu Cys Thr
                405                 410                 415

Val Ala Lys Tyr Phe Leu Asp Lys Tyr Arg Met Lys Leu Arg Tyr Pro
            420                 425                 430

His Leu Pro Cys Leu Gln Val Gly Gln Glu His Lys His Thr Tyr Leu
        435                 440                 445

Pro Leu Glu Val Cys Asn Ile Val Ala Gly Gln Arg Cys Ile Lys Lys
    450                 455                 460

Leu Thr Asp Met Gln Thr Ser Thr Met Ile Lys Ala Thr Ala Arg Ser
465                 470                 475                 480

Ala Pro Asp Arg Glu Arg Glu Ile Asn Asn Leu Val Lys Arg Ala Asp
                485                 490                 495

Phe Asn Asn Asp Ser Tyr Val Gln Glu Phe Gly Leu Thr Ile Ser Asn
                500                 505                 510

Ser Met Met Glu Val Arg Gly Arg Val Leu Pro Pro Pro Lys Leu Gln
            515                 520                 525

Tyr Gly Gly Arg Val Ser Thr Gly Leu Thr Gly Gln Gln Leu Phe Pro
        530                 535                 540

Pro Gln Asn Lys Val Ser Leu Ala Ser Pro Asn Gln Gly Val Trp Asp
545                 550                 555                 560

Met Arg Gly Lys Gln Phe Phe Thr Gly Val Glu Ile Arg Ile Trp Ala
                565                 570                 575

Ile Ala Cys Phe Ala Pro Gln Arg Thr Val Arg Glu Asp Ala Leu Arg
            580                 585                 590

Asn Phe Thr Gln Gln Leu Gln Lys Ile Ser Asn Asp Ala Gly Met Pro
        595                 600                 605

Ile Ile Gly Gln Pro Cys Phe Cys Lys Tyr Ala Thr Gly Pro Asp Gln
    610                 615                 620

Val Glu Pro Met Phe Arg Tyr Leu Lys Ile Thr Phe Pro Gly Leu Gln
625                 630                 635                 640

Leu Val Val Val Leu Pro Gly Lys Thr Pro Val Tyr Ala Glu Val
                645                 650                 655

Lys Arg Val Gly Asp Thr Val Leu Gly Met Ala Thr Gln Cys Val Gln
                660                 665                 670

Ala Lys Asn Val Asn Lys Thr Ser Pro Gln Thr Leu Ser Asn Leu Cys
            675                 680                 685

Leu Lys Ile Asn Val Lys Leu Gly Gly Ile Asn Ser Ile Leu Val Pro
```

690                 695                 700
Ser Ile Arg Pro Lys Val Phe Asn Glu Pro Val Ile Phe Leu Gly Ala
705                 710                 715                 720

Asp Val Thr His Pro Ala Gly Asp Asn Lys Lys Pro Ser Ile Ala
                725                 730                 735

Ala Val Val Gly Ser Met Asp Ala His Pro Ser Arg Tyr Ala Ala Thr
                740                 745                 750

Val Arg Val Gln Gln His Arg Gln Glu Ile Ile Gln Glu Leu Ser Ser
                755                 760                 765

Met Val Arg Glu Leu Leu Ile Met Phe Tyr Lys Ser Thr Gly Gly Tyr
770                 775                 780

Lys Pro His Arg Ile Ile Leu Tyr Arg Asp Gly Val Ser Glu Gly Gln
785                 790                 795                 800

Phe Pro His Val Leu Gln His Glu Leu Thr Ala Ile Arg Glu Ala Cys
                805                 810                 815

Ile Lys Leu Glu Pro Glu Tyr Arg Pro Gly Ile Thr Phe Ile Val Val
                820                 825                 830

Gln Lys Arg His His Thr Arg Leu Phe Cys Ala Glu Lys Lys Glu Gln
                835                 840                 845

Ser Gly Lys Ser Gly Asn Ile Pro Ala Gly Thr Thr Val Asp Val Gly
850                 855                 860

Ile Thr His Pro Thr Glu Phe Asp Phe Tyr Leu Cys Ser His Gln Gly
865                 870                 875                 880

Ile Gln Gly Thr Ser Arg Pro Ser His Tyr His Val Leu Trp Asp Asp
                885                 890                 895

Asn His Phe Asp Ser Asp Glu Leu Gln Cys Leu Thr Tyr Gln Leu Cys
                900                 905                 910

His Thr Tyr Val Arg Cys Thr Arg Ser Val Ser Ile Pro Ala Pro Ala
                915                 920                 925

Tyr Tyr Ala His Leu Val Ala Phe Arg Ala Arg Tyr His Leu Val Glu
                930                 935                 940

Lys Glu His Asp Ser Gly Glu Gly Ser His Gln Ser Gly Cys Ser Glu
945                 950                 955                 960

Asp Arg Thr Pro Gly Ala Met Ala Arg Ala Ile Thr Val His Ala Asp
                965                 970                 975

Thr Lys Lys Val Met Tyr Phe Ala
                980

<210> SEQ ID NO 28
<211> LENGTH: 685
<212> TYPE: PRT
<213> ORGANISM: Thermus thermophilus

<400> SEQUENCE: 28

Met Asn His Leu Gly Lys Thr Glu Val Phe Leu Asn Arg Phe Ala Leu
1               5                   10                  15

Arg Pro Leu Asn Pro Glu Glu Leu Arg Pro Trp Arg Leu Glu Val Val
                20                  25                  30

Leu Asp Pro Pro Gly Arg Glu Glu Val Tyr Pro Leu Leu Ala Gln
                35                  40                  45

Val Ala Arg Arg Ala Gly Gly Val Thr Val Arg Met Gly Asp Gly Leu
                50                  55                  60

Ala Ser Trp Ser Pro Pro Glu Val Leu Val Leu Glu Gly Thr Leu Ala
65                  70                  75                  80

-continued

```
Arg Met Gly Gln Thr Tyr Ala Tyr Arg Leu Tyr Pro Lys Gly Arg
                85                  90                  95
Pro Leu Asp Pro Lys Asp Pro Gly Glu Arg Ser Val Leu Ser Ala Leu
            100                 105                 110
Ala Arg Arg Leu Leu Gln Glu Arg Leu Arg Arg Leu Glu Gly Val Trp
        115                 120                 125
Val Glu Gly Leu Ala Val Tyr Arg Arg Glu His Ala Arg Gly Pro Gly
    130                 135                 140
Trp Arg Val Leu Gly Gly Ala Val Leu Asp Leu Trp Val Ser Asp Ser
145                 150                 155                 160
Gly Ala Phe Leu Leu Glu Val Asp Pro Ala Tyr Arg Ile Leu Cys Glu
                165                 170                 175
Met Ser Leu Glu Ala Trp Leu Ala Gln Gly His Pro Leu Pro Lys Arg
            180                 185                 190
Val Arg Asn Ala Tyr Asp Arg Arg Thr Trp Glu Leu Leu Arg Leu Gly
        195                 200                 205
Glu Glu Asp Pro Lys Glu Leu Pro Leu Pro Gly Gly Leu Ser Leu Leu
    210                 215                 220
Asp Tyr His Ala Ser Lys Gly Arg Leu Gln Gly Arg Glu Gly Gly Arg
225                 230                 235                 240
Val Ala Trp Val Ala Asp Pro Lys Asp Pro Arg Lys Pro Ile Pro His
                245                 250                 255
Leu Thr Gly Leu Leu Val Pro Val Leu Thr Leu Glu Asp Leu His Glu
            260                 265                 270
Glu Glu Gly Ser Leu Ala Leu Ser Leu Pro Trp Glu Glu Arg Arg Arg
        275                 280                 285
Arg Thr Arg Glu Ile Ala Ser Trp Ile Gly Arg Arg Leu Gly Leu Gly
    290                 295                 300
Thr Pro Glu Ala Val Arg Ala Gln Ala Tyr Arg Leu Ser Ile Pro Lys
305                 310                 315                 320
Leu Met Gly Arg Arg Ala Val Ser Lys Pro Ala Asp Ala Leu Arg Val
                325                 330                 335
Gly Phe Tyr Arg Ala Gln Glu Thr Ala Leu Ala Leu Leu Arg Leu Asp
            340                 345                 350
Gly Ala Gln Gly Trp Pro Glu Phe Leu Arg Arg Ala Leu Leu Arg Ala
        355                 360                 365
Phe Gly Ala Ser Gly Ala Ser Leu Arg Leu His Thr Leu His Ala His
    370                 375                 380
Pro Ser Gln Gly Leu Ala Phe Arg Glu Ala Leu Arg Lys Ala Lys Glu
385                 390                 395                 400
Glu Gly Val Gln Ala Val Leu Val Leu Thr Pro Pro Met Ala Trp Glu
                405                 410                 415
Asp Arg Asn Arg Leu Lys Ala Leu Leu Leu Arg Glu Gly Leu Pro Ser
            420                 425                 430
Gln Ile Leu Asn Val Pro Leu Arg Glu Glu Arg His Arg Trp Glu
        435                 440                 445
Asn Ala Leu Leu Gly Leu Leu Ala Lys Ala Gly Leu Gln Val Val Ala
    450                 455                 460
Leu Ser Gly Ala Tyr Pro Ala Glu Leu Ala Val Gly Phe Asp Ala Gly
465                 470                 475                 480
Gly Arg Glu Ser Phe Arg Phe Gly Gly Ala Ala Cys Ala Val Gly Gly
                485                 490                 495
Asp Gly Gly His Leu Leu Trp Thr Leu Pro Glu Ala Gln Ala Gly Glu
```

```
                    500                 505                 510
Arg Ile Pro Gln Glu Val Val Trp Asp Leu Leu Glu Thr Leu Trp
            515                 520                 525

Ala Phe Arg Arg Lys Ala Gly Arg Leu Pro Ser Arg Val Leu Leu Leu
        530                 535                 540

Arg Asp Gly Arg Val Pro Gln Asp Glu Phe Ala Leu Ala Leu Glu Ala
545                 550                 555                 560

Leu Ala Arg Glu Gly Ile Ala Tyr Asp Leu Val Ser Val Arg Lys Ser
                565                 570                 575

Gly Gly Gly Arg Val Tyr Pro Val Gln Gly Arg Leu Ala Asp Gly Leu
            580                 585                 590

Tyr Val Pro Leu Glu Asp Lys Thr Phe Leu Leu Leu Thr Val His Arg
        595                 600                 605

Asp Phe Arg Gly Thr Pro Arg Pro Leu Lys Leu Val His Glu Ala Gly
        610                 615                 620

Asp Thr Pro Leu Glu Ala Leu Ala His Gln Ile Phe His Leu Thr Arg
625                 630                 635                 640

Leu Tyr Pro Ala Ser Gly Phe Ala Phe Pro Arg Leu Pro Ala Pro Leu
                645                 650                 655

His Leu Ala Asp Arg Leu Val Lys Glu Val Gly Arg Leu Gly Ile Arg
            660                 665                 670

His Leu Lys Glu Val Asp Arg Glu Lys Leu Phe Phe Val
        675                 680                 685

<210> SEQ ID NO 29
<211> LENGTH: 771
<212> TYPE: PRT
<213> ORGANISM: Pyrococcus furiosus

<400> SEQUENCE: 29

Ser Met Lys Ala Ile Val Val Ile Asn Leu Val Lys Ile Asn Lys Lys
1               5                   10                  15

Ile Ile Pro Asp Lys Ile Tyr Val Tyr Arg Leu Phe Asn Asp Pro Glu
            20                  25                  30

Glu Glu Leu Gln Lys Gly Tyr Ser Ile Tyr Arg Leu Ala Tyr Glu
        35                  40                  45

Asn Val Gly Ile Val Ile Asp Pro Glu Asn Leu Ile Ile Ala Thr Thr
    50                  55                  60

Lys Glu Leu Glu Tyr Glu Gly Glu Phe Ile Pro Glu Gly Glu Ile Ser
65              70                  75                  80

Phe Ser Glu Leu Arg Asn Asp Tyr Gln Ser Lys Leu Val Leu Arg Leu
                85                  90                  95

Leu Lys Glu Asn Gly Ile Gly Tyr Glu Leu Ser Lys Leu Leu Arg
            100                 105                 110

Lys Phe Arg Lys Pro Lys Thr Phe Gly Asp Tyr Lys Val Ile Pro Ser
        115                 120                 125

Val Glu Met Ser Val Ile Lys His Asp Glu Asp Phe Tyr Leu Val Ile
    130                 135                 140

His Ile Ile His Gln Ile Gln Ser Met Lys Thr Leu Trp Glu Leu Val
145                 150                 155                 160

Asn Lys Asp Pro Lys Glu Leu Glu Glu Phe Leu Met Thr His Lys Glu
                165                 170                 175

Asn Leu Met Leu Lys Asp Ile Ala Ser Pro Leu Lys Thr Val Tyr Lys
            180                 185                 190
```

-continued

```
Pro Cys Phe Glu Glu Tyr Thr Lys Lys Pro Lys Leu Asp His Asn Gln
            195                 200                 205
Glu Ile Val Lys Tyr Trp Tyr Asn Tyr His Ile Glu Arg Tyr Trp Asn
        210                 215                 220
Thr Pro Glu Ala Lys Leu Glu Phe Tyr Arg Lys Phe Gly Gln Val Asp
225                 230                 235                 240
Leu Lys Gln Pro Ala Ile Leu Ala Lys Phe Ala Ser Lys Ile Lys Lys
                245                 250                 255
Asn Lys Asn Tyr Lys Ile Tyr Leu Leu Pro Gln Leu Val Val Pro Thr
            260                 265                 270
Tyr Asn Ala Glu Gln Leu Glu Ser Asp Val Ala Lys Glu Ile Leu Glu
        275                 280                 285
Tyr Thr Lys Leu Met Pro Glu Glu Arg Lys Glu Leu Leu Glu Asn Ile
        290                 295                 300
Leu Ala Glu Val Asp Ser Asp Ile Ile Asp Lys Ser Leu Ser Glu Ile
305                 310                 315                 320
Glu Val Glu Lys Ile Ala Gln Glu Leu Glu Asn Lys Ile Arg Val Arg
                325                 330                 335
Asp Asp Lys Gly Asn Ser Val Pro Ile Ser Gln Leu Asn Val Gln Lys
            340                 345                 350
Ser Gln Leu Leu Leu Trp Thr Asn Tyr Ser Arg Lys Tyr Pro Val Ile
        355                 360                 365
Leu Pro Tyr Glu Val Pro Glu Lys Phe Arg Lys Ile Arg Glu Ile Pro
        370                 375                 380
Met Phe Ile Ile Leu Asp Ser Gly Leu Leu Ala Asp Ile Gln Asn Phe
385                 390                 395                 400
Ala Thr Asn Glu Phe Arg Glu Leu Val Lys Ser Met Tyr Tyr Ser Leu
                405                 410                 415
Ala Lys Lys Tyr Asn Ser Leu Ala Lys Lys Ala Arg Ser Thr Asn Glu
            420                 425                 430
Ile Gly Leu Pro Phe Leu Asp Phe Arg Gly Lys Glu Lys Val Ile Thr
        435                 440                 445
Glu Asp Leu Asn Ser Asp Lys Gly Ile Ile Glu Val Val Glu Gln Val
450                 455                 460
Ser Ser Phe Met Lys Gly Lys Glu Leu Gly Leu Ala Phe Ile Ala Ala
465                 470                 475                 480
Arg Asn Lys Leu Ser Ser Glu Lys Phe Glu Glu Ile Lys Arg Arg Leu
                485                 490                 495
Phe Asn Leu Asn Val Ile Ser Gln Val Val Asn Glu Asp Thr Leu Lys
            500                 505                 510
Asn Lys Arg Asp Lys Tyr Asp Arg Asn Arg Leu Asp Leu Phe Val Arg
        515                 520                 525
His Asn Leu Leu Phe Gln Val Leu Ser Lys Leu Gly Val Lys Tyr Tyr
        530                 535                 540
Val Leu Asp Tyr Arg Phe Asn Tyr Asp Tyr Ile Gly Ile Asp Val
545                 550                 555                 560
Ala Pro Met Lys Arg Ser Glu Gly Tyr Ile Gly Gly Ser Ala Val Met
                565                 570                 575
Phe Asp Ser Gln Gly Tyr Ile Arg Lys Ile Val Pro Ile Lys Ile Gly
            580                 585                 590
Glu Gln Arg Gly Glu Ser Val Asp Met Asn Glu Phe Phe Lys Glu Met
        595                 600                 605
Val Asp Lys Phe Lys Glu Phe Asn Ile Lys Leu Asp Asn Lys Lys Ile
```

```
                    610                 615                 620
Leu Leu Leu Arg Asp Gly Arg Ile Thr Asn Asn Glu Glu Gly Leu
625                 630                 635                 640

Lys Tyr Ile Ser Glu Met Phe Asp Ile Glu Val Val Thr Met Asp Val
                645                 650                 655

Ile Lys Asn His Pro Val Arg Ala Phe Ala Asn Met Lys Met Tyr Phe
                660                 665                 670

Asn Leu Gly Gly Ala Ile Tyr Leu Ile Pro His Lys Leu Lys Gln Ala
                675                 680                 685

Lys Gly Thr Pro Ile Pro Ile Lys Leu Ala Lys Lys Arg Ile Ile Lys
                690                 695                 700

Asn Gly Lys Val Glu Lys Gln Ser Ile Thr Arg Gln Asp Val Leu Asp
705                 710                 715                 720

Ile Phe Ile Leu Thr Arg Leu Asn Tyr Gly Ser Ile Ser Ala Asp Met
                725                 730                 735

Arg Leu Pro Ala Pro Val His Tyr Ala His Lys Phe Ala Asn Ala Ile
                740                 745                 750

Arg Asn Glu Trp Lys Ile Lys Glu Glu Phe Leu Ala Glu Gly Phe Leu
                755                 760                 765

Tyr Phe Val
        770

<210> SEQ ID NO 30
<211> LENGTH: 125
<212> TYPE: PRT
<213> ORGANISM: Pyrococcus furiosus
<220> FEATURE:
<221> NAME/KEY: UNSURE
<222> LOCATION: (12)..(12)
<220> FEATURE:
<221> NAME/KEY: UNSURE
<222> LOCATION: (107)..(107)
<220> FEATURE:
<221> NAME/KEY: UNSURE
<222> LOCATION: (120)..(120)

<400> SEQUENCE: 30

Ile Ile Glu Val Val Glu Gln Val Ser Ser Phe Xaa Lys Gly Lys Glu
1               5                   10                  15

Leu Gly Leu Ala Phe Ile Ala Ala Arg Asn Lys Leu Ser Ser Glu Lys
                20                  25                  30

Phe Glu Glu Ile Lys Arg Arg Leu Phe Asn Leu Asn Val Ile Ser Gln
            35                  40                  45

Val Val Asn Glu Asp Thr Leu Lys Asn Lys Arg Asp Lys Tyr Asp Arg
        50                  55                  60

Asn Arg Leu Asp Leu Phe Val Arg His Asn Leu Leu Phe Gln Val Leu
65                  70                  75                  80

Ser Lys Leu Gly Val Lys Tyr Tyr Val Leu Asp Tyr Arg Phe Asn Tyr
                85                  90                  95

Asp Tyr Ile Ile Gly Ile Asp Val Ala Pro Xaa Lys Arg Ser Glu Gly
                100                 105                 110

Tyr Ile Gly Gly Ser Ala Val Xaa Phe Asp Ser Gln Gly
            115                 120                 125
```

UNITED STATES PATENT AND TRADEMARK OFFICE
CERTIFICATE OF CORRECTION

PATENT NO. : 10,253,311 B2
APPLICATION NO. : 15/129382
DATED : April 9, 2019
INVENTOR(S) : Doudna et al.

It is certified that error appears in the above-identified patent and that said Letters Patent is hereby corrected as shown below:

In the Specification

Column 35, Line 9, should read:
Akyürek et al. (2000) Mol. Med. 6:983; and U.S. Patent No.

In the Claims

Column 110, Claim 15, Lines 18 and 19, should read:
amino-terminal domain (N-domain), (ii) a PIWI/Argo-
naute/Zwille (PAZ) domain, (iii) a MID domain, and Signed and Sealed this
Third Day of September, 2019

Andrei Iancu
*Director of the United States Patent and Trademark Office*